US012252532B2

(12) United States Patent
Ruike et al.

(10) Patent No.: US 12,252,532 B2
(45) Date of Patent: Mar. 18, 2025

(54) ANTI-MYOSTATIN ANTIBODIES AND METHODS OF USE

(71) Applicant: Chugai Seiyaku Kabushiki Kaisha, Tokyo (JP)

(72) Inventors: Yoshinao Ruike, Singapore (SG); Taichi Kuramochi, Singapore (SG)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 20 days.

(21) Appl. No.: 17/742,824

(22) Filed: May 12, 2022

(65) Prior Publication Data
US 2022/0275076 A1   Sep. 1, 2022

Related U.S. Application Data

(62) Division of application No. 16/065,192, filed as application No. PCT/JP2016/088302 on Dec. 22, 2016, now Pat. No. 11,359,009.

(30) Foreign Application Priority Data

Dec. 25, 2015  (JP) ................. 2015-253346

(51) Int. Cl.
C07K 16/22 (2006.01)
A61K 39/00 (2006.01)
A61P 21/00 (2006.01)

(52) U.S. Cl.
CPC .............. *C07K 16/22* (2013.01); *A61P 21/00* (2018.01); *A61K 2039/505* (2013.01); *C07K 2317/21* (2013.01); *C07K 2317/24* (2013.01); *C07K 2317/52* (2013.01); *C07K 2317/56* (2013.01); *C07K 2317/567* (2013.01); *C07K 2317/76* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,689,299 A | 8/1987 | Insel et al. |
| 4,801,687 A | 1/1989 | Ngo |
| 5,202,253 A | 4/1993 | Esmon et al. |
| 5,322,678 A | 6/1994 | Morgan, Jr. et al. |
| 5,501,854 A | 3/1996 | Raso |
| 5,585,089 A | 12/1996 | Queen et al. |
| 5,639,641 A | 6/1997 | Pedersen et al. |
| 5,795,965 A | 8/1998 | Tsuchiya et al. |
| 5,827,733 A | 10/1998 | Lee et al. |
| 5,830,478 A | 11/1998 | Raso et al. |
| 5,935,935 A | 8/1999 | Connelly et al. |
| 5,990,286 A | 11/1999 | Khawli et al. |
| 5,994,524 A | 11/1999 | Matsushima et al. |
| 6,024,956 A | 2/2000 | Matsushima et al. |
| 6,025,158 A | 2/2000 | Gonzalez et al. |
| 6,096,506 A | 8/2000 | Lee et al. |
| 6,165,745 A | 12/2000 | Ward et al. |
| 6,245,894 B1 | 6/2001 | Matsushima et al. |
| 6,329,511 B1 | 12/2001 | Vasquez et al. |
| 6,458,355 B1 | 10/2002 | Hsei et al. |
| 6,485,943 B2 | 11/2002 | Stevens et al. |
| 6,677,436 B1 | 1/2004 | Sato et al. |
| 6,737,056 B1 | 5/2004 | Presta |
| 6,821,505 B2 | 11/2004 | Ward |
| 6,884,879 B1 | 4/2005 | Baca et al. |
| 6,913,747 B1 | 7/2005 | Co et al. |
| 7,052,873 B2 | 5/2006 | Tuschiya |
| 7,138,501 B2 | 11/2006 | Ruben et al. |
| 7,247,302 B1 | 7/2007 | Rosok et al. |
| 7,261,893 B2 | 8/2007 | Veldman et al. |
| 7,276,585 B2 | 10/2007 | Lazar et al. |
| 7,282,568 B2 | 10/2007 | Teeling et al. |

(Continued)

FOREIGN PATENT DOCUMENTS

| | | |
|---|---|---|
| AU | 2010206050 A1 | 8/2010 |
| AU | 2011244851 A1 | 11/2011 |

(Continued)

OTHER PUBLICATIONS

Vajdos et al. (J Mol Biol. Jul. 5, 2002;320(2):415-28 (Year: 2002).*
Brown et al. (J Immunol. May 1996;156(9):3285-91 (Year: 1996).*
Pirruccello-Straub et al (Scientific Reports, vol. 8, Article No. 2292 (2018)) (Year: 2018).*
Igawa et al (Nat Biotechnol. Nov. 2010;28(11):1203-7) (Year: 2010).*
Nimmerjahn et al (Nat Rev Immunol. Jan. 2008;8(1):34-47; provided in previous Office Action mailed Aug. 21, 2019) (Year: 2008).*
Lazar (Proc Natl Acad Sci U S A. Mar. 14, 2006;103(11):4005-10. Epub Mar. 6, 2006) (Year: 2006).*

(Continued)

*Primary Examiner* — Brian Gangle
*Assistant Examiner* — Andrea K McCollum
(74) *Attorney, Agent, or Firm* — Nixon & Vanderhye P.C.

(57) ABSTRACT

The invention provides anti-myostatin antibodies and methods of using the same. In some embodiments, an isolated anti-myostatin antibody of the present invention binds to mature myostatin, and uptake of the antibody into cells is enhanced when complexed with the antigen. The invention also provides isolated nucleic acids encoding an anti-myostatin antibody of the present invention. The invention also provides host cells comprising a nucleic acid of the present invention. The invention also provides a method of producing an antibody comprising culturing a host cell of the present invention so that the antibody is produced. Anti-myostatin antibodies of the present invention may be for use as a medicament. Anti-myostatin antibodies of the present invention may be for use in treating a muscle wasting disease, in increasing mass of muscle tissue or in increasing strength of muscle tissue.

6 Claims, 6 Drawing Sheets

Specification includes a Sequence Listing.

(56) References Cited

U.S. PATENT DOCUMENTS

| | | |
|---|---|---|
| 7,317,091 B2 | 1/2008 | Lazar et al. |
| 7,320,789 B2 | 1/2008 | Aghajanian et al. |
| 7,358,054 B2 | 4/2008 | Lyne et al. |
| 7,361,740 B2 | 4/2008 | Hinton et al. |
| 7,365,166 B2 | 4/2008 | Baca et al. |
| 7,371,826 B2 | 5/2008 | Presta |
| 7,615,213 B2 | 11/2009 | Kasaian et al. |
| 7,632,499 B2 | 12/2009 | Davies et al. |
| 7,632,924 B2 | 12/2009 | Cho et al. |
| 7,662,925 B2 | 2/2010 | Lazar et al. |
| 7,667,004 B2 | 2/2010 | Zhong et al. |
| 7,670,600 B2 | 3/2010 | Dall'acqua et al. |
| 7,731,961 B1 | 6/2010 | Aghajanian et al. |
| 7,785,791 B2 | 8/2010 | Presta |
| 7,786,270 B2 | 8/2010 | Johnson et al. |
| 7,807,159 B2 | 10/2010 | Chin et al. |
| 7,820,800 B2 | 10/2010 | Rossi et al. |
| 7,888,486 B2 | 2/2011 | Walsh et al. |
| 7,955,590 B2 | 6/2011 | Gillies et al. |
| 7,960,512 B2 | 6/2011 | Stavenhagen et al. |
| 8,062,635 B2 | 11/2011 | Hattori et al. |
| 8,063,187 B2 | 11/2011 | Chu et al. |
| 8,101,720 B2 | 1/2012 | Lazar et al. |
| 8,147,829 B2 | 4/2012 | Hariharan |
| 8,188,231 B2 | 5/2012 | Lazar et al. |
| 8,193,318 B2 | 6/2012 | Koenig et al. |
| 8,323,962 B2 | 12/2012 | Dall'Acqua et al. |
| 8,329,186 B2 | 12/2012 | Kim et al. |
| 8,388,955 B2 | 3/2013 | Lazar et al. |
| 8,410,328 B2 | 4/2013 | Chung et al. |
| 8,414,893 B2 | 4/2013 | Biere-Citron et al. |
| 8,415,459 B2 * | 4/2013 | LaVallie ................ A61P 21/00 530/387.9 |
| 8,497,355 B2 | 7/2013 | Igawa et al. |
| 8,551,485 B2 | 10/2013 | Bernett et al. |
| 8,562,991 B2 | 10/2013 | Igawa et al. |
| 8,604,174 B2 | 12/2013 | Babcook et al. |
| 8,609,097 B2 | 12/2013 | Bohrmann et al. |
| 8,637,641 B2 | 1/2014 | Dahiyat et al. |
| 8,652,466 B2 | 2/2014 | Stavenhagen et al. |
| 8,679,490 B2 | 3/2014 | Dennis et al. |
| 8,685,725 B2 | 4/2014 | Beliard et al. |
| 8,734,798 B2 | 5/2014 | Finney et al. |
| 8,735,545 B2 | 5/2014 | Lazar et al. |
| 8,753,629 B2 | 6/2014 | Lazar et al. |
| 8,778,345 B2 | 7/2014 | Zhang et al. |
| 8,802,820 B2 | 8/2014 | Chamberlain et al. |
| 8,802,823 B2 | 8/2014 | Lazar et al. |
| 8,999,343 B2 | 4/2015 | Han et al. |
| 9,029,515 B2 | 5/2015 | Pons et al. |
| 9,051,373 B2 | 6/2015 | Lazar et al. |
| 9,079,949 B1 | 7/2015 | Andrien, Jr. et al. |
| 9,096,651 B2 | 8/2015 | Igawa et al. |
| 9,107,861 B1 | 8/2015 | Andrien, Jr. et al. |
| 9,255,154 B2 | 2/2016 | Feldhaus et al. |
| 9,315,577 B2 | 4/2016 | Foltz et al. |
| 9,334,334 B2 | 5/2016 | Mcwhirter et al. |
| 9,447,190 B2 | 9/2016 | Flanagan et al. |
| 9,481,725 B2 | 11/2016 | Dutzar et al. |
| 9,540,449 B2 | 1/2017 | Yancopoulos et al. |
| 9,605,061 B2 | 3/2017 | Lazar et al. |
| 9,644,018 B2 | 5/2017 | Stevis et al. |
| 9,648,856 B2 | 5/2017 | Mcwhirter et al. |
| 9,670,269 B2 | 6/2017 | Igawa et al. |
| 9,688,762 B2 | 6/2017 | Igawa et al. |
| 9,701,759 B2 | 7/2017 | Desjarlais et al. |
| 9,765,135 B2 | 9/2017 | Ruike et al. |
| 9,790,273 B2 | 10/2017 | Murphy et al. |
| 9,828,429 B2 | 11/2017 | Igawa et al. |
| 9,868,948 B2 | 1/2018 | Igawa et al. |
| 9,890,218 B2 | 2/2018 | Mimoto et al. |
| 9,890,377 B2 | 2/2018 | Igawa et al. |
| 9,920,134 B2 | 3/2018 | Jackson et al. |
| 9,969,800 B2 | 5/2018 | Igawa et al. |
| 10,000,560 B2 | 6/2018 | Ruike et al. |
| 10,023,630 B2 | 7/2018 | Ruike et al. |
| 10,111,953 B2 | 10/2018 | Swergold et al. |
| 10,233,252 B2 | 3/2019 | Shusta et al. |
| 10,253,100 B2 | 4/2019 | Igawa et al. |
| 10,385,122 B2 | 8/2019 | Ruike et al. |
| 10,472,623 B2 | 11/2019 | Igawa et al. |
| 10,519,229 B2 | 12/2019 | Igawa et al. |
| 10,919,953 B2 | 2/2021 | Katada et al. |
| 11,046,784 B2 | 6/2021 | Igawa et al. |
| 11,359,009 B2 | 6/2022 | Ruike et al. |
| 11,597,760 B2 | 3/2023 | Ruike et al. |
| 11,891,434 B2 | 2/2024 | Igawa et al. |
| 2002/0082396 A1 | 6/2002 | Matsushima et al. |
| 2002/0098193 A1 | 7/2002 | Ward |
| 2002/0137897 A1 | 9/2002 | Stevens et al. |
| 2002/0142374 A1 | 10/2002 | Gallo et al. |
| 2002/0164339 A1 | 11/2002 | Do Couto et al. |
| 2003/0059937 A1 | 3/2003 | Ruben et al. |
| 2003/0077283 A1 | 4/2003 | Ye |
| 2003/0103970 A1 | 6/2003 | Tsuchiya |
| 2003/0138422 A1 | 7/2003 | Aghajanian et al. |
| 2003/0224397 A1 | 12/2003 | Lowman et al. |
| 2004/0001822 A1 | 1/2004 | Levanon et al. |
| 2004/0001839 A1 | 1/2004 | Levanon et al. |
| 2004/0002450 A1 | 1/2004 | Lazarovits et al. |
| 2004/0081651 A1 | 4/2004 | Lyne et al. |
| 2004/0110226 A1 | 6/2004 | Lazar et al. |
| 2004/0132101 A1 | 7/2004 | Lazar et al. |
| 2004/0133357 A1 | 7/2004 | Zhong et al. |
| 2004/0142382 A1 | 7/2004 | Veldman et al. |
| 2004/0208873 A1 | 10/2004 | Teeling et al. |
| 2004/0236080 A1 | 11/2004 | Aburatani et al. |
| 2005/0014934 A1 | 1/2005 | Hinton et al. |
| 2005/0032114 A1 | 2/2005 | Hinton et al. |
| 2005/0054832 A1 | 3/2005 | Lazar et al. |
| 2005/0064514 A1 | 3/2005 | Stavenhagen et al. |
| 2005/0095243 A1 | 5/2005 | Chan et al. |
| 2005/0244403 A1 | 11/2005 | Lazar et al. |
| 2005/0260213 A1 | 11/2005 | Koenig et al. |
| 2005/0260711 A1 | 11/2005 | Datta et al. |
| 2005/0261229 A1 | 11/2005 | Gillies et al. |
| 2006/0014156 A1 | 1/2006 | Rabbani et al. |
| 2006/0019342 A1 | 1/2006 | Dall'Acqua et al. |
| 2006/0024298 A1 | 2/2006 | Lazar et al. |
| 2006/0057149 A1 | 3/2006 | Johnson et al. |
| 2006/0063228 A1 | 3/2006 | Kasaian et al. |
| 2006/0141456 A1 | 6/2006 | Edwards et al. |
| 2006/0153860 A1 | 7/2006 | Cho et al. |
| 2006/0194291 A1 | 8/2006 | Presta |
| 2006/0198840 A1 | 9/2006 | Dall'Acqua et al. |
| 2007/0003546 A1 | 1/2007 | Lazar et al. |
| 2007/0009523 A1 | 1/2007 | Presta |
| 2007/0036785 A1 | 2/2007 | Kishimoto et al. |
| 2007/0037734 A1 | 2/2007 | Rossi et al. |
| 2007/0041978 A1 | 2/2007 | Hattori et al. |
| 2007/0059312 A1 | 3/2007 | Baca et al. |
| 2007/0135620 A1 | 6/2007 | Chamberlain et al. |
| 2007/0148164 A1 | 6/2007 | Farrington et al. |
| 2007/0160598 A1 | 7/2007 | Dennis et al. |
| 2007/0190056 A1 | 8/2007 | Kambadur et al. |
| 2007/0231329 A1 | 10/2007 | Lazar et al. |
| 2007/0248602 A1 | 10/2007 | Lazar et al. |
| 2007/0269371 A1 | 11/2007 | Krummen et al. |
| 2008/0044417 A1 | 2/2008 | Johnson et al. |
| 2008/0050370 A1 | 2/2008 | Glaser et al. |
| 2008/0138349 A1 | 6/2008 | Stavenhagen et al. |
| 2008/0166756 A1 | 7/2008 | Tsuchiya et al. |
| 2008/0181890 A1 | 7/2008 | Lazar et al. |
| 2008/0199471 A1 | 8/2008 | Bernett et al. |
| 2008/0206867 A1 | 8/2008 | Desjarlais et al. |
| 2008/0274506 A1 | 11/2008 | Presta |
| 2009/0035836 A1 | 2/2009 | Datta et al. |
| 2009/0041770 A1 | 2/2009 | Chamberlain et al. |
| 2009/0053211 A9 | 2/2009 | Lazar et al. |
| 2009/0053240 A1 | 2/2009 | Lazar et al. |
| 2009/0076251 A1 | 3/2009 | Koenig et al. |
| 2009/0130110 A1 | 5/2009 | Babcook et al. |
| 2009/0136485 A1 | 5/2009 | Chu et al. |
| 2009/0263392 A1 | 10/2009 | Igawa et al. |

(56) References Cited

U.S. PATENT DOCUMENTS

| | | |
|---|---|---|
| 2009/0324589 A1 | 12/2009 | Igawa et al. |
| 2010/0098710 A1 | 4/2010 | Hariharan et al. |
| 2010/0098730 A1 | 4/2010 | Lowman et al. |
| 2010/0099147 A1 | 4/2010 | Hariharan et al. |
| 2010/0129365 A1 | 5/2010 | Kim et al. |
| 2010/0184959 A1 | 7/2010 | Guler-Gane et al. |
| 2010/0216187 A1 | 8/2010 | Lasters et al. |
| 2010/0239577 A1 | 9/2010 | Igawa et al. |
| 2010/0249482 A1 | 9/2010 | Chung et al. |
| 2010/0292443 A1 | 11/2010 | Sabbadini et al. |
| 2010/0298542 A1 | 11/2010 | Igawa et al. |
| 2011/0021755 A1 | 1/2011 | Lazar et al. |
| 2011/0027276 A1 | 2/2011 | Bernett et al. |
| 2011/0044986 A1 | 2/2011 | Biere-Citron et al. |
| 2011/0059093 A1 | 3/2011 | Bohrmann et al. |
| 2011/0076275 A1 | 3/2011 | Igawa et al. |
| 2011/0098450 A1 | 4/2011 | Igawa et al. |
| 2011/0105724 A1 | 5/2011 | Clegg et al. |
| 2011/0111406 A1 | 5/2011 | Igawa et al. |
| 2011/0135662 A1 | 6/2011 | Finney et al. |
| 2011/0150888 A1 | 6/2011 | Foltz et al. |
| 2011/0223658 A1 | 9/2011 | Beliard et al. |
| 2011/0229489 A1 | 9/2011 | Pons et al. |
| 2011/0245473 A1 | 10/2011 | Igawa et al. |
| 2011/0311454 A1 | 12/2011 | Dall'Acqua et al. |
| 2012/0028304 A1 | 2/2012 | Dahiyat et al. |
| 2012/0093818 A1 | 4/2012 | Jackson et al. |
| 2012/0189639 A1 | 7/2012 | Schebye et al. |
| 2012/0301488 A1 | 11/2012 | Zhang et al. |
| 2013/0011866 A1 | 1/2013 | Igawa et al. |
| 2013/0085074 A1 | 4/2013 | Walker et al. |
| 2013/0085265 A1 | 4/2013 | Jackson et al. |
| 2013/0131319 A1 | 5/2013 | Igawa et al. |
| 2013/0142788 A1 | 6/2013 | Ashman et al. |
| 2013/0209457 A1 | 8/2013 | Lazar et al. |
| 2013/0209489 A1 | 8/2013 | Han et al. |
| 2013/0247234 A1 | 9/2013 | McWhirter et al. |
| 2013/0259876 A1 | 10/2013 | Murphy et al. |
| 2013/0302315 A1 | 11/2013 | Lazar et al. |
| 2013/0302399 A1 | 11/2013 | Feldhaus et al. |
| 2013/0303396 A1 | 11/2013 | Igawa et al. |
| 2013/0336963 A1 | 12/2013 | Igawa et al. |
| 2014/0044730 A1 | 2/2014 | Yancopoulos et al. |
| 2014/0073768 A1 | 3/2014 | Lazar et al. |
| 2014/0082760 A1 | 3/2014 | Mcwhirter et al. |
| 2014/0093496 A1 | 4/2014 | Mimoto et al. |
| 2014/0105889 A1 | 4/2014 | Igawa et al. |
| 2014/0127209 A1 | 5/2014 | Grabstein et al. |
| 2014/0199294 A1 | 7/2014 | Mimoto et al. |
| 2014/0227292 A1 | 8/2014 | Flanagan et al. |
| 2014/0234340 A1 | 8/2014 | Igawa et al. |
| 2014/0249297 A1 | 9/2014 | Lazar et al. |
| 2014/0271459 A1 | 9/2014 | Dutzar et al. |
| 2014/0294833 A1 | 10/2014 | Desjarlais et al. |
| 2014/0335089 A1 | 11/2014 | Igawa et al. |
| 2014/0356371 A1 | 12/2014 | Swergold et al. |
| 2014/0363426 A1 | 12/2014 | Moore et al. |
| 2014/0363428 A1 | 12/2014 | Igawa et al. |
| 2015/0050269 A1 | 2/2015 | Igawa et al. |
| 2015/0056182 A1 | 2/2015 | Igawa et al. |
| 2015/0079088 A1 | 3/2015 | Lowman et al. |
| 2015/0166636 A1 | 6/2015 | Igawa et al. |
| 2015/0166654 A1 | 6/2015 | Igawa et al. |
| 2015/0203577 A1 | 7/2015 | Igawa et al. |
| 2015/0210763 A1 | 7/2015 | Kuramochi et al. |
| 2015/0252107 A1 | 9/2015 | Stevis et al. |
| 2015/0284465 A1 | 10/2015 | Igawa et al. |
| 2015/0299296 A1 | 10/2015 | Katada et al. |
| 2015/0299313 A1 | 10/2015 | Igawa et al. |
| 2015/0315278 A1 | 11/2015 | Igawa et al. |
| 2015/0344570 A1 | 12/2015 | Igawa et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0176954 A1 | 6/2016 | Ruike et al. |
| 2016/0200807 A1 | 7/2016 | Ruike et al. |
| 2016/0229908 A1 | 8/2016 | Igawa et al. |
| 2016/0244526 A1 | 8/2016 | Igawa et al. |
| 2017/0002080 A1 | 1/2017 | Igawa et al. |
| 2017/0022270 A1 | 1/2017 | Igawa et al. |
| 2017/0174778 A1 | 6/2017 | Shusta et al. |
| 2017/0181987 A1 | 6/2017 | Svensson et al. |
| 2018/0002415 A1 | 1/2018 | Ruike et al. |
| 2018/0016327 A1 | 1/2018 | Murata et al. |
| 2018/0142027 A1 | 5/2018 | Igawa et al. |
| 2018/0258161 A1 | 9/2018 | Igawa et al. |
| 2018/0258163 A1 | 9/2018 | Igawa et al. |
| 2018/0282718 A1 | 10/2018 | Igawa et al. |
| 2018/0282719 A1 | 10/2018 | Igawa et al. |
| 2018/0319876 A1 | 11/2018 | Ruike et al. |
| 2018/0319877 A1 | 11/2018 | Ruike et al. |
| 2019/0002548 A1 | 1/2019 | Ruike et al. |
| 2019/0062413 A1 | 2/2019 | Ruike et al. |
| 2019/0112393 A1 | 4/2019 | Igawa et al. |
| 2019/0169286 A1 | 6/2019 | Kakiuchi et al. |
| 2019/0218309 A1 | 7/2019 | Igawa et al. |
| 2019/0367599 A1 | 12/2019 | Shinomiya et al. |
| 2020/0031913 A1 | 1/2020 | Ruike et al. |
| 2020/0048627 A1 | 2/2020 | Igawa et al. |
| 2020/0317768 A1 | 10/2020 | Ruike et al. |
| 2020/0407432 A1 | 12/2020 | Shinomiya et al. |
| 2021/0301004 A1 | 9/2021 | Shinomiya et al. |
| 2021/0324109 A1 | 10/2021 | Igawa et al. |
| 2022/0089715 A1 | 3/2022 | Igawa et al. |
| 2022/0213140 A1 | 7/2022 | Wakabayashi et al. |
| 2022/0389105 A1 | 12/2022 | Igawa et al. |
| 2022/0389118 A1 | 12/2022 | Igawa et al. |
| 2022/0411483 A1 | 12/2022 | Mimoto et al. |
| 2023/0140797 A1 | 5/2023 | Igawa et al. |
| 2023/0174655 A1 | 6/2023 | Mimoto et al. |
| 2023/0203144 A1 | 6/2023 | Murata et al. |
| 2023/0250162 A1 | 8/2023 | Shinomiya et al. |
| 2024/0002836 A1 | 1/2024 | Igawa et al. |
| 2024/0052021 A1 | 2/2024 | Ruike et al. |

FOREIGN PATENT DOCUMENTS

| | | |
|---|---|---|
| AU | 2012222252 A1 | 10/2013 |
| AU | 2014250434 A1 | 10/2015 |
| AU | 2015227424 A1 | 10/2015 |
| AU | 2012222252 B2 | 8/2016 |
| BR | 112017006736 A2 | 12/2017 |
| CA | 2647846 A1 | 10/2007 |
| CA | 2911000 A1 | 10/2007 |
| CA | 2700986 A1 | 4/2009 |
| CA | 2827923 A1 | 8/2012 |
| CN | 1156460 A | 8/1997 |
| CN | 1274289 A | 11/2000 |
| CN | 1763097 A | 4/2006 |
| CN | 101001873 A | 7/2007 |
| CN | 101230102 A | 7/2008 |
| CN | 101277976 A | 10/2008 |
| CN | 101282992 A | 10/2008 |
| CN | 100455598 C | 1/2009 |
| CN | 101479381 A | 7/2009 |
| CN | 101511871 A | 8/2009 |
| CN | 101874042 A | 10/2010 |
| CN | 101014619 B | 11/2010 |
| CN | 101932593 A | 12/2010 |
| CN | 1763097 B | 4/2011 |
| CN | 102149729 A | 8/2011 |
| CN | 102325793 A | 1/2012 |
| CN | 101277976 B | 4/2012 |
| CN | 101511871 B | 7/2012 |
| CN | 102633880 A | 8/2012 |
| CN | 101282992 B | 2/2013 |
| CN | 102918057 A | 2/2013 |
| CN | 101001873 B | 3/2013 |
| CN | 102993304 A | 3/2013 |
| CN | 103097415 A | 5/2013 |
| CN | 103221426 A | 7/2013 |
| CN | 103492565 A | 1/2014 |
| CN | 103975060 A | 8/2014 |
| CN | 102633880 B | 2/2015 |

(56) References Cited

FOREIGN PATENT DOCUMENTS

| | | |
|---|---|---|
| CN | 103221426 B | 1/2016 |
| CN | 107108726 A | 8/2017 |
| CN | 101874042 B | 9/2018 |
| EA | 004317 B1 | 2/2004 |
| EA | 15589 B1 | 10/2011 |
| EP | 0182495 A | 5/1986 |
| EP | 0329185 A2 | 8/1989 |
| EP | 0329185 B1 | 4/1994 |
| EP | 0770628 A1 | 5/1997 |
| EP | 0783893 A1 | 7/1997 |
| EP | 1069185 A1 | 1/2001 |
| EP | 1509770 A1 | 3/2005 |
| EP | 1601697 A1 | 12/2005 |
| EP | 0770628 B1 | 9/2006 |
| EP | 1773391 A2 | 4/2007 |
| EP | 1601697 B1 | 5/2007 |
| EP | 1870459 A1 | 12/2007 |
| EP | 1992692 A1 | 11/2008 |
| EP | 2006381 A1 | 12/2008 |
| EP | 2009101 A1 | 12/2008 |
| EP | 2196541 A | 6/2010 |
| EP | 2202245 A | 6/2010 |
| EP | 2275443 A1 | 1/2011 |
| EP | 1069185 B1 | 6/2011 |
| EP | 2368911 A1 | 9/2011 |
| EP | 2409990 A1 | 1/2012 |
| EP | 2431393 A | 3/2012 |
| EP | 783893 B1 | 4/2012 |
| EP | 2471813 A1 | 7/2012 |
| EP | 1992692 B1 | 1/2013 |
| EP | 2647706 A1 | 10/2013 |
| EP | 2679681 A | 1/2014 |
| EP | 2698431 A1 | 2/2014 |
| EP | 2760890 A2 | 8/2014 |
| EP | 2762166 A1 | 8/2014 |
| EP | 2762493 A1 | 8/2014 |
| EP | 2762564 A1 | 8/2014 |
| EP | 2765192 A1 | 8/2014 |
| EP | 2818183 A1 | 12/2014 |
| EP | 2853898 A1 | 4/2015 |
| EP | 2889377 A | 7/2015 |
| EP | 2940043 A1 | 11/2015 |
| EP | 2275443 B1 | 12/2015 |
| EP | 1870459 B1 | 6/2016 |
| EP | 3042912 A1 | 7/2016 |
| EP | 3240804 A | 11/2017 |
| JP | S61117457 A | 6/1986 |
| JP | H0228200 A | 1/1990 |
| JP | H03500644 A | 2/1991 |
| JP | H03504332 A | 9/1991 |
| JP | H0441000 B | 7/1992 |
| JP | H05504579 A | 7/1993 |
| JP | H0767688 A | 3/1995 |
| JP | H08217799 A | 8/1996 |
| JP | 2638680 B2 | 8/1997 |
| JP | 2003512019 A | 4/2003 |
| JP | 200473210 A | 3/2004 |
| JP | 2004511426 A | 4/2004 |
| JP | 2005501514 A | 1/2005 |
| JP | 2005510212 A | 4/2005 |
| JP | 2005535341 A | 11/2005 |
| JP | 2006512407 A | 4/2006 |
| JP | 2006517525 A | 7/2006 |
| JP | 2006519583 A | 8/2006 |
| JP | 3865418 B2 | 10/2006 |
| JP | 2007252368 A | 10/2007 |
| JP | 2007532139 A | 11/2007 |
| JP | 2008505174 A | 2/2008 |
| JP | 4179517 B2 | 11/2008 |
| JP | 2009511067 A | 3/2009 |
| JP | 2009541352 A | 11/2009 |
| JP | 2010505436 A | 2/2010 |
| JP | 2010081866 A | 4/2010 |
| JP | 2010514460 A | 5/2010 |
| JP | 4547561 B2 | 9/2010 |
| JP | 4580340 B2 | 11/2010 |
| JP | 2011504096 A | 2/2011 |
| JP | 4886986 B | 2/2012 |
| JP | 2012512641 A | 6/2012 |
| JP | 5055603 B2 | 10/2012 |
| JP | 2013518131 A | 5/2013 |
| JP | 2013518606 A | 5/2013 |
| JP | 5229888 B2 | 7/2013 |
| JP | 2013531486 A | 8/2013 |
| JP | 2013537425 A | 10/2013 |
| JP | 5334319 B | 11/2013 |
| JP | 5357778 B2 | 12/2013 |
| JP | 5367982 B | 12/2013 |
| JP | 5421105 B2 | 2/2014 |
| JP | 2014055145 A | 3/2014 |
| JP | 5756291 B2 | 7/2015 |
| JP | 2015130883 A | 7/2015 |
| JP | 5882247 B2 | 2/2016 |
| JP | 2016026190 A | 2/2016 |
| JP | 6082447 B | 2/2017 |
| KR | 100261941 B1 | 7/2000 |
| KR | 20100074220 A | 7/2010 |
| KR | 20110004435 A | 1/2011 |
| KR | 20110103431 A | 9/2011 |
| KR | 20120035192 A | 4/2012 |
| KR | 101282320 B1 | 7/2013 |
| KR | 20140005864 A | 1/2014 |
| KR | 20140069332 A | 6/2014 |
| KR | 101575914 B1 | 12/2015 |
| MX | 2013006109 A | 1/2014 |
| RU | 2147442 C | 4/2000 |
| RU | 2225721 C | 3/2004 |
| RU | 2236222 C | 9/2004 |
| RU | 2266298 C | 12/2005 |
| RU | 2005112742 A | 1/2006 |
| RU | 2325186 C2 | 5/2008 |
| RU | 2337107 C2 | 10/2008 |
| RU | 2360925 C | 7/2009 |
| RU | 2008104038 A | 8/2009 |
| RU | 2390527 C | 5/2010 |
| RU | 2009112723 A | 10/2010 |
| RU | 2422460 C2 | 6/2011 |
| RU | 2430111 C | 9/2011 |
| RU | 2010116152 A | 11/2011 |
| RU | 2505603 C | 1/2014 |
| RU | 2519645 C | 6/2014 |
| SG | 192945 A | 9/2013 |
| TW | 416960 B | 1/2001 |
| TW | 201202419 A | 1/2012 |
| TW | 201643190 A | 12/2016 |
| TW | 201712032 A | 4/2017 |
| TW | I605057 B | 11/2017 |
| TW | 201808331 A | 3/2018 |
| TW | 201808992 A | 3/2018 |
| TW | I621628 B | 4/2018 |
| TW | 201819409 A | 6/2018 |
| TW | I656133 B | 4/2019 |
| TW | 202039553 A | 11/2020 |
| WO | WO-8303678 A1 | 10/1983 |
| WO | WO-8901343 A1 | 2/1989 |
| WO | WO-9007524 A1 | 7/1990 |
| WO | WO-9112023 A2 | 8/1991 |
| WO | WO-9113631 A1 | 9/1991 |
| WO | WO9207084 A1 | 4/1992 |
| WO | WO-9219759 A1 | 11/1992 |
| WO | WO-9317105 A1 | 9/1993 |
| WO | WO-9421681 A1 | 9/1994 |
| WO | WO-9514710 A1 | 6/1995 |
| WO | WO-9602576 A1 | 2/1996 |
| WO | WO-9611020 A1 | 4/1996 |
| WO | WO-9612503 A1 | 5/1996 |
| WO | WO-9720858 A1 | 6/1997 |
| WO | WO-9734631 A1 | 9/1997 |
| WO | WO-9803546 A1 | 1/1998 |
| WO | WO-9805787 A1 | 2/1998 |
| WO | WO-9846257 A1 | 10/1998 |
| WO | WO-9918212 A1 | 4/1999 |
| WO | WO-9951642 A1 | 10/1999 |
| WO | WO-9951743 A1 | 10/1999 |

(56) References Cited

FOREIGN PATENT DOCUMENTS

| | | |
|---|---|---|
| WO | WO-9958572 A1 | 11/1999 |
| WO | WO-0014220 A1 | 3/2000 |
| WO | WO-0015214 A1 | 3/2000 |
| WO | WO-0042072 A2 | 7/2000 |
| WO | WO-0130854 A2 | 5/2001 |
| WO | WO0170968 A2 | 9/2001 |
| WO | WO-0182899 A2 | 11/2001 |
| WO | WO-0209641 A2 | 2/2002 |
| WO | WO-02060919 A2 | 8/2002 |
| WO | WO-03000883 A1 | 1/2003 |
| WO | WO-03020949 A2 | 3/2003 |
| WO | WO-03027248 A2 | 4/2003 |
| WO | WO-03070760 A2 | 8/2003 |
| WO | WO-03074679 A2 | 9/2003 |
| WO | WO-03105757 A2 | 12/2003 |
| WO | WO-03107009 A2 | 12/2003 |
| WO | WO-2004016740 A2 | 2/2004 |
| WO | WO-2004024890 A2 | 3/2004 |
| WO | WO-2004029207 A2 | 4/2004 |
| WO | WO-2004037861 A2 * | 5/2004 ............ C07K 16/22 |
| WO | WO-2004039826 A1 | 5/2004 |
| WO | WO-2004058797 A2 | 7/2004 |
| WO | WO-2004068931 A2 | 8/2004 |
| WO | WO-2004096273 A1 | 11/2004 |
| WO | WO-2004099249 A2 | 11/2004 |
| WO | WO-2004108157 A2 | 12/2004 |
| WO | WO-2005023193 A2 | 3/2005 |
| WO | WO-2005035756 A1 | 4/2005 |
| WO | WO-2005047307 A2 | 5/2005 |
| WO | WO-2005047327 A2 | 5/2005 |
| WO | WO-2005056606 A2 | 6/2005 |
| WO | WO-2005056759 A2 | 6/2005 |
| WO | WO-2005059106 A2 | 6/2005 |
| WO | WO-2005066204 A2 | 7/2005 |
| WO | WO-2005067620 A2 | 7/2005 |
| WO | WO-2005077981 A2 | 8/2005 |
| WO | WO-2005080429 A2 | 9/2005 |
| WO | WO-2005092925 A2 | 10/2005 |
| WO | WO-2005094446 A2 | 10/2005 |
| WO | WO-2005112564 A2 | 12/2005 |
| WO | WO-2005115452 A2 | 12/2005 |
| WO | WO-2005121180 A1 | 12/2005 |
| WO | WO-2005123126 A2 | 12/2005 |
| WO | WO-2006004663 A2 | 1/2006 |
| WO | WO-2006019447 A1 | 2/2006 |
| WO | WO-2006020114 A2 | 2/2006 |
| WO | WO-2006023403 A2 | 3/2006 |
| WO | WO-2006023420 A2 | 3/2006 |
| WO | WO-2006030200 A1 | 3/2006 |
| WO | WO-2006030220 A1 | 3/2006 |
| WO | WO-2006031370 A2 | 3/2006 |
| WO | WO-2006047350 A2 | 5/2006 |
| WO | WO-2006050166 A2 | 5/2006 |
| WO | WO-2006050491 A2 | 5/2006 |
| WO | WO-2006053301 A2 | 5/2006 |
| WO | WO-2006066598 A2 | 6/2006 |
| WO | WO-2006067913 A1 | 6/2006 |
| WO | WO-2006071877 A2 | 7/2006 |
| WO | WO-2006076594 A2 | 7/2006 |
| WO | WO-2006082052 A1 | 8/2006 |
| WO | WO-2006083182 A1 | 8/2006 |
| WO | WO-2006083183 A1 | 8/2006 |
| WO | WO-2006085967 A2 | 8/2006 |
| WO | WO-2006102095 A2 | 9/2006 |
| WO | WO-2006105338 A2 | 10/2006 |
| WO | WO-2006106905 A1 | 10/2006 |
| WO | WO-2006109592 A1 | 10/2006 |
| WO | WO-2006113643 A2 | 10/2006 |
| WO | WO-2006116269 A2 | 11/2006 |
| WO | WO-2006121852 A2 | 11/2006 |
| WO | WO-2006130834 A2 | 12/2006 |
| WO | WO-2007001422 A2 | 1/2007 |
| WO | WO-2007008943 A2 | 1/2007 |
| WO | WO-2007022520 A2 | 2/2007 |
| WO | WO-2007024249 A2 | 3/2007 |
| WO | WO-2007024535 A2 | 3/2007 |
| WO | WO-2007041635 A2 | 4/2007 |
| WO | WO-2007044411 A2 | 4/2007 |
| WO | WO-2007044616 A2 | 4/2007 |
| WO | WO-2007047112 A2 | 4/2007 |
| WO | WO-2007047578 A2 | 4/2007 |
| WO | WO-2007060411 A1 | 5/2007 |
| WO | WO-2007076524 A2 | 7/2007 |
| WO | WO-2007084253 A2 | 7/2007 |
| WO | WO-2007092772 A2 | 8/2007 |
| WO | WO-2007114319 A1 | 10/2007 |
| WO | WO-2007114325 A1 | 10/2007 |
| WO | WO-2007142325 A1 | 12/2007 |
| WO | WO-2007150015 A2 | 12/2007 |
| WO | WO-2007150016 A2 | 12/2007 |
| WO | WO-2008002933 A2 | 1/2008 |
| WO | WO-2008017963 A2 | 2/2008 |
| WO | WO-2008022152 A2 | 2/2008 |
| WO | WO-2008030706 A2 | 3/2008 |
| WO | WO-2008031056 A2 | 3/2008 |
| WO | WO-2008036688 A2 | 3/2008 |
| WO | WO-2008043822 A2 | 4/2008 |
| WO | WO-2008060785 A2 | 5/2008 |
| WO | WO-2008091798 A2 | 7/2008 |
| WO | WO-2008091954 A2 | 7/2008 |
| WO | WO-2008092117 A2 | 7/2008 |
| WO | WO-2008098115 A2 | 8/2008 |
| WO | WO-2008121160 A2 | 10/2008 |
| WO | WO-2008130969 A2 | 10/2008 |
| WO | WO-2008150494 A1 | 12/2008 |
| WO | WO-2009000098 A2 | 12/2008 |
| WO | WO-2009000099 A2 | 12/2008 |
| WO | WO-2009006338 A1 | 1/2009 |
| WO | WO-2009026117 A2 | 2/2009 |
| WO | WO-2009032145 A1 | 3/2009 |
| WO | WO-2009032782 A2 | 3/2009 |
| WO | WO-2009041062 A1 | 4/2009 |
| WO | WO-2009041643 A1 | 4/2009 |
| WO | WO-2009058346 A1 | 5/2009 |
| WO | WO-2009058492 A2 | 5/2009 |
| WO | WO-2009062083 A2 | 5/2009 |
| WO | WO-2009086320 A1 | 7/2009 |
| WO | WO-2009095235 A1 | 8/2009 |
| WO | WO-2009125825 A1 | 10/2009 |
| WO | WO-2009131702 A2 | 10/2009 |
| WO | WO-2009137880 A1 | 11/2009 |
| WO | WO-2009139822 A1 | 11/2009 |
| WO | WO-2009155513 A2 | 12/2009 |
| WO | WO-2010033736 A1 | 3/2010 |
| WO | WO-2010045193 A1 | 4/2010 |
| WO | WO-2010058860 A1 | 5/2010 |
| WO | WO-2010070094 A1 | 6/2010 |
| WO | WO-2010077854 A1 | 7/2010 |
| WO | WO-2010107109 A1 | 9/2010 |
| WO | WO-2010151338 A2 | 12/2010 |
| WO | WO-2011008517 A2 | 1/2011 |
| WO | WO-2011021009 A1 | 2/2011 |
| WO | WO-2011091078 A2 | 7/2011 |
| WO | WO-2011094593 A2 | 8/2011 |
| WO | WO-2011100271 A2 | 8/2011 |
| WO | WO-2011111007 A2 | 9/2011 |
| WO | WO-2011122011 A2 | 10/2011 |
| WO | WO-2011150008 A1 | 12/2011 |
| WO | WO-2011151432 A1 | 12/2011 |
| WO | WO-2012016227 A2 | 2/2012 |
| WO | WO-2012024242 A1 | 2/2012 |
| WO | WO-2012044831 A1 | 4/2012 |
| WO | WO-2012073992 A1 | 6/2012 |
| WO | WO-2012093704 A1 | 7/2012 |
| WO | WO-2012115241 A1 | 8/2012 |
| WO | WO-2012132067 A1 | 10/2012 |
| WO | WO-2012133782 A1 | 10/2012 |
| WO | WO-2012151481 A1 | 11/2012 |
| WO | WO-2013012733 A1 | 1/2013 |
| WO | WO-2013046704 A2 | 4/2013 |
| WO | WO-2013046722 A1 | 4/2013 |
| WO | WO-2013047729 A1 | 4/2013 |
| WO | WO-2013047748 A1 | 4/2013 |
| WO | WO-2013047752 A1 | 4/2013 |

(56) References Cited

FOREIGN PATENT DOCUMENTS

| | | |
|---|---|---|
| WO | WO-2013081143 A1 | 6/2013 |
| WO | WO-2013125667 A1 | 8/2013 |
| WO | WO-2013138680 A1 | 9/2013 |
| WO | WO-2013138681 A1 | 9/2013 |
| WO | WO-2013152001 A2 | 10/2013 |
| WO | WO-2013166099 A1 | 11/2013 |
| WO | WO-2013180200 A1 | 12/2013 |
| WO | WO-2013186719 A1 | 12/2013 |
| WO | WO-2014006217 A1 | 1/2014 |
| WO | WO-2014028354 A1 | 2/2014 |
| WO | WO-2014030728 A1 | 2/2014 |
| WO | WO-2014030750 A1 | 2/2014 |
| WO | WO-2014043344 A1 | 3/2014 |
| WO | WO-2014074532 A2 | 5/2014 |
| WO | WO-2014100689 A1 | 6/2014 |
| WO | WO-2014114651 A1 | 7/2014 |
| WO | WO-2014140366 A1 | 9/2014 |
| WO | WO-2014144080 A2 | 9/2014 |
| WO | WO-2014144575 A1 | 9/2014 |
| WO | WO-2014144577 A1 | 9/2014 |
| WO | WO-2014144903 A1 | 9/2014 |
| WO | WO-2014145159 A2 | 9/2014 |
| WO | WO-2014145806 A2 | 9/2014 |
| WO | WO-2014150983 A2 | 9/2014 |
| WO | WO-2014163101 A1 | 10/2014 |
| WO | WO-2014164959 A2 | 10/2014 |
| WO | WO-2014182676 A2 | 11/2014 |
| WO | WO-2014184384 A1 | 11/2014 |
| WO | WO-2014190441 A1 | 12/2014 |
| WO | WO-2015022658 A2 | 2/2015 |
| WO | WO2015034000 A1 | 3/2015 |
| WO | WO-2015042250 A1 | 3/2015 |
| WO | WO-2015077491 A1 | 5/2015 |
| WO | WO-2015111008 A2 | 7/2015 |
| WO | WO-2015134894 A1 | 9/2015 |
| WO | WO-2015162590 A1 | 10/2015 |
| WO | WO-2016073853 A1 | 5/2016 |
| WO | WO-2016073906 A2 | 5/2016 |
| WO | WO-2016092439 A1 | 6/2016 |
| WO | WO-2016098356 A1 | 6/2016 |
| WO | WO-2016098357 A1 | 6/2016 |
| WO | WO2016117346 A1 | 7/2016 |
| WO | WO-2016125495 A1 | 8/2016 |
| WO | WO-2016168613 A1 | 10/2016 |
| WO | WO-2017046994 A1 | 3/2017 |
| WO | WO-2017049011 A1 | 3/2017 |
| WO | WO2017104779 A1 | 6/2017 |
| WO | WO-2017104783 A1 | 6/2017 |
| WO | WO2017110981 A1 | 6/2017 |
| WO | WO-2017120523 A1 | 7/2017 |
| WO | WO2017217524 A1 | 12/2017 |
| WO | WO-2017217525 A1 | 12/2017 |
| WO | WO-2017218592 A1 | 12/2017 |
| WO | WO-2018025982 A1 | 2/2018 |
| WO | WO2018143266 A1 | 8/2018 |
| WO | WO-2018167322 A1 | 9/2018 |
| WO | WO-2018169993 A1 | 9/2018 |
| WO | WO2020027279 A1 | 2/2020 |
| WO | WO2020209318 A1 | 10/2020 |

OTHER PUBLICATIONS

Aboud-Pirak, E., et al., "Binding and Endocytosis of a Monoclonal Antibody to a High Molecular Weight Human Milk Fat Globule Membrane-associated Antigen by Cultured MCF-7 Breast Carcinoma Cells," Cancer Res., 48:3188-3196 (1988). Boud-Pirak.
Adams, C. W., et al., "Humanization of a recombinant monoclonal antibody to produce a therapeutic HER dimerization inhibitor, pertuzumab," Cancer Immunol Immunother., 55:717-727 (2006).
Algonomics—TripoleR applications [Online] Retrieved from the Internet on Feb. 29, 2012, http://www.algonomics.com/proteinengineering/tripole_applications.php, 2 pages (Feb. 21, 2009).
Almagro, J.C. and Fransson, J., "Humanization of Antibodies," Frontiers in Bioscience 13:1619-1633, Frontiers In Bioscience Publications, United States (2008).
Affinity Chromatography, Principles and Methods, Amersham Biosciences, 16-18 (2002).
Amersham Biosciences. Antibody Purification Handbook, Edition 18-1037-46, Amersham Biosciences AB (2002).
Amigorena, S., et al., "FcγRII expression in resting and activated B lymphocytes," Eur J Immunol., 19:1379-1385 (1989).
Amigorena, S., et al., "Cytoplasmic Domain Heterogeneity and Functions of IgG Fc Receptors in B Lymphocytes," Science, 256:1808-1812 (1992.
Arici, A., "Local Cytokines in Endometrial Tissue: The Role of Interleukin-8 in the Pathogenesis of Endometriosis," Ann N Y Acad Sci., 955:101-9; discussion 118, 396-406 (2002).
Armour, K.L., et al., "Recombinant human IgG molecules lacking Fcγ receptor I binding and monocyte triggering activities," Eur J Immunol 29(8):2613-2624 (1999).
Armour, K. L., "Differential binding to human FcγRIIa and FcγRIIb receptors by human IgG wildtype and mutant antibodies," Mol Immunol., 40:585-593 (2003).
Balint, R. F. and Larrick, J. W., "Antibody engineering by parsimonious mutagenesis," Gene 137:109-118 (1993).
Barrabes, S., et al., "Effect of sialic acid content on glycoprotein p/ analyzed by two-dimensional electrophoresis," Electrophoresis, 31:2903-2912 (2010).
Bartelsd, G. M., et al., "Clinical response to adalimumab: relationship to anti-adalimumab antibodies and serum adalimumab concentrations in rheumatoid arthritis," Ann Rheum Dis 66:921-926 (2007).
Batra, S.K., et al., "Pharmacokinetics and Biodistribution of Genetically Engineered Antibodies," Current Opinion in Biotechnology 13(6):603-608 (2002).
Bayry, J., et al., "Immuno affinity purification of foot and mouth disease virus type specific antibodies using recombinant protein adsorbed to polystyrene wells," J Virol Meth 81:21-30 (1999).
Beck, A., et al., "Strategies and challenges for the next generation of therapeutic antibodies," Nat Rev Immunol 10:345-352 (2010).
Becker, J. M., et al., "Prevention of Postoperative Abdominal Adhesions by a Sodium Hyaluronate-Based Bioresorbable Membrane: A Prospective, Randomized, Double-Blind Multicenter Study," J Am Coll Surg 183:297-306 (1996).
Bender, N. K., et al., "Immunogenecity, efficacy and adverse events of adalimumab in RA patients," Rheumatol Int., 27:269-274 (2007).
Biacore GE Healthcare, "Sensor Surface Handbook," pp. 1-100, 2005-2007 (2007).
Binz, H. K., et al., "Engineering novel binding proteins from nonimmunoglobulin domains," Nat Biotechnol 23(10):1257-1268 (2005).
Blank, M. C., et al., "Decreased transcription of the human FCGR2B gene mediated by the—343 G/C promoter polymorphism and association with systemic lupus erythematosus," Hum Genet., 117:220-227 (2005).
Bogdanovich, S., et al., "Functional improvement of dystrophic muscle by myostatin blockade," Nature 420:418-421 (2002).
Bonvin, P., et al., "De novo isolation of antibodies with pH-dependent binding properties," mAbs, 7(2):294-302 (2015).
Borrok, M.J., et al., "pH-Dependent Binding Engineering Reveals an FcRn Affinity Threshold That Governs IgG Recycling," J Biol Chem. 290(7):4282-4290 (2015).
Boruchov, A. M., et al., Activating and inhibitory IgG Fc receptors on human DCs mediate opposing functions, J Clin Invest., 115(10):2914-2923 (2005).
Boumpas, D. T., et al., "A Short Course of BG9588 (Anti-CD40 Ligand Antibody) Improves Serologic Activity and Decreases Hematuria in Patients With Proliferative Lupus Glomerulonephritis," Arth Rheum., 48(3):719-727 (2003).
Breitbart, A., et al., "Highly Specific Detection of Myostatin Prodomain by an Immunoradiometric Sandwich Assay in Serum of Healthy Individuals and Patients," PLOS One, 8(11):e80454 (2013).
Brown, M., et al., "Tolerance to Single, but Not Multiple, Amino Acid Replacements in Antibody $V_H$ CDR2," J Immunol 156:3285-3291 (1996).

(56) References Cited

OTHER PUBLICATIONS

Brown, N. L., et al., "A Study of the Interactions Between an IgG-Binding Domain Based on the B Domain of Staphylococcal Protein A and Rabbit IgG," Mol Biotechnol 10:9-16 (1998).
Bruhns, P., "Properties of mouse and human IgG receptors and their contribution to disease models," Blood, 119(24):5640-5649 (2012).
Bruhns, P., et al., "Specificity and affinity of human Fcγ receptors and their polymorphic variants for human IgG subclasses," Blood, 113:3716-3725 (2009).
Bulun, S. E., "Endometriosis," N Engl J Med 360:268-279 (2009).
Burmeister, W. P., et al., "Crystal structure of the complex of rat neonatal Fc receptor with Fc," Nature, 372:379-383 (1994).
Cartron, G., et al., "Therapeutic activity of humanized anti-CD20 monoclonal antibody and polymorphism in IgG Fc receptor FcγRIIIa gene," Blood, 99:754-758 (2002).
Cemerski, S., et al., "Suppression of mast cell degranulation through a dual-targeting tandem IgE-IgG Fc domain biologic engineered to bind with high affinity to FcγRIIb," Immunol Lett., 143:34-43 (2012).
Certificate of Analysis, "Rabbit Antibody to Human pro-Myostatin (amino acids 79-92)," Meridian Life Science, Inc., Nov. 13, 2015, XP055478289, Catalog No. K24340R, Lot No. 2K31715.
Chang, B. S. and Hershenson, S., "Practical Approaches to Protein Formulation Development," Pharm Biotechnol., 13:1-25 (2002).
Chaparro-Riggers, J., et al., "Increasing Serum Half-life and Extending Cholesterol Lowering in Vivo by Engineering Antibody with pH-sensitive Binding to PCSK9," J Biol Chem 287(14):11090-11097 (2012).
Chau, L. A., et al., "HuM291 (Nuvion), A Humanized Fc Receptor-Nonbinding Antibody Against CD3, Anergizes Peripheral Blood T Cells as Partial Agonist of the T Cell Receptor," Transplantation 71(7):941-950 (2001).
Chen, C., et al., "Generation and Analysis of Random Point Mutations in an Antibody CDR2 Sequence: Many Mutated Antibodies Lose their Ability to Bind Antigen," J Exp Med 176(3):855-866 (1992).
Chen, C., et al., "Defective Secretion of an Immunoglobulin Caused by Mutations in the Heavy Chain Complementarity Determining Region 2," J Exp Med 180(2):577-586 (1994).
Chen, Y., et al., "Selection and Analysis of an Optimized Anti-VEGF Antibody: Crystal Structure of an Affinity-matured Fab in Complex with Antigen," J Mol Biol 293:865-881 (1999).
Chen, C., et al., "Enhancement and destruction of antibody function by somatic mutation: unequal occurrence is controlled by V gene combinatorial associations," The EMBO Journal 14(12):2784-2794 (1995).
Chen, J.-Y., et al., "Association of a Transmembrane Polymorphism of Fcγ Receptor IIb (FCGR2B) With Systemic Lupus Erythematosus in Taiwanese Patients," Arth Rheum., 54(12):3908-3917 (2006).
Chirino, A. J., et al., "Minimizing the immunogenicity of protein therapeutics," DDT 9(2):82-90 (2004).
Chu, G. C., et al., "Accumulation of Succinimide in a Recombinant Monoclonal Antibody in Mildly Acidic Buffers Under Elevated Temperatures," Pharmaceutical Research 24(6):1145-1156 (2007).
Chu, S. Y., et al., "Inhibition of B cell receptor-mediated activation of primary human B cells by coengagement of CD19 and FcγRIIb with Fc-engineered antibodies," Mol Immunol., 45:3926-3933 (2008).
Chu, S. Y., et al., "Reduction of total IgE by targeted coengagement of IgE B-cell receptor and FcγRIIb with Fc-engineered antibody," J Allergy Clin Immunol., 129(4):1102-1115 (2012).
Chuntharapai, A., et al., "Isotype-Dependent Inhibition of Tumor Growth In Vivo by Monoclonal Antibodies to Death Receptor 4," J Immunol, 166:4891-4898 (2001).
Clark, M. R., "IgG Effector Mechanisms," Chem Immunol., 65:88-110 (1997).
Cleland, J. L. and Langer, R., "Drug Delivery from Bioerodible Polymers", Formulation and Delivery of Proteins and Peptides, American Chemical Society, Chapter 15, pp. 242-277 (1994).
Clynes, R., et al., "Fc Receptors Are Required in Passive and Active Immunity to Melanoma," Proc Natl Acad Sci., 95:652-656 (1998).
Clynes, R.A., et al., "Inhibitory Fc receptors modulate in vivo cytotoxicity against tumor targets," Nature Medicine 6(4):443-446 (2000).
Cole, M. S., et al., "Human IgG2 Variants of Chimeric Anti-CD3 Are Nonmitogenic to T Cells," J Immunol., 159:3613-3621 (1997).
Coloma, M. J., et al., "Position Effects of Variable Region Carbohydrate on the Affinity and in Vivo Behavior of an Anti-(1--6) Dextran Antibody," J Immunol., 162(4):2162-2170 (1999).
Comper, W. D. and Glasgow, E. F., "Charge selectivity in kidney ultrafiltration," Kidney Int., 47:1242-1251 (1995).
Cooper, L. J. N., et al., "Variable Domain-Identical Antibodies Exhibit IgG Subclass-Related Differences in Affinity and Kinetic Constants as Determined by Surface Plasmon Resonance," Mol Immunol., 31(8):577-584 (1994).
Cordoba, A. J., et al., "Non-enzymatic hinge region fragmentation of antibodies in solution," J Chromatog B, 818:115-121 (2005).
Couto, J. R., et al., "Anti-BA46 Monoclonal Antibody Mc3: Humanization Using a Novel Positional Consensus and in Vivo and in Vitro Characterization," Cancer Res 55:1717-1722 (1995).
Cruse, J. M. and Lewis, R. E., Atlas of Immunology, CRC Press LLC, excerpt from Chapter 3, p. 109 (2004).
Cuatrecasas, P. and Anfinsen, C. B., "Affinity Chromatography," Methods in Enzymology 22:345-378 (1971).
Dall'Acqua, W. F., et al., "Antibody humanization by framework shuffling," Methods 36:43-60 (2005).
Dall'Acqua, W. F., et al., "Increasing the Affinity of a Human IgG1 for the Neonatal Fc Receptor: Biological Consequences," J Immunol 169:5171-5180 (2002).
Dall'Acqua, W.F., et al., "Properties of Human IgG1s Engineered for Enhanced Binding to the Neonatal Fc Receptor (FcRn)," The Journal of Biological Chemistry 281(33):23514-23524 (2006).
Damschroder, M. M., et al., "Framework shuffling of antibodies to reduce immunogenicity and manipulate functional and biophysical properties," Mol Immunol., 44:3049-3060 (2007).
Data Sheet, "Mouse GDF-8/Myostatin Propeptide Antibody—Antigen Affinity-purified Polyclonal Sheep IgG," R&D Systems, Catalogue No. AF 1539, Feb. 6, 2018, XP055478493.
Data Sheet, "Human Pro-Myostatin (aa 79-92), polyclonal antibody", Immun Diagnostik Antibodies Catalogue No. AK3004.1/AK3004.2, Jun. 30, 2016.
Datta-Mannan, A., et al., "Monoclonal Antibody Clearance—Impact of Modulating the Interaction of IgG With the Neonatal Fc Receptor," J Biol Chem., 282(3):1709-1717 (2007).
Decision of the Opposition Division in EP2275443 dated Apr. 26, 2018.
European Patent Office Decision mailed Jul. 25, 2018 in European Patent Application No. 07 740 474.7, cited in the Ground of Appeal filed Dec. 4, 2018 by Chugai Seiyaku Kabushiki Kaisha in connection with formal Appeal filed Sep. 19, 2018 in European Patent No. 2006381.
Declaration of Madhusudan Natarajan, Ph.D., dated Dec. 19, 2018 by the opponents in Opposition for EP2708558.
Declaration of Dr. Anette Henriksen, dated Apr. 17, 2019, which was submitted by the Opponent during EPO opposition for EP2006381.
Declaration of Dr. Nimish Gera, submitted Sep. 1, 2016 by the opponent in opposition for EP2275443.
De Groot, A. S., et al., "De-immunization of Therapeutic Proteins by T-cell Epitope Modification," Dev Biol 122:171-194 (2005).
De Groot, A.S. and Martin W., et al., "Reducing Risk, Improving Outcomes: Bioengineering Less Immunogenic Protein Therapeutics," Clinical Immunology 131(2):189-201 (2009).
Deen, W. M., et al., "Structural determinants of glomerular permeability," Am J Physiol Renal Physiol., 281:F579-F596 (2001).
Del Rio, G., et al., "An Engineered Penicillin Acylase With Altered Surface Charge Is More Stable in Alkaline pH," Annals of the New York Academy of Sciences, 799:61-64 (1996).
Desai, D.D., et al., "Fc Gamma Receptor IIB on Dendritic Cells Enforces Peripheral Tolerance by Inhibiting Effector T Cell Responses," Journal of Immunology 178(10):6217-6226 (2007).
Devanaboyina, S. C., et al., "The effect of pH dependence of antibody-antigen interactions on subcellular trafficking dynamics," mAbs 5(6):851-859 (2013).

(56) References Cited

OTHER PUBLICATIONS

Dhodapkar, K. M., et al., "Selective blockade of inhibitory Fcγ receptor enables human dendritic cell maturation with IL-12p70 production and immunity to antibody-coated tumor cells," PNAS, 102(8):2910-2915 (2005).
Diamond, B. and Scharff, M. D., "Somatic mutation of the T15 heavy chain gives rise to an antibody with autoantibody specificity," Proc Natl Acad Sci., 81:5841-5844 (1984).
Document establishing 1998 publication of SIGMA Product Information Sheet, Nov. 6, 2018.
Donnez, J., et al., "Current Thinking on the Pathogenesis of Endometriosis," Gynecol Obstet Invest 54(supp 1):52-62 (2002).
Drake, A. W. and Papalia, G. A., "Biophysical Considerations for Development of Antibody-Based Therapeutics," Development of Antibody-Based Therapeutics, Chapter 5:95-97 (2012).
Duffau, P., et al., "Platelet CD154 Potentiates Interferon-α Secretion by Plasmacytoid Dendritic Cells in Systemic Lupus Erythematosus," Sci Transl Med., 2(47):47ra63 (2010).
Durkee, K. H., et al., "Immunoaffinity Chromatographic Purification of Russell's Viper Venom Factor X Activator Using Elution in High Concentrations of Magnesium Chloride," Protein Expression and Purification 4:405-411 (1993.
Ejima, D., et al., "Effective elution of antibodies by arginine and arginine derivatives in affinity column chromatography," Analyt Biochem 345:250-257 (2005).
English language translation of priority document, Japanese patent application JP2005101105, for European Patent Application No. EP1870459A1, submitted by opponents in opposition for EP2006381, filed Nov. 1, 2016.
English language translation of priority document, Japanese patent application JP2005378266, for European Patent Application No. EP1870459A1, submitted by opponents in opposition for EP2006381, filed Nov. 1, 2016.
European Patent Office Register Extract for European Patent No. EP1915397, submitted by opponents in opposition for EP2006381, filed Nov. 1, 2016.
Ewert, S., et al., "Stability improvement of antibodies for extracellular and intracellular applications: CDR grafting to stable frameworks and structure-based framework engineering," Methods, 34:184-199 (2004).
Examination Report No. 1 for Australian Patent Application 2013306700 dated Jun. 7, 2018.
Feinberg, H., et al., "Mechanism of pH-dependent N-Acetylgalactosamine Binding by a Functional Mimic of the Hepatocyte Asialoglycoprotein Receptor," J Biol Chem 275(45):35176-35184 (2000).
Ferl, G. Z., et al., "A Predictive Model of Therapeutic Monoclonal Antibody Dynamics and Regulation by the Neonatal Fc Receptor (FcRn)," Ann Biomed Eng., 33(11): 1640-1652 (2005); Erratum in: *Ann Biomed Eng.*, 39(10):2668 (2011).
Fiedler, M., et al., "An engineered IN-1 $F_{ab}$ fragment with improved affinity for the Nogo-A axonal growth inhibitor permits immunochemical detection and shows enhanced neutralizing activity," Protein Eng., 15(11):931-941 (2002).
Fillipovic, "Biochemical basis of human life," VLADOS, pp. 38-43 (2005).
Fillipovich, "Biochemical basis of human life," VLADOS, pp. (2005).
Finkelman, F. D., et al., "Anti-Cytokine Antibodies as Carrier Proteins," J Immunol 151(3):1235-1244 (1993).
Fisher, P. A. and Smith, David E., "Affinity purification of antibodies using antigens immobilized on solid supports," Biochem Soc Trans., 16(2):134-138 (1988).
Floto, R. A., et al., "Loss of function of a lupus-associated FcγRIIb polymorphism through exclusion from lipid rafts," Nat Med., 11(10):1056-1058 (2005).
Foote, J. and Winter, G., "Antibody Framework Residues Affecting the Conformation of the Hypervariable Loops," J Mol Biol, 224:487-499 (1992).

Fournier, E. M., et al., "Activation of Human Peripheral IgM$^+$ B Cells Is Transiently Inhibited by BCR-Independent Aggregation of FcγRIIB," J Immunol., 181:5350-5359 (2008).
Fujii, I., et al., "Antibody Affinity Maturation by Random Mutagenesis," Methods in Molecular Biology 248:345-359 (2004).
GE Healthcare. Application note 28-9277-92 AA. "High-throughput screening of elution pH for monoclonal antibodies on MabSelect SuRe using PreDictor plates," General Electric Company (2008).
Gera, N., et al., "Design of pH Sensitive Binding Proteins from the Hyperthermophilic Sso7d Scaffold," PLoS One 7(11):e48928:1-14 (2012).
Gerstner, R.B., et al., "Sequence Plasticity in the Antigen-binding Site of a Therapeutic Anti-HER2 Antibody," J Mol Biol 321(5):851-862 (2002).
Gessner, J.E., et al., "The IgG Fc receptor family," Ann Hematol 76(6):231-248 (1998).
Ghetie, V. and Ward, E. S., "Multiple Roles for the Major Histocompatibility Complex Class I-related Receptor FcRn," Annu Rev Immunol., 18:739-766 (2000).
Ghetie, V. and Ward, E. S., "FcRn: the MHC class I-related receptor that is more than an IgG transporter," Immunol Today 18(12):592-598 (1997).
Ghetie, V., et al., "Increasing the serum persistence of an IgG fragment by random mutagenesis," Nature Biotechnol 15:637-640 (1997).
Giudice, L. C. and Kao, L. C., "Endometriosis," Lancet 364:1789-1799 (2004).
Glick, B. R., et al., "Molecular Biotechnology—Principles and Applications of Recombinant DNA," edited, p. 168, paragraph 5, (Mar. 2005), with English translation thereof.
Gobburu, J. V. S., et al., "Pharmcokinetics/Dynamics of 5c8, a Monoclonal Antibody of CD154 (CD40 Ligand) Suppression of an Immune Response in Monkeys," J Pharmacol Exp Therapeutics 286(2):925-930 (1998).
Gonzalez, E. M., et al., "BMP-1/Tolloid-like Metalloproteases Process Endorepellin, the Angiostatic C-terminal Fragment of Perlecan," J Biol Chem., 280(8):7080-7087 (2005).
Goode, N.P., et al., "The glomerular basement Membrane Charge-selectivity Barrier: an Oversimplified Concept?" Nephrol Dial Transplant 11(9):1714-1716 (1996).
Graves, S. S., et al., "Molecular Modeling and Preclinical Evaluation of the Humanized NR-LU-13 Antibody," Clin Cancer Res 5:899-908 (1999).
Greenwood, J., et al., "Structural motifs involved in human IgG antibody effector functions," Eur J Immunol., 23:1098-1104 (1993).
Guo, S., "Recurrence of endometriosis and its control." Human Reproduction Update 15(4):441-461 (2009).
Guyre, P. M., et al., "Increased potency of Fc-receptor-targeted antigens," Cancer Immunol Immunother 45:146-148 (1997).
Hamers-Casterman, C., et al., "Naturally occurring antibodies devoid of light chains," Nature 363:446-448 (1993).
Han, H. Q. and Mitch, W. E., "Targeting the Myostatin Signaling Pathway to Treat Muscle Wasting Disease," Curr Opin Support Palliat Care 5(4):334-341 (2011).
Hanson, C. V., et al., "Catalytic antibodies and their applications," Curr Opin Biotechnol 16:631-636 (2005).
Harvey, et al., Lippincott's Illustrated Reviews: Immunology Second Edition Chapter 2 "Antigens and Receptors," 11-23 and Chapter 11 "Lymphocyte Effector Functions," 141-157 (2013).
Hasemann, C. A. and Capra, J. D., "Mutational Analysis of Arsonate Binding by a $CRI_{A+}$ Antibody," J Biol Chem., 266(12):7626-7632 (1991).
He, X. Y., et al., "Humanization and Pharmacokinetics of a Monoclonal Antibody with Specificity for Both E- and P-Selectin," J Immunol 160:1029-1035 (1998).
Heyman, B., "Feedback regulation by IgG antibodies," Immunol Lett., 88:157-161 (2003).
Hill, J. J., et al., "The Myostatin Propeptide and the Follistatin-related Gene Are Inhibitory Binding Proteins of Myostatin in Normal Serum," J Biol Chem 277(43):40735-40741 (2002).
Hinton, P. R., et al., "Engineered Human IgG Antibodies with Longer Serum Half-lives in Primates," J Biol Chem 279(8):6213-6216 (2004).

(56) References Cited

OTHER PUBLICATIONS

Hinton, P. R., et al., "An Engineered Human IgG1 Antibody with Longer Serum Half-Life," J Immunol 176:346-356 (2006).
Hird, V., et al., "Tumour localisation with a radioactively labelled reshaped human monoclonal antibody," Br J Cancer 64:911-914 (1991).
Hironiwa, N., et al., "Calcium-dependent antigen binding as a novel modality for antibody recycling by endosomal antigen dissociation," mAbs 8(1):65-73 (2016).
Hjelm, F., et al., "Antibody-Mediated Regulation of the Immune Response," Scand J Immunol., 64:177-184 (2006).
Holash, J., et al., "Vegf-Trap: A Vegf Blocker With Potent Antitumor Effects," PNAS, 99(17):11393-11398 (2002).
Hong, G., et al., "Enhanced Cellular Uptake and Transport of Polyclonal Immunoglobulin G and Fab After Their Cationization," J Drug Targeting 8(2):67-77 (2000).
Hoodless, P. A. and Wrana, J. L., "Mechanism and Function of Signaling by the TGFβ Superfamily," Curr Top Microbiol Immunol 228:235-272 (1998).
Hoogenboom, H., "Selecting and screening recombinant antibody libraries," Nature Biotechnology 23(9):1105-1116 (2005).
Horton, H. M., et al., "Potent In vitro and In vivo Activity and an Fc-Engineered Anti-CD19 Monoclonal Antibody against Lymphoma and Leukemia," Cancer Res., 68(19):8049-8057 (2008).
Hötzel, I., et al., "A strategy for risk management of antibodies with fast clearance," mAbs, 4(6):753-760 (2012).
Hughes-Jones, N.C., et al., "The Effect of pH and Ionic Strength on the Reaction between Anti-D and Erythrocytes," Immunology 7(1):72-81 (1964).
Huse, K., et al., "Purification of antibodies by affinity chromatography," J Biochem Biophys Methods, 51:217-231 (2002).
Hwang, W. Y. K., et al., "Use of human germline genes in a CDR homology-based approach to antibody humanization," Methods 36:35-42 (2005).
Idusogie, E. E., et al., "Engineered Antibodies with Increased Activity to Recruit Complement," Journal of Immunology 166(4):2571-2575, American Association of Immunologists, United States (Feb. 2001).
Idusogie, E.E., et al., "Mapping of the C1q Binding Site on Rituxan, a Chimeric Antibody With a Human IgG1 Fc," Journal of Immunology 164(8):4178-4184, American Association of Immunologists, United States (Apr. 2000).
Igawa, T., et al., "Antibody recycling by engineered pH-dependent antigen binding improves the duration of antigen neutralization," Nature Biotechnol 28(11):1203-1207 (2010).
Igawa, T., et al., "Engineered Monoclonal Antibody with Novel Antigen-Sweeping Activity In Vivo," PLOS One, 8(5):e63236 (2013).
Igawa, T., et al., "pH-dependent antigen-binding antibodies as a novel therapeutic modality," Biochim Biophys Acta., 1844(11):1943-1950 (2014).
Igawa, T., et al., "Engineering the variable region of therapeutic IgG antibodies," mAbs 3(3):243-252 (2011).
Igawa, T., et al., "Antibody Optimization Technologies for Developing Next Generation Antibody Therapeutics," Bio Industry, 28(7):15-21 (2011), with English translation.
Igawa, T., et al., "Reduced elimination of IgG antibodies by engineering the variable region," Protein Eng Des Sel 23(5):385-392 (2010).
Ishii, et al., A receptor involved in the regulation of the pharmacokinetics of antibody-based pharmaceuticals: FcRn, Folia Pharmacol Jpn., 136(5):280-284 (2010), with English translation.
Ito, W., et al., "The His-probe method: effects of histidine residues introduced into the complementarity-determining regions of antibodies on antigen-antibody interactions at different pH values," FEBS Letters 309(1):85-88 (1992).
Iwabe, T., et al., "Pathogenic significance of increased levels of interleukin-8 in the peritoneal fluid of patients with endometriosis," Fertility and Sterility 69(5):924-930 (1998).
Jaeger, "Clinical Immunology and Allergology," 2nd edition, M.: Medicina, 1990,2:484-5 (with English translation) •.
Jain, M., et al., "Engineering antibodies for clinical applications," Trends in Biotechnology 25(7):307-316 (2007).
Janeway, Immunobiology, 5th Edition, Chapter 3, Garland Science, New York (2001).
Janeway, Immunobiology, 5th Edition, Chapter 4, Garland Science, New York (2001).
Jefferis, R and Lund, J., "Interaction Sites on Human IgG-Fc for FcgammaR: Current Models," Immunology Letters, 82(1-2):57-65(2002).
Johnson, K. A., et al., "Cation exchange-HPLC and mass spectrometry reveal C-terminal amidation of an IgG1 heavy chain," Analytical Biochemistry 360(1):75-83 (2007).
Jones, T. D., et al., "Identification and removal of a promiscuous CD4+ T cell epitope from the C1 domain of factor VIII," J Thromb Haemostasis 3(5):991-1000 (2005).
Junghans, R. P. and Anderson, C. L., "The protection receptor for IgG catabolism is the $β_2$-microglobulin-containing neonatal intestinal transport receptor," Proc Natl Acad Sci 93:5512-5516 (1996).
Kabat, E. A., et al., "Sequences of Proteins of Immunological Interest," NIH, Pub. No. 91-3242, $5^{th}$ ed., vol. 1, pp. 679-687 (1991).
Kakita, M., et al., "Isolation of a Human Monoclonal Antibody with Strong Neutralizing Activity against Diphtheria Toxin," Infect Immun., 74(6):3682-3683 (2006).
Kamata, N., et al., "Comparison of pH and Ionic Strength Dependence of Interactions between Monoclonal Antibodies and Bovine β-Lactoglobulin," Biosci Biotech Biochem., 60(1):25-29 (1996).
Kashmiri, S. V. S., et al. "Generation, Characterization, and in Vivo Studies of Humanized Anticarcinoma Antibody CC49," Hybridoma 14(5):461-473 (1995).
Katayose, Y., et al., "MUC1-specific Targeting Immunotherapy with Bispecific Antibodies: Inhibition of Xenografted Human Bile Duct Carcinoma Growth," Cancer Res 56:4205-4212 (1996).
Khawli, L. A., et al., "Improved Tumor Localization and Radioimaging with Chemically Modified Monoclonal Antibodies," Cancer Biother Radiopharmaceut 11(3):203-215 (1996).
Kim, S. J., et al., "Antibody Engineering for the Development of Therapeutic Antibodies," Mol Cells 20(1):17-29 (2005).
Kim, I., et al., "Lowering of pI by acylation improves the renal uptake of $^{99m}$Tc-labeled anti-Tac dsFv: effect of different acylating reagents," Nuclear Med Biol 29(8):795-801 (2002).
Kim, I. S., et al., "Chemical Modification to Reduce Renal Uptake of Disulfide-Bonded Variable Region Fragment of Anti-Tac Monoclonal Antibody Labeled with $^{99m}$Tc," Bioconjugate Chem 10(3):447-453 (1999).
Kim, Y. S., et al., "Production of a Polyclonal Anti-Myostatin Antibody and the Effects on In Ovo Administration of the Antibody of Posthatch Broiler Growth and Muscle Mass," Poultry Science 86:1196-1205 (2007).
Kim, Y. S., et al., "Production of a Monoclonal Anti-Myostatin Antibody and the Effects of In Ovo Administration of the Antibody on Posthatch Broiler Growth and Muscle Mass," Poultry Science 85:1062-1071 (2006).
King, D. J., "Applications and Engineering of Monoclonal Antibodies," pp. 13-14 (1998).
King, D. J., "Applications and Engineering of Monoclonal Antibodies," Celltech Therapeutics, 27-75 (1998).
King, D. J., "Applications and Engineering of Monoclonal Antibodies," Taylor & Francis pp. 1-236 (2005).
Kingsley, D. M., "The TGF-β superfamily: new members, new receptors, and new genetic tests of function in different organisms," Genes & Dev 8:133-146 (1994).
Knappik, A., et al., "Fully Synthetic Human Combinatorial Antibody Libraries (HuCAL) Based on Modular Consensus Frameworks and CDRs Randomized with Trinucleotides," J Mol Biol 296:57-86 (2000).
Kobayashi, T., et al., "A Monoclonal Antibody Specific for a Distinct Region of Hen Egg-White Lysozyme," Mol Immunol 19(4):619-630 (1982).

(56) References Cited

OTHER PUBLICATIONS

Kobayashi, H., et al., "The Pharmacokinetic Characteristics of Glycolated Humanized Anti-Tac Fabs Are Determined by Their Isoelectric Points," Cancer Res 59(2):422-430 (1999).
Kohrt, H. E., "Stimulation of natural killer cells with a CD137-specific antibody enhances trastuzumab efficacy in xenotransplant models of breast cancer," J Clin Invest., 122(3):1066-1075 (2012). Retracted.
Komissarov, A.A., et al., "Site-specific Mutagenesis of a Recombinant Anti-single-stranded DNA Fab. Role of Heavy Chain Complementarity-determining Region 3 Residues in Antigen Interaction," 272(43):26864-26870 J Biol Chem (1997).
Kranz, D. M., et al., "Mechanisms of Ligand Binding by Monoclonal Anti-fluorescyl Antibodies," J Biol Chem, 257(12):6987-6995 (1982).
Kuroda, D., et al.,"Computer-aided antibody design," Protein Eng Des Sel, 25(10):507-521 (2012).
Laitinen, O. H., et al., "Brave new (strept)avidins in biotechnology," TRENDS Biotechnol 25(6):269-277 (2007).
Lazar, G. A., et al., "Engineered antibody Fc variants with enhanced effector function," PNAS, 103(11):4005-4010 (2006).
Lee, S. and McPherron, A. C., "Regulation of myostatin activity and muscle growth," PNAS 98(16):9306-9311 (2001).
Lee, S., "Genetic Analysis of the Role of Proteolysis in the Activation of Latent Myostatin," PLoS One 3(2):e1628, 7 pages (2008).
Lee, C. V., et al., "High-affinity Human Antibodies from Phage-displayed Synthetic Fab Libraries with a Single Framework Scaffold," 340:1073-1093 (2004).
Leong, S.R., et al., "Adapting Pharmacokinetic Properties of a Humanized Anti-interleukin-8 Antibody for Therapeutic Applications Using Site-specific Pegylation," Cytokine 16(3):106-119 (2001).
Li, D. H., et al., "CD72 Down-Modulates BCR-Induced Signal Transduction and Diminishes Survival in Primary Mature B Lymphocytes," J Immunol., 176:5321-5328 (2006).
Li, F. and Ravetch, J. V., "Inhibitory Fcγ receptor engagement drives adjuvant and anti-tumor activities of agonistic CD40 antibodies," Science, 333(6045):1030-1034 (2011).
Li, F. and Ravetch, J. V., "Apoptotic and antitumor activity of death receptor antibodies require inhibitory Fcγ receptor engagement," PNAS, 109(27):10966-10971 (2012).
Li, B., et al., "Construction and characterization of a humanized anti-human CD3 monoclonal antibody 12F6 with effective immunoregulation functions," Immunol 116(4):487-498 (2005).
Lin, Y. S., et al., "Preclinical Pharmacokinetics, Interspecies Scaling, and Tissue Distribution of a Humanized Monoclonal Antibody against Vascular Endothelial Growth Factor," J Pharmacol Exp Ther 288(1):371-378 (1999).
Linder, M., et al., "Design of a pH-dependent cellulose-binding domain," FEBS Letters 447:13-16 (1999).
Liu, H., et al., "Heterogeneity of Monoclonal Antibodies," J Pharmaceut Sci 97(7):2426-2447 (2008).
Lobo, E. D., et al., "Antibody Pharmacokinetics and Pharmacodynamics," J Pharm Sci 93:2645-2668 (2004).
Lund, L., et al., "Multiple Binding Sites on the $C_H2$ Domain of IgG for Mouse FcγRII," Mol Immunol., 29(1):53-59 (1992).
Maccallum, R. M., et al., "Antibody-antigen Interactions: Contact Analysis and Binding Site Topography," J Mol Biol 262:732-745 (1996).
Mackay, M., et al., "Selective dysregulation of the FcγIIB receptor on memory B cells in SLE," J Exp Med., 203(9):2157-2164 (2006).
Maeda, K., et al., "pH-dependent receptor/ligand dissociation as a determining factor for intracellular sorting of ligands for epidermal growth factor receptors in rat hepatocytes," J Controlled Release, 82:71-82 (2002).
Maier, J. K. X. and Labute, P., "Assessment of fully automated antibody homology modeling protocols in molecular operating environment," Proteins 82:1599-1610 (2014).
Maini, R. N., et al., "Double-Blind Randomized Controlled Clinical Trial of the Interleukin-6 Receptor Antagonist, Tocilizumab, in European Patients With Rheumatoid Arthritis Who Had an Incomplete Response to Methotrexate," Arth Rheum 54(9):2817-2829 (2006).
Malbec, O. and Daëron, M., "Antibodies against growth factor receptors can inhibit the proliferation of transformed cells via a cis-interaction with inhibitory FcR," Immunol Lett., 143:28-33 (2012).
Manger, K., et al., "Fcγ Receptor IIa Polymorphism in Caucasian Patients with Systemic Lupus Erythematosus," Arth Rheum., 41(7):1181-1189 (1998).
Marshall, S. A., et al., "Rational design and engineering of therapeutic proteins," DDT 8(5):212-221 (2003).
Martin, W. L., et al., "Crystal Structure at 2.8 Å of an FcRn/ Heterodimeric Fc Complex: Mechanism of pH-Dependent Binding," Mol Cell 7:867-877 (2001).
Matsumiya, S., et al., "Structural Comparison of Fucosylated and Nonfucosylated Fc Fragments of Human Immunoglobulin G1," J Mol Biol., 368:767-779 (2007).
Maurer, P. H., et al., "Antigenicity of Polypeptides (PolyαAmino Acids): Calcium-dependent and Independent Antibodies," J Immunol., 105(3):567-573 (1970).
Maxfield, F. R. and McGraw, T. E., "Endocytic Recycling," Nat Rev Mol Cell Biol 5(2):121-132 (2004).
Maxwell, K. F., et al., "Crystal structure of the human leukocyte Fc receptor, FcγRIIa," Nat Struct Biol., 6(5):437-442 (1999).
McCroskery, S., et al., "Improved muscle healing through enhanced regeneration and reduced fibrosis in myostatin-null mice," J Cell Sci 118:3531-3541 (2005).
McPherron, A. C., et al., "Regulation of skeletal muscle mass in mice by a new TGF-β superfamily member," Nature 387:83-90 (1997).
McPherron, A. C. and Lee, S., "Double muscling in cattle due to mutations in the myostatin gene," Proc Natl Acad Sci 94:12457-12461 (1997).
Mellman, I., "The Importance of Being Acid: The Role of Acidification in Intracellular Membrane Traffic," J Exp Biol 172:39-45 (1992).
Merchant, A. M., et al., "An efficient route to human bispecific IgG," Nature Biotechnology 16:677-681 (1998).
Meyer, T., et al., "Bevacizumab immune complexes activate platelets and induce thrombosis in FCGR2A in transgenic mice," J Thromb Haemost., 7:171-181 (2009).
Mi, W., et al., "Targeting the neonatal Fc receptor for antigen delivery using engineered Fc fragments," J Immunol., 181(11):7550-7561 (2008).
Milstein, C. and Cuello, A.C., "Hybrid hybridomas and their use in immunohistochemistry," Nature, 305(5934):537-540 (1983).
Mimoto, F., et al., "Engineered antibody Fc variant with selectively enhanced FcγRIIb binding over both FcγRIIa$^{R131}$ and FcγRIIa$^{H131}$," Protein Eng Des Sel., 26(10):589-598 (2013).
Mohan, C., "Buffers: A guide for the preparation and use of buffers in biological systems," Calbiochem, EMD, 37 pages (2003).
Montero-Julian, F. A., et al., "Pharmacokinetic Study of Anti-Interleukin-6 (IL-6) Therapy With Monoclonal Antibodies: Enhancement of IL-6 Clearance by Cocktails of Anti-IL-6 Antibodies," Blood 85(4):917-924 (1995).
Moore, G. L., et al., "Engineered Fc variant antibodies with enhanced ability to recruit complement and mediate effector functions," mAbs, 2(2):181-189 (2010).
Morgan, A., et al., "The N-terminal end of the $C_H2$ domain of chimeric human IgG1 anti-HLA-DR is necessary for C1q, FcγRI and FcγRIII binding," Immunol., 86:319-324 (1995).
Muller, Y. A., "VEGF and the Fab fragment of a humanized neutralizing antibody: crystal structure of the complex at 2.4 Å resolution and mutational analysis of the interface," Structure 6:1153-1167 (1998).
Murata, V. M., et al., "Anti-Digoxin Fab Variants Generated by Phage Display," Mol Biotechnol 54:269-277 (2013).
Murtaugh, M. L., et al., "A Combinatorial Histidine Scanning Library Approach to Engineer Highly pH-Dependent Protein Switches," Protein Sci 20:1619-1631 (2011).

(56) References Cited

OTHER PUBLICATIONS

Muta, T., et al., "A 13-amino-acid motif in the cytoplasmic domain of FcγRIIB modulates B-cell receptor signalling," Nature, 368:70-73 (1994).

Nakamura, A., et al., "Fcγ Receptor IIB-deficient Mice Develop Goodpasture's Syndrome upon Immunization with Type IV Collagen: A Novel Murine for Autoimmune Glomerular Basement Membrane Disease," J Exp Med., 191(5):899-905 (2000).

Narhi, L. O., et al., "Effect of Three Elution Buffers on the Recovery and Structure of Monoclonal Antibodies," Analytical Biochem., 253:236-245 (1997).

Nesterova, A., et al., "Glypican-3 as a novel target for an antibody-drug conjugate," Exp Mol Therapeut, 98$^{th}$ AACR Annual Meeting, Apr. 14-18, 2007, Los Angeles, CA, Abstract.

Nimmerjahn, F. and Ravetch, J. V., "Divergent Immunoglobulin G Subclass Activity Through Selective Fc Receptor Binding," Science, 310:1510-1512 (2005).

Nimmerjahn, F. and Ravetch, J. V., "Fcγ receptors as regulators of immune responses," Nat Rev Immunol., 8:34-47 (2008).

Nishimoto, N. and Kishimoto, T., "Interleukin 6: from bench to bedside," Nature Clinical Practice. Rheumatology 2(11):619-626 (2006).

Nishimoto, N., et al., "Humanized anti-interleukin-6 receptor antibody treatment of multicentric Castleman Disease," Blood 106(8):2627-2632 (2005).

Nordlund, H. R., et al., "Introduction of histidine residues into avidin subunit interfaces allows pH-dependent regulation of quaternary structure and biotin binding," FEBS Letters 555:449-454 (2003).

Ober, R. J., et al., "Visualizing the Site and Dynamics of IgG Salvage by the MHC Class I-Related Receptor, FcRn," J Immunol 172:2021-2029 (2004).

Ohno, S., et al., "Antigen-binding specificities of antibodies are primarily determined by seven residues of $V_H$," Proc Natl Acad Sci., 82:2945-2949 (1985).

Olferiev, M., et al., "The Role of Activating Protein 1 in the Transcriptional Regulation of the Human FCGR2B Promoter Mediated by the—343 G→C Polymorphism Associated with Systemic Lupus Erythematosus," J Biol Chem., 282(3):1738-1746 (2007).

Onda, M., et al., "Lowering the Isoelectric Point of the Fv Portion of Recombinant Immunotoxins Leads to Decreased Nonspecific Animal Toxicity without Affecting Antitumor Activity," Cancer Res 61:5070-5077 (2001).

Ono, K., et al., "The humanized anti-HM1.24 antibody effectively kills multiple myeloma cells by human effector cell-mediated cytotoxicity," Mol Immunol 36:387-395 (1999).

OriGene Technologies, Inc. Data Sheet, "Polyclonal Antibody to Myostatin (79-92)-Serum," No. AP02123SU-N, (Mar. 19, 2013).

Osbourn, J. K., et al., "Generation of a panel of related human scFv antibodies with high affinities for human CEA," Immunotechnol 2:181-196 (1996).

Ozhegov et al., "Tolkovyi Slovar Russkogo iazyka," p. 292 (2004)(with English translation of the relevant passage defining "control").

Pakula, A. A. and Sauer, R. T., "Genetic Analysis of Protein Stability and Function," Annu Rev Genet 23:289-310 (1989).

Palladino, M. A., et al., "Anti-TNF-α Therapies: The Next Generation," Nature Rev 2:736-746 (2003).

Pancook, J. D., et al., "In Vitro Affinity Maturation of Human IgM Antibodies Reactive with Tumor-Associated Antigens," Hybridoma and Hybridomics 20(6):383-396 (2001).

Pardridge, W. M., et al., "Enhanced Endocytosis in Cultured Human Breast Carcinoma Cells and In Vivo Biodistribution in Rats of a Humanized Monoclonal Antibody after Cationization of the Protein," J Pharacol Exp Ther 286(1):548-554 (1998).

Pardridge, W. M., et al., "Enhanced Cellular Uptake and in Vivo Biodistribution of a Monoclonal Antibody following Cationization," J Pharmaceut Sci 84(8):943-948 (1995).

Patel, T. V., et al., "A Forgotten Cause of Kidney Injury in Chronic Myelomonocytic Leukemia," Am J Kidney Dis 54(1):159-164 (2009).

Pavlinkova, G., et al., "Charge-Modified Single Chain Antibody Constructs of Monoclonal Antibody CC49: Generation, Characterization, Pharmacokinetics, and Biodistribution Analysis," Nucl Med Biol 26(1):27-34 (1999).

Pavlou, A. K. and Belsey, M. J., "The therapeutic antibodies market to 2008," Eur J Pharmaceut Biopharmaceut 59:389-396 (2005).

Pejchal, R., et al., "A Conformational Switch in Human Immunodeficiency Virus gp41 Revealed by the Structures of Overlapping Epitopes Recognized by Neutralizing Antibodies," J Virol 83(17):8451-8462 (2009).

Pirruccello-Straub, M., et al., "Blocking extracellular activation of myostatin as a strategy for treating muscle wasting," Scientific Reports, 8:2292 (2018).

Poduslo, J. F. and Curran, G. L., "Polyamine Modification Increases the Permeability of Proteins at the Blood-Nerve and Blood-Brain Barriers," J Neurochem 66:1599-1609 (1996).

Pons, J., et al., "Energetic analysis of an antigen/antibody interface: Alanine scanning mutagenesis and double mutant cycles on the HyHEL-10/lysozyme interaction," Protein Sci 8(5):958-968 (1999).

Presta, L. G., "Engineering of therapeutic antibodies to minimize immunogenicity and optimize function," Adv Drug Del Rev 58(5-6):640-656 (2006).

Promega Protocols and Applications Guide, Second Edition, 1991.

Radaev, S. and Sun, P. D., "Recognition of IgG by Fcγ Receptor," J Biol Chem., 276(19):16478-16483 (2001).

Radaev, S., et al., "The Structure of a Human Type III Fcγ Receptor in Complex with Fc," J Biol Chem., 276(19):16469-16477 (2001).

Rajpal, A., et al., "A general method for greatly improving the affinity of antibodies by using combinatorial libraries," PNAS 102(24):8466-8471 (2005).

Raposo, B., et al., "Epitope-specific antibody response is controlled by immunoglobulin $V_H$ polymorphisms," J Exp Med 211(3):405-411 (2014).

Supplemental material to Raposo, B., et al., "Epitope-specific antibody response is controlled by immunoglobulin $V_H$ polymorphisms," J Exp Med 211(3):405-411 (2014).

Raso, V., et al., "Intracellular Targeting with Low pH-triggered Bispecific Antibodies," J Biolog Chem., 272(44):27623-27628 (1997).

Raso, V., et al., "Antibodies Capable of Releasing Diphtheria Toxin in Response to the Low pH Found in Endosomes," J Biol Chem 272(44):27618-27622 (1997).

Raso, V., "Intracellular Targeting Using Bispecific Antibodies," Methods in Molecular Medicine 25:37-50 (2000).

Rathanaswami, P., et al., "Demonstration of an in vivo generated sub-picomolar affinity fully human monoclonal antibody to interleukin-8," Biochem Biophys Res Communic 334:1004-1013 (2005).

Ravetch, J. V. and Lanier, L. L., "Immune Inhibitory Receptors," Science, 290:84-89 (2000).

Reddy M.P., et al., "Elimination of Fc Receptor-Dependent Effector Functions of a Modified IgG4 Monoclonal Antibody to Human CD4," J Immunol 164(4):1925-1933 (2000).

Reichert, J. M., et al., "Monoclonal antibody successes in the clinic," Nat Biotechnol., 23(9):1073-1078 (2005).

Reichert, J. M. and Valge-Archer, V. E., "Development trends for monoclonal antibody cancer therapeutics," Nature Rev Drug Discov., 6:349-356 (2007).

Reimann, K. A., et al., "A Humanized Form of a CD4-Specific Monoclonal Antibody Exhibits Decreased Antigenicity and Prolonged Plasma Half-Life in Rhesus Monkeys While Retaining Its Unique Biological and Antiviral Properties," Aids Research and Human Retroviruses 13(11):933-943 (1997).

Reverberi, R. and Reverberi, L., "Factors affecting the antigen-antibody reaction," Blood Transfus 5:227-240 (2007).

Rich, R. L. and Myszka, D. G., "Grading the commercial optical biosensor literature—Class of 2008: 'The Mighty Binder,'" J Mol Recog., 23:1-64 (2010).

Richards, J. O., et al., "Optimization of antibody binding to FcγRIIa enhances macrophage phagocytosis of tumor cells," Mol Cancer Ther., 7(8):2517-2527 (2008).

Rituximab—Shire, Experimental data characterizing the binding of rituximab to its antigen CD20 and to human FcRn, submitted Dec. 20, 2018.

(56) References Cited

OTHER PUBLICATIONS

Rituximab (Wikipedia), accessed on Oct. 24, 2018, submitted in Opposition, with machine English translation.
Rituximab biologic license application, Nov. 26, 1997.
Rituximab product information, IDEC, 1997.
Robles-Carrillo, L., et al., "Anti-CD40L Immune Complexes Potently Activate Platelets In Vitro and Cause Thrombosis in FCGR2A Transgenic Mice," J Immunol., 185:1577-1583 (2010).
Roitt, et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Roitt, I., et al., Moscow, Mir, Immunology, 110 (2000).
Roitt, I., Moscow, Mir, Immunology, 9 (2000).
Rojas, J. R., et al., "Formation, Distribution, and Elimination of Infliximab and Anti-Infliximab Immune Complexes in Cynomolgus Monkeys," J Pharmacol Exper Therapeut., 313(2):578-585 (2005).
Roopenian, D. C. and Akilesh, S., "FcRn: the neonatal Fc receptor comes of age," Nat Rev Immunol., 7:715-725 (2007).
Rothe, A., et al., "Ribosome display for improved biotherapeutic molecules," Expert Opin Biol Ther. 6(2):177-187 (2006).
Rudikoff, S., et al. "Single amino acid substitution altering antigen-binding specificity," Proc Natl Acad Sci 79:1979-1983 (1982).
Russo, R. C., et al., "The CXCL8/IL-8 chemokine family and its receptors in inflammatory diseases," Expert Rev Clin Immunol 10(5):593-619 (2014).
Ryman, J. T., and Meibohm, B., "Pharmacokinetics of Monoclonal Antibodies," CPT Pharmacometrics Syst Pharmacol 6:576-588 (2017).
Sada, E., et al., "Effect of histidine residues in antigenic sites of pH dependence of immuno-adsorption equilibrium," Appl Microbiol Biotechnol., 27:528-532 (1988).
Salfeld, J.G., "Isotype Selection in Antibody Engineering," Nature Biotechnology 25(12):1369-1372, Nature America Publishing, United States (2007).
Salmon, J. E., et al., "FcγRIIA Alleles Are Heritable Risk Factors for Lupus Nephritis in African Americans," J Clin Invest., 97:1348-1354 (1996).
Sarkar, C.A., et al., "Rational Cytokine Design for Increased Lifetime and Enhanced Potency Using pH-activated Histidine Switching," Nature Biotechnology 20(9):908-913 (2002).
Sato, K., et al., "Reshaping a Human Antibody to Inhibit the Interleukin 6-dependent Tumor Cell Growth," Cancer Res., 53:851-856 (1993).
Sazinsky, S. L., et al., "Aglycosylated immunoglobulin $G_1$ variants productively engage activating Fc receptors," PNAS, 105(51):20167-20172 (2008).
Scappaticci, F. A., et al., "Arterial Thromboembolic Events in Patients with Metastatic Carcinoma Treated with Chemotherapy and Bevacizumab," J Natl Cancer Inst., 99:1232-1239 (2007).
Schaeffer, R.C. Jr., et al., "The Rat Glomerular Filtration Barrier Does Not Show Negative Charge Selectivity," Microcirculation 9(5):329-342, Wiley-Blackwell, United States (2002).
Schier, R., et al., "Isolation of Picomolar Affinity Anti-c-erbB-2 Single-chain Fv by Molecular Evolution of the Complementarity Determining Regions in the Center of the Antibody Binding Site," J Mol Biol., 263:551-567 (1996).
Schlothauer, T., et al., "Novel human IgG1 and IgG4 Fc-engineered antibodies with completely abolished immune effector functions," Protein Eng Des Sel., 29(10):457-466 (2016).
Schmitz, U., et al., "Phage Display: a Molecular Tool for the Generation of Antibodies—a Review," Placenta 21 Suppl A:S106-S112, Elsevier, Netherlands (2000).
Schroeder, Jr., H. W., "Similarity and divergence in the development and expression of the mouse and human antibody repertoires," Dev Comp Immunol., 30:119-135 (2006).
Schroter, C., et al., "A generic approach to engineer antibody pH-switches using combinatorial histidine scanning libraries and yeast display," mAbs 7:1, 138-151 (2015).

Sequence Alignments and modification scheme filed during Oral Proceedings, Jul. 25, 2018, issued by European Patent Office for Opposition in EP2006381.
Shadduck, R. K., et al., "Fractionation of Antibodies to L-Cell Colony-Stimulating Factor by Affinity Chromatography," Blood, 53(6):1182-1190 (1979).
Sharifi, J., et al., "Improving monoclonal antibody pharmacokinetics via chemical modification," Q. J. Nucl. Med. 42:242-249 (1998).
Shields, R. L., et al., "High Resolution Mapping of the Binding Site of Human IgG1 for FcγRI, FcγRII, FcγRIII, and FcRn and Design of IgG1 Variants with Improved Binding to the FcγR," J Biol Chem 276(9):6591-6604 (2001).
Shinkawa, T., et al., "The Absence of Fucose but Not the Presence of Galactose or Bisecting N-Acteylglucosamine of Human IgG1 Complex-type Oligosaccharides Shows the Critical Role of Enhancing Antibody-dependent Cellular Cytotoxicity," J Biol Chem., 278(5):3466-3473 (2003).
Shire, S.J., et al., "Challenges in the Development of High Protein Concentration Formulations," Journal of Pharmaceutical Sciences 93(6):1390-1402, Elsevier, United States (2004).
Siberil, S., et al., "Molecular aspects of human FcγR interactions with IgG: Functional and therapeutic consequences," Immunol Lett., 106:111-118 (2006).
Sigma-Aldrich®, Product Information, Monoclonal Anti-Flag® M1, Clone M1, accessed at http://www.sigmaaldrich.com/content/dam/sigmaaldrich/ does/Sigma/Datasheet/f3040dat.pdf, 1 page (2008).
Sigma, Product Information Sheet, H-Y Medium, Product No. H9014 (1998).
Sinclair, N. R., "Regulation of the Immune Response," J Exp Med., 129(6):1183-1201 (1969).
Singer, M., and Berg, P., "Genes & Genomes," Structure of Proteins 67-69 (1991).
Smith, K. G. C. and Clatworthy, M. R., "FcγRIIB in autoimmunity and infection: evolutionary and therapeutic implications," Nat Rev Immunol., 10(5):328-343 (2010).
Sondermann, P., et al., "The 3.2-Å crystal structure of the human IgG1 Fc fragment-FcγRIII complex," Nature, 406:267-273 (2000).
Sondermann, P., et al., "Molecular Basis for Immune Complex Recognition: A Comparison of Fc-Receptor Structures," J Mol Biol., 309:737-749 (2001).
Sondermann, P., et al., "Crystal structure of the soluble form of the human Fcγ-receptor IIb: a new member of the immunoglobulin superfamily at 1.7 Å resolution," The EMBO Journal, 18(5):1095-1103 (1999).
Stearns, D. J., et al., "The Interaction of a $Ca^{2+}$-dependent Monoclonal Antibody with the Protein C Activation Peptide Region," J Biol Chem., 263(2):826-832 (1988).
Stepanov, V. M., "Molecular Biology. Structure and Functions of Proteins," $3^{rd}$ Edition, Moscow University Publishing House: Science, pp. 61-62 (2005).
Stewart, J. D., "Site-Directed Mutagenesis of a Catalytic Antibody: An Arginine and a Histidine Residue Play Key Roles," Biochem., 33:1994-2003 (1994).
Strand, V., et al., "Biologic Therapies in Rheumatology: Lessons Learned, Future Directions," Nature Reviews Drug Discovery 6(1):75-92, Nature Publishing Group, England (2007).
Su, K., et al., "Expression Profiled of FcγRIIb on Leukocytes and Its Dysregulation in Systemic Lupus Erythematosus," J Immunol., 178(5):3272-3280 (2007).
Summary of Information about Antibodies in Examples of Patent, submitted by opponents in opposition for EP2006381, posted by European Patent Office on Apr. 13, 2018.
Suzuki, T., et al., "Importance of Neonatal FcR in Regulating the Serum Half-Life of Therapeutic Proteins Containing the Fc Domain of Human IgG1: A Comparative Study of the Affinity of Monoclonal Antibodies and Fc-Fusion Proteins to Human Neonatal FcR," J Immunol., 184:1968-1976 (2010).
Szlama, G., et al., "Latent myostatin has significant activity and this activity is controlled more efficiently by WFIKKN1 than by WFIKKN2," FEBS J 280:3822-3839 (2013).
The Chemical PE Thread, Thunder's Place, blog entry, Jun. 1, 2014, Retrieved from the Internet: URL:https://www.thundersplace.org/male-supplements/the-chemical-pe thread-7.html92.

(56) References Cited

OTHER PUBLICATIONS

Tabrizi, M.A., et al., "Elimination Mechanisms of Therapeutic Monoclonal Antibodies," Drug Discovery Today 11(1-2):81-88, Virgin Mailing and Distribution, England (2006).
Tan, P.H., et al., "Engineering the Isoelectric Point of a Renal Cell Carcinoma Targeting Antibody Greatly Enhances scFV Solubility," Immunotechnology 4(2):107-114, Elsevier, Netherlands (1998).
Tarantul, V. Z., "Explanatory Biotechnological Dictionary. Russian-English," Languages of Slavic Cultures, p. 72 (2009).
Tarditi, L., et al., "Selective High-performance Liquid Chromatographic Purification of Bispecific Monoclonal Antibodies," Journal of Chromatography 599(1-2):13-20, Elsevier, Netherlands (1992).
Teeling, J.L., et al., "The Biological Activity of Human CD20 Monoclonal Antibodies is Linked to Unique Epitopes on CD20," Journal of Immunology 177(1):362-371, American Association of Immunologists, United States (2006).
Ten Kate, C.I., et al., "Effect of Isoelectric Point on Biodistribution and Inflammation: Imaging With Indium-111-labelled IgG," European Journal of Nuclear Medicine 17(6-8):305-309, Springer Verlag, Germany (1990).
Travis, J., et al., "Isolation of Albumin from Whole Human Plasma and Fractionation of Albumin-Depleted Plasma," Biochem J., 157:301-306 (1976).
Tsuchiya, Credit Suisse Seminar, "Therapeutic Antibody," at Fuji-Gotemba Laboratories, p. 21 (2006).
Tsurushita, N., et al., "Design of humanized antibodies: From anti-Tac to Zenapax," Methods, 36:69-83 (2005).
Vaisitti, T., et al., "Cationization of monoclonal antibodies: Another step towards the Magic Bullet"? J Biol Regul Homeost Agents, 19:105-112 (2005).
Vajdos, F. F., et al., "Comprehensive Functional Maps of the Antigen-binding Site of an Anti-ErbB2 Antibody Obtained with Shotgun Scanning Mutagenesis," J Mol Biol 320:415-428 (2002).
Van Walle, I., et al., "Immunogenicity screening in protein drug development," Expert Opin. Biol. Ther. 7(3):405-418 (2007).
Van Den Abbeele, et al., "Antigen-Binding Site Protection During Radiolabeling Leads to a Higher Immunoreactive Fraction," J''Nucl Med., 32:116-122 (1991).
Vaughn, D. E. and Bjorkman, P. J., "Structural bases of pH-dependent antibody binding by the neonatal Fc receptor," Structure, 6(1):63-73 (1998).
Venturi, M., et al., "The Monoclonal Antibody 1F6 Identifies a pH-dependent Conformational Change in the Hydrophilic $NH_2$ Terminus of NhaA $Na^+/H^+$ Antiporter of *Escherichia coli*," J Biolog Chem., 275(7):4734-4742 (2000).
Vercellini, P., et al., "Postoperative oral contraceptive exposure and risk of endometrioma recurrence," Am J Obstet Gynecol 198:504.e1-504.e5 (2008).
Verhoeyen, M., et al., "Re-shaped human anti-PLAP antibodies," Chapter 5, 37-43 in Monoclonal Antibodies: Applications in Clinical Oncology, A.A. Epenetos, Ed., Chapman and Hall (1991).
Verhoeyen, M.E., et al., "Construction of a reshaped HMFG1 antibody and comparison of its fine specificity with that of the parent mouse antibody," Immunology 78:364-370, Blackwell Scientific, England (1993).
Veri, M.-C., et al., "Monoclonal antibodies capable of discriminating the human inhibitory Fcγ-receptor IIB (CD32B) from the activating Fcγ-receptor IIA (CD32A): biochemical, biological and functional characterization," Immunology, 121:392-404 (2007).
Veri, M.-C., et al., "Therapeutic Control of B Cell Activation via Recruitment of Fcγ Receptor IIb (CD32B) Inhibitory Function With a Novel Bispecific Antibody Scaffold," Arth Rheum., 62(7):1933-1943 (2010).
Wang, W., "Instability, stabilization, and formulation of liquid protein pharmaceuticals," Int'l J Pharmaceutics 185:129-188 (1999).
Wang, W., et al., "Monoclonal Antibodies with Identical Fc Sequences Can Bind to FcRn Differentially with Pharmacokinetic Consequences," Drug Metab Dispos., 39(9):1469-1477 (2011).
Wagner, K. R., et al., "Loss of Myostatin Attenuates Severity of Muscular Dystrophy in mdx Mice," Ann Neurol 52:832-836 (2002).
Ward, S. L. and Ingham, K. C., "A Calcium-Binding Monoclonal Antibody That Recognized a Non-Calcium-Binding Epitope in the Short Consensus Repeat Units (SCRs) of Complement Clr," Mol Immunol., 29(1):83-93 (1992).
Warmerdam, P. A. M., et al.,"Molecular Basis for a Polymorphism of Human Fcγ II (CD32)," J Exp Med., 172:19-25 (1990).
Weiss, G. A., et al., "Rapid mapping of protein functional epitopes by combinatorial alanine scanning," PNAS, 97(16):8950-8954 (2000).
Wenink, M. H., et al., "The Inhibitory FγIIb Receptor Dampens TLR4-Mediated Immune Responses and Is Selectively Up-regulated on Dendritic Cells from Rheumatoid Arthritis Patients with Quiescent Disease," J Immunol., 183:4509-4520 (2009).
Wernersson, S., et al., "IgG-Mediated Enhancement of Antibody Responses is Low in Fc Receptor γ Chain-Deficient Mice and Increased in FcγRII-Deficient Mice," J Immunol, 163:618-622 (1999).
Whittemore, L., et al., "Inhibition of myostatin in adult mice increases skeletal muscle mass and strength," Biochem Biophys Res Commun 300:965-971 (2003).
Wiens, G.D., et al., "Somatic Mutation in VH Complementarity-determining Region 2 and Framework Region 2: Differential Effects on Antigen Binding and Ig Secretion," Journal of Immunology 159(3):1293-1302, American Association of Immunologists, United States (1997).
Wiens, G.D., et al., "Mutation of a Single Conserved Residue in VH Complementarity-determining Region 2 Results in a Severe Ig Secretion Defect," Journal of Immunology 167(4):2179-2186, American Association of Immunologists, United States (2001).
Wikipedia, "Chaotropic agent" [online], [retrieved on Nov. 2, 2015]. Retrieved from the Internet: https://en.wikipedia.org/wiki/Chaotropic_agent.
Wilson, N. S., et al., "An Fcγ Receptor-Dependent Mechanism Drives Antibody-Mediated Target-Receptor Signaling in Cancer Cells," Cancer Cell, 19:101-113 (2011).
Wojciak, J. M., et al., "The crystal structure of sphingosine-1-phosphate in complex with a Fab fragment reveals metal bridging of an antibody and its antigen," PNAS, 106(42):17717-17722 (2009).
Wolfman, N. M., "Activation of latent myostatin by the BMP-1/tolloid family of metalloproteinases," PNAS, 100(26):15842-15846 (2003).
Written Submissions of Opponent 1, Alexion Pharmaceuticals, Inc., submitted Apr. 13, 2018 in response to Summons to attend Oral Proceedings dated Feb. 1, 2018, in Opposition of European Patent No. 2006381.
Written Submissions Opponent 2, Novo Nordisk A/S, submitted Apr. 13, 2018 in response to Summons to Oral Proceedings scheduled for Jun. 13, 2018, in Opposition of European Patent No. 2006381.
Written Submissions Opponent 3, Olswang LLP, submitted Apr. 13, 2018 in response to Opposition Division's Summons to Oral Proceedings scheduled for Jun. 13, 2018, in Opposition of European Patent No. 2006381.
Wu, H., et al., "Development of Motavizumab, an Ultra-potent Antibody for the Prevention of Respiratory Syncytial Virus Infection in the Upper and Lower Respiratory Tract," J Mol Biol., 368:652-666 (2007).
Wu, S.-J., et al., "Structure-based engineering of a monoclonal antibody for improved solubility," Protein Eng Des Sel., 23(8):643-651 (2010).
Wu, H., et al., "Stepwise in vitro affinity maturation of Vitaxin, an $α_vβ_3$-specific humanized mAb," Proc Natl Acad Scie 95:6037-6042 (1998).
Wu, H., et al., "Ultra-potent Antibodies Against Respiratory Syncytial Virus: Effects of Binding Kinetics and Binding Valence on Viral Neutralization," J Mol Biol 350:126-144 (2005).
Xiang, J., et al., "Study of B72.3 Combining Sites by Molecular Modeling and Site-directed Mutagenesis," Protein Engineering 13(5):339-344, Oxford University Press, England (2000).
Xu, Y., et al., "FcγRs Modulate Cytotoxicity of Anti-Fas Antibodies: Implications for Agonistic Antibody-Based Therapeutics," J Immunol., 171:562-568 (2003).

(56) References Cited

OTHER PUBLICATIONS

Yada, et al., Lippincott's Illustrated Reviews: Immunology Second Edition, pp. 11-23 (Chapter 2) and pp. 149-165 (Chapter 11) (2013). (English equivalent, Harvey 2013).
Yamasaki, Y., et al., "Pharmacokinetic Analysis of in Vivo Disposition of Succinylated Proteins Targeted to Liver Nonparenchymal Cells via Scavenger Receptors: Importance of Molecular Size and Negative Charge Density for in Vivo Recognition by Receptors," J Pharmacol Exp Therapeut., 301(2):467-477 (2002).
Yang, K., et al., "Tailoring Structure-function and Pharmacokinetic Properties of Single-chain Fv Proteins by Site-specific PEGylation," Protein Engineering 16(10):761-770 (2003).
Yang, W.P., et al., "CDR Walking Mutagenesis for the Affinity Maturation of a Potent Human Anti-HIV-1 Antibody into the Picomolar Range," Journal of Molecular Biology 254(3):392-403 (1995).
Yarilin, A. A., "Principles of immunology: Textbook—M.: Medicina," Fundamentals of Immunology 608:169-172, 354-358 (1999), with English translation.
Yarilin, "Osnovy immunologii," M.Meditsina, 1999, pp. 181-184.
Yarilin, "Osnovy immunologii," M.Meditsina, 1999, pp. 172-174.
Yeung, Y. A., et al., "Engineering Human IgG1 Affinity to Human Neonatal Fc Receptor: Impact of Affinity Improvement on Pharmacokinetics in Primates," J Immunol 182:7663-7671 (2009).
Ying, Y. and Liangyi, X., "Large Yellow Croaker MSTN-1 Prodomain Prokaryotic Expression, Polyclonal Antibody Preparation and Antibody Function Identification," Chinese Journal of Cell Biology, 36(10):1344-1349 (2014), English abstract.
Yuasa, T., et al., "Deletion of Fcγ Receptor IIB Renders H-$2^b$ Mice Susceptible to Collagen-induced Arthritis," J Exp Med., 189(1):187-194 (1999).
Zalevsky, J., et al., "Enhanced antibody half-life improves in vivo activity," Nat Biotechnol., 28(2):157-159 (2010).
Zalevsky, J., et al., "The impact of Fc engineering on an anti-CD19 antibody: increased Fcγ receptor affinity enhances B-cell clearing in nonhuman primates," Blood, 113(16):3735-3743 (2009).
Zhang, M., et al., "Effective therapy for a murine model of human anaplastic large-cell lymphoma with the anti-CD30 monoclonal antibody, HeFi-1, does not require activating Fc receptors," Blood, 108(2):705-710 (2006).
Zhang, Y., et al., "Immune Complex/Ig Negatively Regulate TLR4-Triggered Inflammatory Response in Macrophages through FcγRIIb-Dependent $PGE_2$ Production," J Immunol., 182:554-562 (2009).
Zheng, Y., et al., "Translational Pharmacokinetics and Pharmacodynamics of an FcRn-Variant Anti-CD4 Monoclonal Antibody From Preclinical Model to Phase I Study," Clin Pharmacol & Ther., 89(2):283-290 (2011).
Zhou, T., et al., "Interfacial metal and antibody recognition," PNAS, 102(41):14575-14580 (2005).
Zhu, X., et al., "MHC Class I-Related Neonatal Fc Receptor for IgG Is Functionally Expressed in Monocytes, Intestinal Macrophages, and Dendritic Cells," J Immunol., 166:3266-3276 (2001).
Zimmers, T. A., et al., "Induction of Cachexia in Mice by Systemically Administered Myostatin," Science 296:1486-1488 (2002).
Zuckier, L. S., et al., "Chimeric Human-Mouse IgG Antibodies with Shuffled Constant Region Exons Demonstrate that Multiple Domains Contribute to in Vivo Half-Life." Cancer Res., 58:3905-3908 (1998).
Zwick, M.B., et al., "The Long Third Complementarity-determining Region of the Heavy Chain Is Important in the Activity of the Broadly Neutralizing Anti-human Immunodeficiency Virus Type 1 Antibody 2F5," Journal of Virology 78(6):3155-3161, American Society For Microbiology, United States (2004).
Office Action mailed Nov. 1, 2018, in U.S. Appl. No. 14/379,825, Igawa, T., et al., filed Aug. 20, 2014.
Office Action mailed Aug. 27, 2018, in U.S. Appl. No. 14/781,069, Mimoto, F., et al., filed Sep. 29, 2015.
Abelev, G. I., "Monoclonal Antibodies," Sorosovsky Education Journal, 1:16-20 (1998).
Colman, P. M., "Effects of amino acid sequence changes on antibody-antigen interactions," Res Immunol., 145:33-36 (1994).

Curtiss, F. R., Editor, "Selectivity and Specificity Are the Keys to Cost-Effective Use of Omalizumab for Allergic Asthma," JMCP, 11(9):774-776 (2005), submitted by opponents in oppositions in European Application Nos. EP2708558 and EP2708559 in Mar. 2020.
Expert Declaration of Joachim Boucneau, dated Mar. 11, 2020, submitted by opponents in oppositions in European Application Nos. EP2708558 and EP2708559 in Mar. 2020.
Edwards, B. M., et al., "The Remarkable Flexibility of the Human Antibody Repertoire; Isolation of Over One Thousand Different Antibodies to a Single Protein, BlyS," J Mol Biol., 334:103-118 (2003).
F. Hoffmann-La Roche Ltd. Media Release, "FDA grants supplemental approval for ACTEMRA," Jan. 5, 2011, 4 pages, submitted by opponents in oppositions in European Application Nos. EP2708558 and EP2708559 in Mar. 2020.
Guidance on the Use of International Nonproprietary Names (INNs) for Pharmaceutical Substances, World Health Organization, 2017, 55 pages, submitted by opponents in oppositions in European Application Nos. EP2708558 and EP2708559 in Mar. 2020.
Igawa, T., et al., "Sweeping antibody as a novel therapeutic antibody modality capable of eliminating soluble antigens from circulation," Immunol Rev., 270:132-151 (2016).
Kussie, P. H., et al., "A Single Engineered Amino Acid Substitution Changes Antibody Fine Specificity," J Immunol., 152:146-152 (1994).
Lloyd, C., et al., "Modelling the human immune response: performance of a $10^{11}$ human antibody repertoire against a broad panel of therapeutically relevant antigens," Prot Eng Des Sel., 22(3):159-168 (2009).
Mariuzza, R. A., et al., "The Structural Basis of Antigen-Antibody Recognition," Ann Rev Biophys Biophys Chem., 16:139-159 (1987).
Muramatsu, H., "Latent myostatin specific elimination by sweeping antibody® is a novel therapeutic approach to improve muscle strength," Neuromuscular Disorders, 29(Suppl 1):S86 (2019).
Rich, R. L., et al., "A global benchmark study using affinity-based biosensors," Anal Biochem., 386(2):194-216 (2009), submitted by opponents in oppositions in European Application Nos. EP2708558 and EP2708559 in Mar. 2020.
Van Assche, G., et al., "Adalimumab in Crohn's Disease," Biologics: Targets & Therapy, 1(4):355-365 (2007), submitted by opponents in oppositions in European Application Nos. EP2708558 and EP2708559 in Mar. 2020.
Wu, H., et al., "Humanization of a Murine Monoclonal Antibody by Simultaneous Optimization of Framework and CDR Residues," J Mol Biol., 294:151-162 (1999).
Yu, X., et al., "Development and Validation of a Cell-Based Fluorescent Method for Measuring Antibody Affinity," J Immunol Methods, 442:49-53 (2017), submitted by opponents in oppositions in European Application Nos. EP2708558 and EP2708559 in Mar. 2020.
Flores, M., et al., "Dominant Expression of the Inhibitory FcγRIIB Prevents Antigen Presentation by Murine Plasmacytoid Dendritic Cells," J Immunol., 183:7129-7139 (2009).
Howard, G. C. and Kaser, M. R., editors, "Making and Using Antibodies: A Practical Handbook," CRC Press, 157-177 (2007).
King, D. J., "Applications and Engineering of Monoclonal Antibodies," Taylor & Francis, 151-159, 162-164 (2005).
Mendez-Fernandez, Y. V., et al., "The inhibitory FcγRIIb modulates the inflammatory response and influences atherosclerosis in male $apoE^{-/-}$ mice," Atherosclerosis, 214(1):73-80 (2011).
Poosarla, V. G., et al., "Computational de novo Design of Antibodies binding to a Peptide with High Affinity," Biotechnol Bioeng., 114(6):1331-1342 (2017).
Raghavan, M., et al., "Analysis of the pH Dependence of the Neonatal Fc Receptor/Immunoglobulin G Interaction Using Antibody and Receptor Variants," Biochem., 34:14649-14657 (1995).
Roitt, et al., Immunology, Moscow, Mir, 373-374 (2000).
Singer, et al., Genes & Genomes, Moscow, Mir, 115-188 (1998).
Tackenberg, B., et al., "Impaired inhibitory Fcγ receptor IIB expression on B cells in chronic inflammatory demyelinating polyneuropathy," PNAS, 106(12):4788-4792 (2009).

(56) References Cited

OTHER PUBLICATIONS

Torres, M. and Casadevall, A., "The immunoglobulin constant region contributes to affinity and specificity," Trends in Immunology, 29(2):91-97 (2008).
Vaccaro, C., et al., "Engineering the Fc region of immunoglobulin G to modulate in vivo antibody levels," Nat Biotechnol., 23(10):1283-1288 (2005).
Yang, M., et al., "Effect of anti CD20 antibody Fab' fragment on apoptosis of B lymphoma cells and intracellular calcium," Tumor, 26(2):116-119 (2006).
Yarilin, A. A., Fundamentals of Immunology (Osnovy immunologii), Moscow, Medicina, 171 (1999).
Alignment Sequence 1047 and 30 dated Jan. 26, 2021, cited in corresponding European application Office Action dated Feb. 2, 2021.
Alignment Sequence 472 and 24 dated Jan. 26, 2021, cited in corresponding European application Office Action dated Feb. 2, 2021.
Almagro, J. C., et al., "Design and Validation of a Synthetic VH Repertoire with Tailored Diversity for Protein Recognition," Journal of Molecular Recognition, 19(5):413-422 (2006).
Annex 1 from opponent 2's submission of Jun. 7, 2018, cited by the opponent during opposition procedure of EP2202245 on May 19, 2020.
Annex 1—screenshots of Genetyx software, cited by the opponent during opposition procedure of EP2202245 on May 22, 2020.
Annex 2—Sections of the Genetyx manual pertaining to isoelectric point, cited by the opponent during opposition procedure of EP2202245 on May 22, 2020.
Annex 3—screenshots of the web-based calculator, cited by the opponent during opposition procedure of EP2202245 on May 22, 2020.
Antibodies in Example 29 of EP2202245, cited by the opponent during opposition procedure of EP2202245 on May 19, 2020.
Arduin, E., et al., "Highly reduced binding to high and low affinity mouse Fc gamma receptors by L234A/L235A and N297A Fc mutations engineered into mouse IgG2a," Mol Immunol., 63:456-463 (2015).
Bork, P., "Powers and Pitfalls in Sequence Analysis: the 70% Hurdle," Genome Research, 10(4):398-400 (2000).
Bowie, J. U., et al., "Deciphering the Message in Protein Sequences: Tolerance to Amino Acid Substitutions," Science, 247(4948):1306-1310 (1990).
Buckler, D. R., et al., "Antibody Drug Discovery" edited by Wood, C. R. London: Imperial College Press, Section 2.4. Library Selection, p. 49-57 (2012).
Burgess, W. H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J Cell Biol., 111:2129-2138 (1990).
Coloma, M. J., et al., "Design and Production of Novel Tetravalent Bispecific Antibodies," Nature Biotechnology 15(2):159-163, Nature America Publishing, United States (Feb. 1997).
Dagbay, K. B., "Structural basis of specific inhibition of extracellular activation of pro- or latent myostatin by the monoclonal antibody SRK-015," J Biol Chem., 295(16):5404-5418 (2020).
Datta-Mannan, A., et al., "FcRn affinity—pharmacokinetic relationship of five human IgG4 antibodies engineered for improved in vitro FcRn binding properties in cynomolgus monkeys," Drug Metab Dispos., 40(8):1545-1555 (2012).
Declaration of M. Hiroyasu dated Oct. 21, 2020, cited in the corresponding European application Office Action on Feb. 2, 2021.
Di Stefano, A., et al., "Role of Interleukin-8 in the Pathogenesis and Treatment of COPD," Chest, 126(3):676-678 (2004).
Example antibody family tree, attached to the written submission for Opposition against EP 2708559 on Mar. 12, 2020.
Fischer, N. and Leger, O., "Bispecific Antibodies: Molecules That Enable Novel Therapeutic Strategies," Pathobiology 74(1):3-14, Basel, Switzerland (2007).

Ho, M., et al., "In Vitro Antibody Evolution Targeting Germline Hot Spots to Increase Activity of an Anti-CD22 Immunotoxin," J Biol Chem., 280(1):607-617 (2005).
Jakubke, et al., "Physiochemical properties," Amino Acids, Peptides and Proteins, Moscow, Mir, 356-363 (1985).
Janeway, Jr., C. A. and Travers, P., "Immunobiology—The Immune System in Health and Disease," Third Edition, 3:1-3:11 (1997).
Kroetsch, A., et al., "Engineered pH-dependent recycling antibodies enhance elimination of Staphylococcal enterotoxin B superantigen in mice," MABS, 11(2):411-421 (2019).
Lazar, E., et al., "Transforming Growth Factor $\alpha$: Mutation of Aspartic Acid 47 and Leucine 48 Results in Different Biological Activities," Mol Cell Biol., 8(3):1247-1252 (1988).
Liberti, P. A., et al., "Antigenicity of Polypeptides (Poly-$\alpha$-amino Acids). Physicochemical Studies of a Calcium-Dependent Antigen-Antibody Reaction," Biochem., 10(9):1632-1639 (1971).
Muller, D. and Kontermann, E., "Bispecific Antibodies. In: Handbook of Therapeutic Antibodies" (ed. by S. Dübel), 2:345-378, Wiley-VCH, Weinheim (2007).
Nagaoaka, M. and Akaike, T., "Single amino acid substitution in the mouse IgG1 Fc region induces drastic enhancement of the affinity to protein A," Protein Eng., 16(4):243-245 (2003).
Opposition proceedings and prosecution of European Patent No. 2275443, published Jan. 19, 2011 (4,766 pages).
Patentee's submission dated Jul. 16, 2015 (Response to Search Report filed Jul. 16, 2015), submitted by the Opponent on May 6, 2020 in Opposition of EP2679681.
Patentee's explanation in the submission of Apr. 28, 2020 in Annex A made in the appeal case for EP 2552955.
Patentee's response to Article 94(3) EPC communication on EP 3521311 filed on Oct. 20, 2020.
Safdari, Y., et al., "Antibody humanization methods—a review and update," Biotechnol Genet Eng Rev., 29(2):175-186 (2013).
Schrama, D., et al., "Antibody targeted drugs as cancer therapeutics," Nat Rev Drug Discov., 5:147-159 (2006).
Sikkink, L. A., et al., "Biochemical and aggregation analysis of Bence Jones proteins from difference light chain diseases," Amyloid, 15(1):29-39 (2008).
Singer, M. and Berg, P., "Genes & Genomes," Moscow, Mir, 63-64, 67-70 (1998).
Stavenhagen, J. B., et al., "Enhancing the potency of therapeutic monoclonal antibodies via Fc optimization," Advan Enzyme Regul., 48:152-164 (2008).
Third-Party Submission Under 37 C.F.R. 1.290 submitted Jan. 17, 2019 in U.S. Appl. No. 15/952,951.
Third-Party Submission Under 37 C.F.R. 1.290 submitted Apr. 3, 2019 in U.S. Appl. No. 15/952,951.
Warmerdam, P. A. M., "The Human Low Affinity Immunoglobulin G Fc Receptor IIC Gene Is a Result of an Unequal Crossover Event," J Biol Chem., 268(10):7346-7349 (1993).
Yoon, S.O., et al., "Construction, Affinity Maturation, and Biological Characterization of an Anti-tumor-associated Glycoprotein-72 Humanized Antibody," The Journal of Biological Chemistry 281(11):6985-6992 (2006).
Zhang, Q., et al., "Monoclonal Antibodies as Therapeutic Agents in Oncology and Antibody Gene Therapy," Cell Research, 17(2):89-99 (2007).
Gershoni, J. M., et al., "Epitope Mapping—The First Step in Developing Epitope-Based Vaccines," Biodrugs, 21(3):145-156 (2007).
Wines, B. D., et al., "The IgG Fc Contains Distinct Fc Receptor (FcR) Binding Sites: The Leukocyte Receptors Fc$\gamma$RI and Fc$\gamma$RIIa Bind to a Region in the Fc Distinct from That Recognized by Neonatal FcR and Protein A," J Immunol., 164:5313-5318 (2000).
U.S. Appl. No. 08/765,783, filed Mar. 7, 1997, Matsushima, K., et al.
U.S. Appl. No. 12/295,039, filed Jan. 20, 2009, Igawa, T., et al., related application.
U.S. Appl. No. 12/936,587, filed Jan. 3, 2011, Igawa, T., et al., related application, now abandoned.
U.S. Appl. No. 13/595,139, filed Aug. 27, 2012, Igawa, T., et al., related application.
U.S. Appl. No. 13/889,484, filed May 8, 2013, Chugai Seiyaku Kabushiki Kaisha, related application.

(56) References Cited

OTHER PUBLICATIONS

U.S. Appl. No. 13/889,512, filed May 8, 2013, Chugai Seiyaku Kabushiki Kaisha, related application.
U.S. Appl. No. 13/990,158, filed Mar. 28, 2014, Igawa, T., et al., related application, now abandoned.
U.S. Appl. No. 14/001,218, filed Dec. 2, 2013, Mimoto, F., et al., related application.
U.S. Appl. No. 14/347,321, filed Mar. 26, 2014, Chugai Seiyaku Kabushiki Kaisha, related application, now abandoned.
U.S. Appl. No. 14/379,825, filed Aug. 20, 2014, Chugai Seiyaku Kabushiki Kaisha, related application.
U.S. Appl. No. 14/422,207, filed Feb. 18, 2015, Chugai Seiyaku Kabushiki Kaisha, related application.
U.S. Appl. No. 14/423,269, filed Feb. 23, 2015, Chugai Seiyaku Kabushiki Kaisha, related application.
U.S. Appl. No. 14/741,786, filed Jun. 17, 2015, Chugai Seiyaku Kabushiki Kaisha, related application.
U.S. Appl. No. 14/781,069, filed Sep. 29, 2015, Chugai Seiyaku Kabushiki Kaisha, related application.
U.S. Appl. No. 14/974,488, filed Dec. 18, 2015, Chugai Seiyaku Kabushiki Kaisha, related application.
U.S. Appl. No. 15/015,287, filed Feb. 4, 2016, Chugai Seiyaku Kabushiki Kaisha, related application.
U.S. Appl. No. 15/725,692, filed Oct. 5, 2017, Chugai Seiyaku Kabushiki Kaisha, related application.
U.S. Appl. No. 15/952,945, filed Apr. 13, 2018, Chugai Seiyaku Kabushiki Kaisha, related application.
U.S. Appl. No. 15/952,951, filed Apr. 13, 2018, Chugai Seiyaku Kabushiki Kaisha, related application.
U.S. Appl. No. 15/963,449, filed Apr. 26, 2018, Chugai Seiyaku Kabushiki Kaisha, related application.
U.S. Appl. No. 15/963,455, filed Apr. 26, 2018, Chugai Seiyaku Kabushiki Kaisha, related application.
U.S. Appl. No. 15/976,288, filed May 10, 2018, Chugai Seiyaku Kabushiki Kaisha, related application.
U.S. Appl. No. 15/988,348, filed May 24, 2018, Chugai Seiyaku Kabushiki Kaisha, related application.
U.S. Appl. No. 15/977,757, filed May 11, 2018, Chugai Seiyaku Kabushiki Kaisha, related, unpublished application.
U.S. Appl. No. 12/679,922, filed Oct. 1, 2010, Igawa, T., et al., related application.
U.S. Appl. No. 16/361,498, filed Mar. 22, 2019, Chugai Seiyaku Kabushiki Kaisha, related application.
U.S. Appl. No. 16/323,142, 371(c) date Feb. 4, 2019, Chugai Seiyaku Kabushiki Kaisha, et al., related application.
U.S. Appl. No. 16/697,310, filed Nov. 27, 2019, Chugai Seiyaku Kabushiki Kaisha, related application.
U.S. Appl. No. 08/341,560, filed Nov. 17, 1994, Ward, E. S., et al.
U.S. Appl. No. 08/484,891, filed Jun. 7, 1995, Connelly, S., et al.
U.S. Appl. No. 08/781,449, filed Jan. 10, 1997, Khawli, L. A., et al.
U.S. Appl. No. 08/905,293, filed Aug. 1, 1997, Rosok, M. J., et al.
U.S. Appl. No. 08/908,469, filed Aug. 6, 1997, Baca, M., et al.
U.S. Appl. No. 08/921,100, filed Aug. 29, 1997, Matsushima, K., et al.
U.S. Appl. No. 09/274,163, filed Mar. 22, 1999, Stevens, F. J., et al.
U.S. Appl. No. 09/339,596, filed Jun. 24, 1999, Co, M. S., et al.
U.S. Appl. No. 09/375,924, filed Aug. 17, 1999, Gallo, M., et al.
U.S. Appl. No. 09/416,557, filed Oct. 12, 1999, Matsushima, K., et al.
U.S. Appl. No. 09/450,520, filed Nov. 29, 1999, Vasquez, M., et al.
U.S. Appl. No. 09/483,588, filed Jan. 14, 2000, Presta, L.
U.S. Appl. No. 09/509,098, 371(c) date Mar. 22, 2000, Tsuchiya, M.
U.S. Appl. No. 09/647,468, 371(c) date Sep. 29, 2000, Sato, K., et al.
U.S. Appl. No. 09/730,857, filed Dec. 7, 2000, Matsushima, K., et al.
U.S. Appl. No. 09/880,748, filed Jun. 15, 2001, Ruben, S. M., et al.
U.S. Appl. No. 09/933,497, filed Aug. 20, 2001, Ward, E. S.
U.S. Appl. No. 09/956,206, filed Sep. 17, 2001, do Couto, F. J. R., et al.
U.S. Appl. No. 10/029,988, filed Dec. 31, 2001, Levanon, A., et al.
U.S. Appl. No. 10/032,037, filed Dec. 31, 2001, Levanon, A., et al.
U.S. Appl. No. 10/032,423, filed Dec. 31, 2001, Lazarovits, J., et al.
U.S. Appl. No. 10/364,953, filed Feb. 11, 2003, Lowman, H. B., et al.
U.S. Appl. No. 10/379,392, filed Mar. 3, 2003, Lazar, G. A., et al.
U.S. Appl. No. 10/474,832, 371(c) date Oct. 14, 2003, Lyne, P. D., et al.
U.S. Appl. No. 10/481,524, filed Jun. 30, 2004, Aburatani, H., et al.
U.S. Appl. No. 10/514,516, filed Oct. 28, 2005, Edwards, C., et al.
U.S. Appl. No. 10/575,193, 371(c) date Oct. 24, 2006, Hattori, K., et al.
U.S. Appl. No. 10/576,372, 371(c) date Apr. 19, 2006, Rossi, M., et al.
U.S. Appl. No. 10/672,280, filed Sep. 26, 2003, Lazar, G. A., et al.
U.S. Appl. No. 10/688,925, filed Oct. 21, 2003, Veldman, G. M., et al.
U.S. Appl. No. 10/723,434, filed Nov. 26, 2003, Zhong, P., et al.
U.S. Appl. No. 10/738,120, filed Dec. 16, 2004, Teeling, J., et al.
U.S. Appl. No. 10/822,231, filed Mar. 26, 2004, Lazar, G. A., et al.
U.S. Appl. No. 10/822,300, filed Apr. 9, 2004, Hinton, P. R., et al.
U.S. Appl. No. 10/861,049, filed Jun. 4, 2004, Chan, A., et al.
U.S. Appl. No. 10/902,588, filed Jul. 28, 2004, Stavenhagen, J., et al.
U.S. Appl. No. 10/902,682, filed Jul. 29, 2004, Rabbani, E., et al.
U.S. Appl. No. 11/089,426, filed Mar. 24, 2005, Gillies, S. D., et al.
U.S. Appl. No. 11/090,981, filed Mar. 24, 2005, Lazar, G. A., et al.
U.S. Appl. No. 11/094,625, filed Mar. 30, 2005, Datta, D., et al.
U.S. Appl. No. 11/108,135, filed Apr. 15, 2005, Koenig, S., et al.
U.S. Appl. No. 11/149,309, filed Jun. 9, 2005, Kasaian, M. T., et al.
U.S. Appl. No. 11/155,909, filed Jun. 17, 2005, Cho, H. S., et al.
U.S. Appl. No. 11/165,023, filed Jun. 24, 2005, Dall'Acqua, W., et al.
U.S. Appl. No. 11/397,328, filed Apr. 3, 2006, Dall'Acqua, W., et al.
U.S. Appl. No. 11/429,793, filed May 8, 2006, Presta, L.
U.S. Appl. No. 11/432,872, filed May 12, 2006, Farrington, G. K., et al.
U.S. Appl. No. 11/483,250, filed Jul. 7, 2006, Lazar, G. A., et al.
U.S. Appl. No. 11/499,064, filed Aug. 3, 2006, Kambadur, R., et al.
U.S. Appl. No. 11/520,121, filed Sep. 13, 2006, Presta, L.
U.S. Appl. No. 11/536,603, filed Sep. 28, 2006, Baca, M., et al.
U.S. Appl. No. 11/557,466, filed Jul. 12, 2007, Dennis, M. S., et al.
U.S. Appl. No. 11/585,172, filed Oct. 24, 2006, Kishimoto, T., et al.
U.S. Appl. No. 11/713,577, filed Feb. 28, 2007, Krummen, L. A., et al.
U.S. Appl. No. 11/754,015, filed May 25, 2007, Johnson, L. S., et al.
U.S. Appl. No. 11/764,001, filed Jun. 15, 2007, Lazar, G. A., et al.
U.S. Appl. No. 11/765,353, filed Jun. 19, 2007, Lazar, G. A., et al.
U.S. Appl. No. 11/793,649, 371(c) date Jun. 21, 2007, Tsuchiya, M., et al.
U.S. Appl. No. 11/911,940, 371(c) date Apr. 16, 2008, Babcook, J., et al.
U.S. Appl. No. 11/929,742, filed Oct. 30, 2007, Lazar, G. A., et al.
U.S. Appl. No. 11/932,151, filed Oct. 31, 2007, Chamberlain, A. K., et al.
U.S. Appl. No. 11/952,568, filed Dec. 7, 2007, Stavenhagen, J. B., et al.
U.S. Appl. No. 12/018,754, filed Jan. 23, 2008, Bernett, M. J., et al.
U.S. Appl. No. 12/020,443, filed Jan. 25, 2008, Lazar, G. A., et al.
U.S. Appl. No. 12/033,642, filed Feb. 19, 2008, Presta, L.
U.S. Appl. No. 12/147,379, filed Jun. 26, 2008, Datta, D., et al.
U.S. Appl. No. 12/156,183, filed May 30, 2008, Chu, S. Y., et al.
U.S. Appl. No. 12/186,058, filed Aug. 5, 2008, Koenig, S., et al.
U.S. Appl. No. 12/295,075, 371(c) date Apr. 20, 2009, Igawa, T., et al.
U.S. Appl. No. 12/311,768, 371(c) date Feb. 22, 2010, Lasters, I. J. I., et al.
U.S. Appl. No. 12/532,022, 371(c) date Sep. 18, 2009, Guler-Gane, G., et al.
U.S. Appl. No. 12/559,411, filed Sep. 14, 2009, Hariharan, K., et al.
U.S. Appl. No. 12/559,415, filed Sep. 14, 2009, Hariharan, K., et al.

(56) References Cited

OTHER PUBLICATIONS

U.S. Appl. No. 12/577,967, filed Oct. 13, 2009, Lowman, H. B., et al.
U.S. Appl. No. 12/611,090, filed Nov. 2, 2009, Kim, M., et al.
U.S. Appl. No. 12/660,528, filed Feb. 26, 2010, Sabbadini, R. A.
U.S. Appl. No. 12/673,599, 371(c) date Feb. 16, 2010, Clegg, S. J., et al.
U.S. Appl. No. 12/680,082, 371(c) date Jun. 25, 2010, Igawa, T., et al.
U.S. Appl. No. 12/680,087, 371(c) date Jan. 3, 2011, Igawa, T., et al.
U.S. Appl. No. 12/680,112, 371(c) date Jun. 23, 2010, Igawa T., et al.
U.S. Appl. No. 12/733,865, 371(c) date Mar. 23, 2010, Chung, Y. M., et al.
U.S. Appl. No. 12/733,933, 371(c) date Jun. 3, 2010, Igawa, T., et al.
U.S. Appl. No. 12/792,810, filed Jun. 3, 2010, Bohrmann, B., et al.
U.S. Appl. No. 12/809,563, 371(c) date Jun. 18, 2010, Biere-Citron, A. L., et al.
U.S. Appl. No. 12/864,075, 371(c) date Oct. 6, 2010, Bernett, M. J., et al.
U.S. Appl. No. 12/896,610, filed Oct. 1, 2010, Lazar, G. A., et al.
U.S. Appl. No. 12/913,145, filed Oct. 27, 2010, Finney, H. M., et al.
U.S. Appl. No. 12/990,137, 371(c) date Feb. 11, 2011, Foltz, I., et al.
U.S. Appl. No. 13/045,345, filed Mar. 10, 2011, Pons, J., et al.
U.S. Appl. No. 13/077,644, filed Mar. 31, 2011, Beliard, R., et al.
U.S. Appl. No. 13/174,423, filed Jun. 30, 2011, Jackson, S. M., et al.
U.S. Appl. No. 13/192,429, filed Jul. 27, 2011, Dall'Acqua, W., et al.
U.S. Appl. No. 13/194,904, filed Jul. 29, 2011, Dahiyat, B. I., et al.
U.S. Appl. No. 13/388,270, 371(c) date Apr. 10, 2012, Schebye, X. M., et al.
U.S. Appl. No. 13/422,887, filed Mar. 16, 2012, Jackson, S. M., et al.
U.S. Appl. No. 13/458,730, filed Apr. 27, 2012, Zhang, Y., et al.
U.S. Appl. No. 13/637,415, 371(c) date Feb. 4, 2013, Igawa, T., et al.
U.S. Appl. No. 13/764,693, filed Feb. 11, 2013, Lazar, G. A., et al.
U.S. Appl. No. 13/791,312, filed Mar. 8, 2013, Grabstein, K., et al.
U.S. Appl. No. 13/795,674, filed Mar. 12, 2013, Alderbio Holdings LLC.
U.S. Appl. No. 13/816,894, 371(c) date Apr. 29, 2013, Han, H., et al.
U.S. Appl. No. 13/832,247, filed Mar. 15, 2013, Regeneron Pharmaceuticals, Inc.
U.S. Appl. No. 13/855,448, filed Apr. 2, 2013, Regeneron Pharmaceuticals, Inc.
U.S. Appl. No. 13/918,751, filed Jun. 14, 2013, Lazar, G. A., et al.
U.S. Appl. No. 13/964,159, filed Aug. 12, 2013, Regeneron Pharmaceuticals, Inc.
U.S. Appl. No. 137,117, 371(c) date Dec. 20, 1993, Tsuchiya, M., et al.
U.S. Appl. No. 139,504, filed Dec. 30, 1987, Ngo, T. T.
U.S. Appl. No. 14/007,947, 371(c) date Dec. 30, 2013, Igawa, T., et al.
U.S. Appl. No. 14/021,777, filed Sep. 9, 2013, Neotope Biosciences Ltd.
U.S. Appl. No. 14/078,501, filed Nov. 12, 2013, Xencor, Inc.
U.S. Appl. No. 14/085,424, filed Nov. 20, 2013, Regeneron Pharmaceuticals, Inc.
U.S. Appl. No. 14/127,576, 371(c) date Mar. 13, 2014, Mimoto, F., et al.
U.S. Appl. No. 14/155,344, filed Jan. 14, 2014, Xencor, Inc.
U.S. Appl. No. 14/165,487, filed Jan. 27, 2014, Xencor, Inc.
U.S. Appl. No. 14/212,189, filed Mar. 14, 2014, Alderbio Holdings LLC.
U.S. Appl. No. 14/216,705, filed Mar. 17, 2014, Moore, G., et al.
U.S. Appl. No. 14/290,544, filed May 29, 2014, Regeneron Pharmaceuticals, Inc.
U.S. Appl. No. 14/340,872, filed Jul. 25, 2014, CytomX Therapeutics, Inc.
U.S. Appl. No. 14/347,034, 371(c) date Mar. 25, 2014, Chugai Seiyaku Kabushiki Kaisha.
U.S. Appl. No. 14/347,187, 371(c) date Jul. 25, 2014, Chugai Seiyaku Kabushiki Kaisha.
U.S. Appl. No. 14/349,884, 371(c) date Apr. 4, 2014, Chugai Seiyaku Kabushiki Kaisha.
U.S. Appl. No. 14/361,013, 371(c) date May 28, 2014, Chugai Seiyaku Kabushiki Kaisha.
U.S. Appl. No. 14/377,556, 371(c) date Aug. 8, 2014, Chugai Seiyaku Kabushiki Kaisha.
U.S. Appl. No. 14/402,574, 371(c) date Nov. 20, 2014, Chugai Seiyaku Kabushiki Kaisha.
U.S. Appl. No. 14/404,051, 371(c) date Nov. 26, 2014, Chugai Seiyaku Kabushiki Kaisha.
U.S. Appl. No. 14/406,232, 371(c) date Dec. 8, 2014, Chugai Seiyaku Kabushiki Kaisha.
U.S. Appl. No. 14/629,967, filed Feb. 24, 2015, Chugai Seiyaku Kabushiki Kaisha.
U.S. Appl. No. 14/641,026, filed Mar. 6, 2015, Alexion Pharmaceuticals, Inc.
U.S. Appl. No. 14/654,895, 371(c) date Jun. 23, 2015, Chugai Seiyaku Kabushiki Kaisha.
U.S. Appl. No. 14/717,914, filed May 20, 2015, Regeneron Pharmaceuticals, Inc.
U.S. Appl. No. 14/727,313, filed Jun. 1, 2015, Alexion Pharmaceuticals, Inc.
U.S. Appl. No. 15/050,145, filed Feb. 22, 2016, Chugai Seiyaku Kabushiki Kaisha.
U.S. Appl. No. 15/210,360, filed Jul. 14, 2016, Chugai Seiyaku Kabushiki Kaisha.
U.S. Appl. No. 15/230,904, filed Aug. 8, 2016, Chugai Seiyaku Kabushiki Kaisha.
U.S. Appl. No. 15/393,380, filed Dec. 29, 2016, Svensson, C., et al.
U.S. Appl. No. 157,273, filed Feb. 17, 1988, Morgan, Jr., A. C., et al.
U.S. Appl. No. 472,523, filed Jun. 7, 1995, Raso, V. A., et al.
U.S. Appl. No. 477,728, filed Jun. 7, 1995, Queen, C. L., et al.
U.S. Appl. No. 534,658, filed Sep. 22, 1983, Insel, R. A., et al.
U.S. Appl. No. 730,040, filed Jul. 12, 1991, Esmon, C. T., et al.
U.S. Appl. No. 942,245, filed Sep. 9, 1992, Pederson, J. T., et al.
U.S. Appl. No. 998,754, filed Dec. 28, 1992, Raso, V. A.
U.S. Appl. No. 17/020,497, filed Sep. 14, 2020, Igawa, T., et al., related application.
U.S. Appl. No. 17/020,543, filed Sep. 14, 2020, Igawa, T., et al., related application.
U.S. Appl. No. 17/028,210, filed Sep. 22, 2020, Katada, H., et al., related application.
U.S. Appl. No. 09/956,968, filed Sep. 21, 2001, Ye.
U.S. Appl. No. 11/124,620, filed May 5, 2005, Lazar et al.
U.S. Appl. No. 11/436,266, filed May 17, 2006, Chamberlain et al.
U.S. Appl. No. 11/981,647, filed Oct. 31, 2007, Desjarlais et al.
U.S. Appl. No. 16/108,897, filed Aug. 22, 2018, Igawa et al.
U.S. Appl. No. 16/889,066, filed Jun. 1, 2020, Ruike et al., related application.
U.S. Appl. No. 17/333,256, filed May 28, 2021, Kakiuchi et al., related application.
U.S. Appl. No. 17/854,023, filed Jul. 7, 2022, Igawa et al., related application.
Anchin, J. M., et al., "Recognition of Superpotent Sweetener Ligands by a Library of Monoclonal Antibodies," J Mol Recognit., 10(5):235-242 (1997).
Anderson, C.L., et al., "Perspective-FcRn Transports Albumin: Relevance to Immunology and Medicine," Trends Immunol., 27(7):343-348 (2006).
Bazin, R., et al., "Use of hu-IgG-SCID Mice to Evaluate the in Vivo Stability of Human Monoclonal IgG Antibodies," J Immunol Methods, 172(2):209-217 (1994).
Birn, H., et al., "Renal Albumin Absorption in Physiology and Pathology," Kidney Int'l, 69(3):440-449 (2006).

(56) References Cited

OTHER PUBLICATIONS

Chaudhury, C., et al., "The Major Histocompatibility Complex-related Fc Receptor for Igg (FcRn) Binds Albumin and Prolongs Its Lifespan," J Exp Med., 197(3):315-322 (2003).
Chilukuri, N., et al., "Polyethylene Glycosylation Prolongs the Circulatory Stability of Recombinant Human Butyrylcholinesterase," Chem-Biol Interact., 157-158:115-121 (2005).
Chinese Medicated Bath Encyclopedia-Take Medicated Bath without Getting Sick, Editor-in-chief: Junxia Xu, p. 177 (2013).
Chuang, V.T.G., et al., "Pharmaceutical Strategies Utilizing Recombinant Human Serum Albumin," Pharm Res., 19(5):569-577 (2002).
Crowe, J.S., et al., "Humanized Monoclonal Antibody CAMPATH-1H: Myeloma Cell Expression of Genomic Constructs, Nucleotide Sequence of cDNA Constructs and Comparison of Effector Mechanisms of Myeloma and Chinese Hamster Ovary Cell-derived Material," Clin Exp Immunol., 87(1):105-110 (1992).
Deng, R., et al., "Pharmacokinetics of Humanized Monoclonal Anti-tumor Necrosis Factor-{alpha} Antibody and Its Neonatal Fc Receptor Variants in Mice and Cynomolgus Monkeys," Drug Metabolism and Disposition, 38(4):600-605 (2010).
Dennis, M.S., et al., "Albumin Binding as a General Strategy for Improving the Pharmacokinetics of Proteins," J Biol Chem., 277(38):35035-35043 (2002).
Dirnberger, D., et al., "Secretion of Biologically Active Glycoforms of Bovine Follicle Stimulating Hormone in Plants," Eur J Biochem., 268(16):4570-4579 (2001).
Franks, F., "Conformational Stability of Proteins," Chapter 11 in Protein Biotechnology, 395-436 (1993).
Gekle, M., "Renal Tubule Albumin Transport," Annual Review of Physiology, 67:573-594 (2005).
Guasch, A., et al., "Charge Selectivity of the Glomerular Filtration Barrier in Healthy and Nephrotic Humans," J Clin Invest., 92(5):2274-2282 (1993).
Holt, L.J., et al., "Anti-Serum Albumin Domain Antibodies for Extending the Half-Lives of Short Lived Drugs," Protein Eng Des Sel., 21(5):283-288 (2008).
Huang, S., et al., "Fully Humanized Neutralizing Antibodies to Interleukin-8 (ABX-IL8) Inhibit Angiogenesis, Tumor Growth, and Metastasis of Human Melanoma," Amer J Pathol., 161(1):125-134 (2002).
Huang, Y.J., et al., "Recombinant Human Butyrylcholinesterase From Milk of Transgenic Animals to Protect Against Organophosphate Poisoning," PNAS, 104(34):13603-13608 (2007).
Inoue, M., et al., "Synthesis of a Superoxide Dismutase Derivative That Circulates Bound to Albumin and Accumulates in Tissues Whose pH Is Decreased," Biochemistry, 28(16):6619-6624 (1989).
James, L.C., et al., "1.9 A Structure of the Therapeutic Antibody CAMPATH-1H Fab in Complex with a Synthetic Peptide Antigen," Journal of Molecular Biology, 289(2):293-301 (1999).
Janeway, C.A., et al., "The Immune System in Health and Disease," Immunobiology, 5th Edition, 122 (2001).
Kawamoto, M., "Circulatory Stability and Plasma Lidocaine Levels During Continuous and Intermittent Thoracic Epidural Analgesia," J Anesth., 5(2):166-171 (1991).
Kim, H.J., et al., "The Glycosylation and Pharmacokinetics of CTLA4Ig Produced in Rice Cells," Biol Pharm Bulletin, 30(10):1913-1917 (2007).
King, D.J., "Applications and Engineering of Monoclonal Antibodies," Bioscience, 68-71 (1998).
Klein, C., et al., "Epitope interactions of monoclonal antibodies targeting CD20 and their relationship to functional properties," mAbs, 5(1):22-33 (2013).
Knudsen, L.B., et al., "Potent Derivatives of Glucagon-Like Peptide-1 with Pharmacokinetic Properties Suitable for Once Daily Administration," J Med Chem., 43(9):1664-1669 (2000).
Kratz, J., "Albumin as a Drug Carrier: Design of Prodrugs, Drug Conjugates and Nanoparticles," J Control Release, 132(3):171-183 (2008).
Kurtzhals, P., et al., "Albumin Binding and Time Action of Acylated Insulins in Various Species," J Pharm Sci., 85(3):304-308 (1996).
Kurtzhals, P., et al., "Effect of Fatty Acids and Selected Drugs on the Albumin Binding of a Long-Acting, Acylated Insulin Analogue," J Pharm Sci., 86(12):1365-1368 (1997).
Latres, E., et al., "Myostatin blockade with a fully human monoclonal antibody induces muscle hypertrophy and reverses muscle atrophy in young and aged mice," Skelet Muscle, 5:34 (2015).
Makrides, S.C., et al., "Extended in Vivo Half-Life of Human Soluble Complement Receptor Type 1 Fused to a Serum Albumin-Binding Receptor," J Pharmacol Exp Therapeut., 277(1):534-542 (1996).
Manning, M.C., et al., "Stability of Protein Pharmaceuticals," Pharm Res., 6(11):903-918 (1989).
O'Hear, C.E., et al., "Antibody Buffering of a Ligand in Vivo," PNAS, 102(1):40-44 (2005).
Pérez De La Lastra, J. M., et al., "Epitope mapping of 10 monoclonal antibodies against the pig analogue of human membrane cofactor protein (MCP)," Immunol., 96(4):663-670 (1999).
Peters, Jr., T., "All About Albumin—Biochemistry, Genetics, and Medical Applications," Academic Press, 76-79 (1996).
Petkova, S.B., et al., "Enhanced Half-life of Genetically Engineered Human IgG1 Antibodies in a Humanized FcRn Mouse Model: Potential Application in Humorally Mediated Autoimmune Disease," Int Immunol., 18(12):1759-1769 (2006).
Product Labelling Information for Rituxan (Rituximab), Nov. 1997.
Rehlaender, B.N., et al., "Antibodies as Carrier Proteins," Pharm Res., 15(11):1652-1656 (1998).
Saxena, A., et al., "Role of Oligosaccharides in the Pharmacokinetics of Tissue-Derived and Genetically Engineered Cholinesterases," Mol Pharmacol., 53(1):112-122 (1998).
Schultze, H.E., et al., "Turnover of Plasma Proteins," Molecular Biology of Human Proteins with Special Reference to Plasma Proteins, Nature and Metabolism of Extracellular Proteins, 1:476-477 (1996).
Singer, et al., "Genes & Genomes," 67-70 (1991).
Smith, B.J., et al., "Prolonged in Vivo Residence Times of Antibody Fragments Associated With Albumin," Bioconj Chem., 12(5):750-756 (2001).
Stork, R., et al., "A Novel Tri-Functional Antibody Fusion Protein With Improved Pharmacokinetic Properties Generated by Fusing a Bispecific Single-chain Diabody With an Albumin-binding Domain From Streptococcal Protein G," Protein Eng Des Sel., 20(11):569-576 (2007).
Zwolak, A., et al., "Rapid Purification of Human Bispecific Antibodies via Selective Modulation of Protein A Binding," Sci Rep., 7:15521 (2017).
U.S. Appl. No. 14/974,350, filed Dec. 18, 2015, Ruike et al., related application.
U.S. Appl. No. 15/379,597, filed Dec. 15, 2016, Shusta et al.
U.S. Appl. No. 15/544,930, filed Jul. 20, 2017, Murata et al., related application.
U.S. Appl. No. 15/688,004, filed Aug. 28, 2017, Ruike et al., related application.
U.S. Appl. No. 16/019,752, filed Jun. 27, 2018, Ruike et al., related application.
U.S. Appl. No. 16/065,192, filed Jun. 22, 2018, Ruike et al., related application.
U.S. Appl. No. 16/480,047, filed Jul. 23, 2019, Shinomiya et al., related application.
U.S. Appl. No. 16/514,467, filed Jul. 17, 2019, Ruike et al., related application.
U.S. Appl. No. 16/928,129, filed Jul. 14, 2020, Shinomiya et al., related application.
U.S. Appl. No. 17/263,691, filed Jan. 27, 2021, Shinomiya et al., related application.
U.S. Appl. No. 17/359,867, filed Jun. 28, 2021, Igawa et al., related application.
U.S. Appl. No. 17/494,199, filed Oct. 5, 2021, Igawa et al., related application.
U.S. Appl. No. 17/561,207, filed Dec. 23, 2021, Igawa et al., related application.
U.S. Appl. No. 17/578,524, filed Jan. 19, 2022, Igawa et al., related application.

(56) References Cited

OTHER PUBLICATIONS

U.S. Appl. No. 17/602,196, filed Jul. 10, 2021, Wakabayashi et al., related application.
U.S. Appl. No. 17/671,185, filed Feb. 14, 2022, Mimoto et al., related application.
U.S. Appl. No. 17/846,672, filed Jun. 22, 2022, Mimoto et al., related application.
U.S. Appl. No. 18/059,677, filed Nov. 29, 2022, Murata et al., related application.
U.S. Appl. No. 18/156,138, filed Jan. 18, 2023, Igawa et al., related application.
U.S. Appl. No. 18/157,320, filed Jan. 20, 2023, Ruike et al., related application.
U.S. Appl. No. 18/181,641, filed Mar. 10, 2023, Shinomiya et al., related application.
U.S. Appl. No. 18/390,581, filed Dec. 20, 2023, Igawa et al., related application.
U.S. Appl. No. 18/425,859, filed Jan. 29, 2024, Igawa et al., related application.
U.S. Appl. No. 18/432,567, filed Feb. 5, 2024, Igawa et al., related application.
U.S. Appl. No. 18/450,863, filed Aug. 16, 2023, Kakiuchi et al., related application.

\* cited by examiner

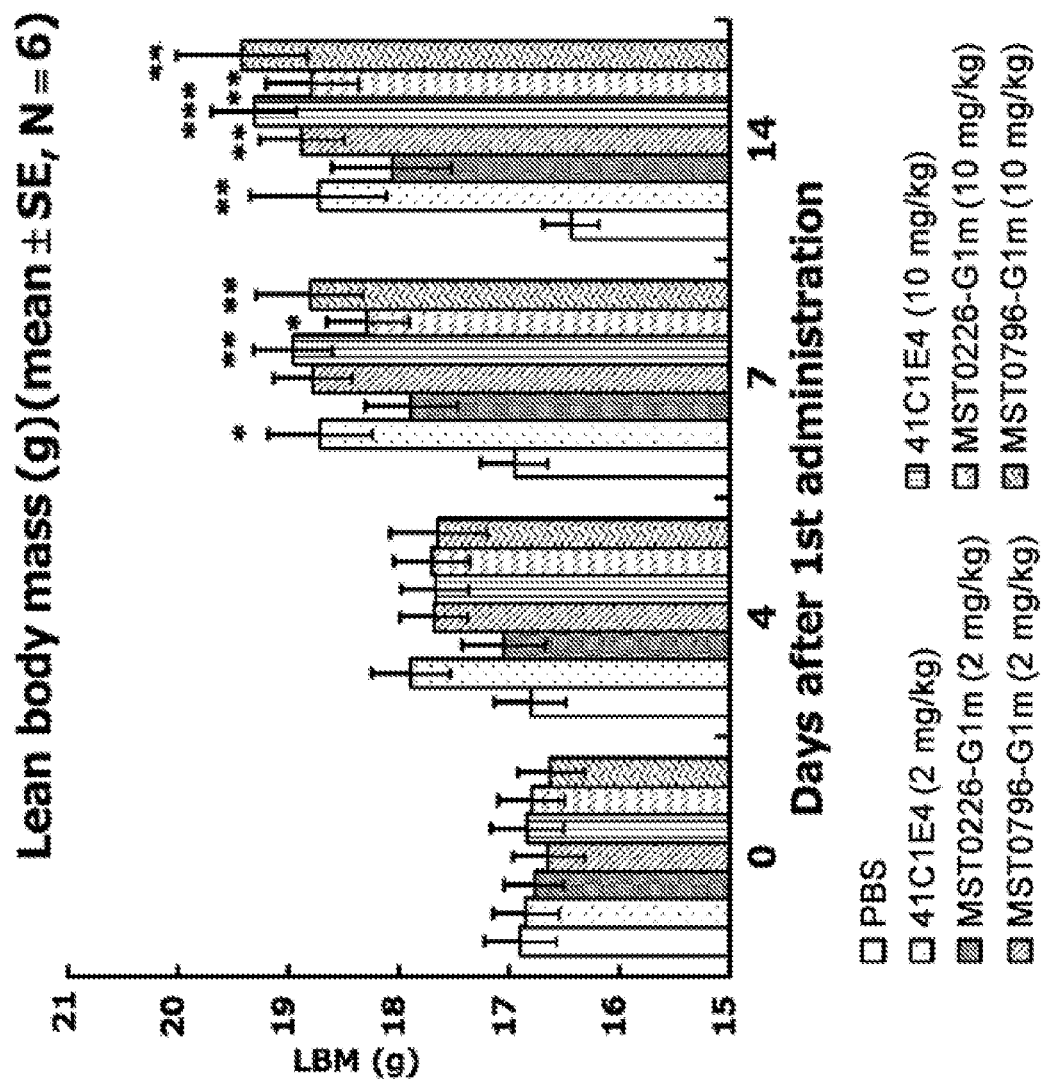

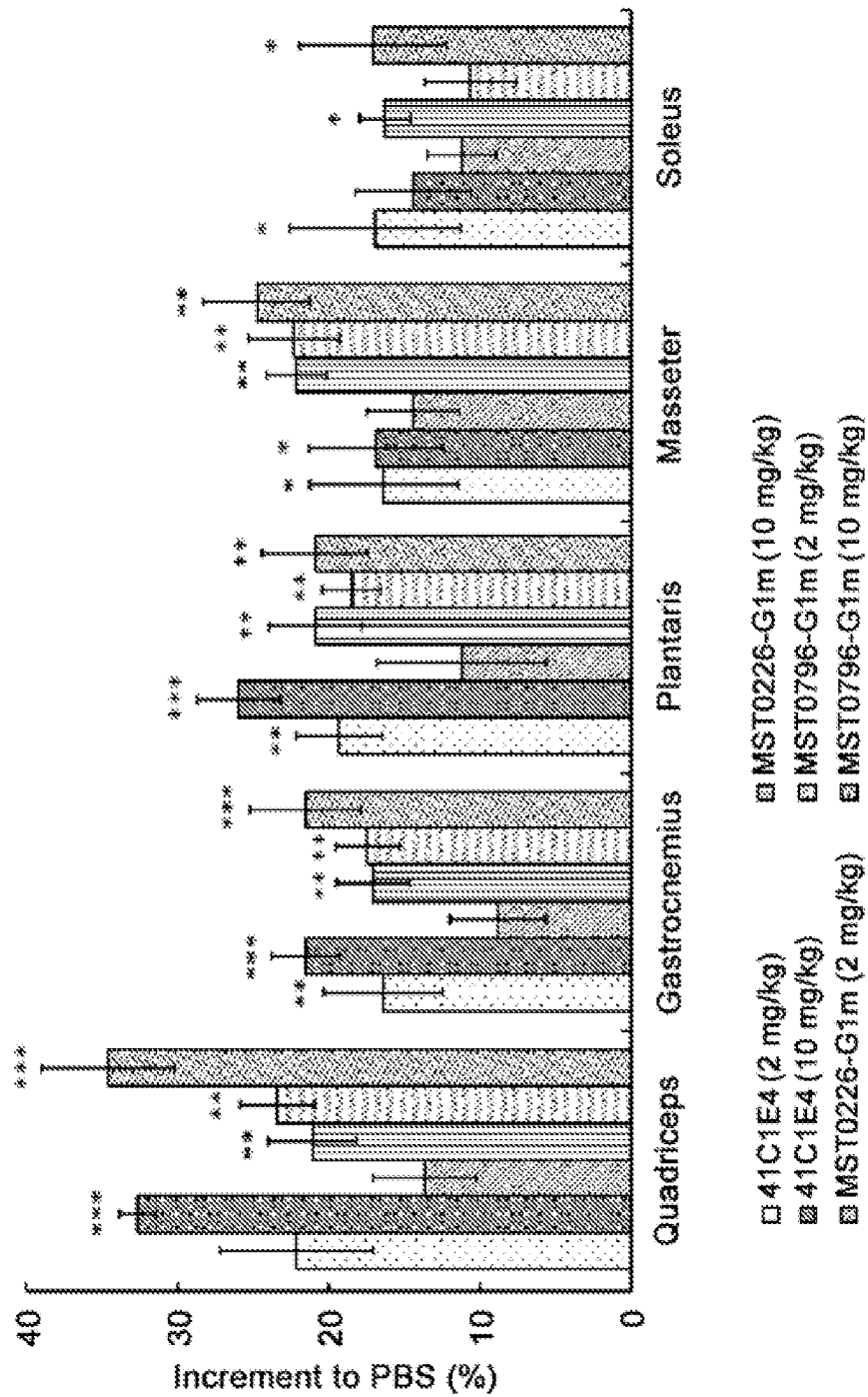

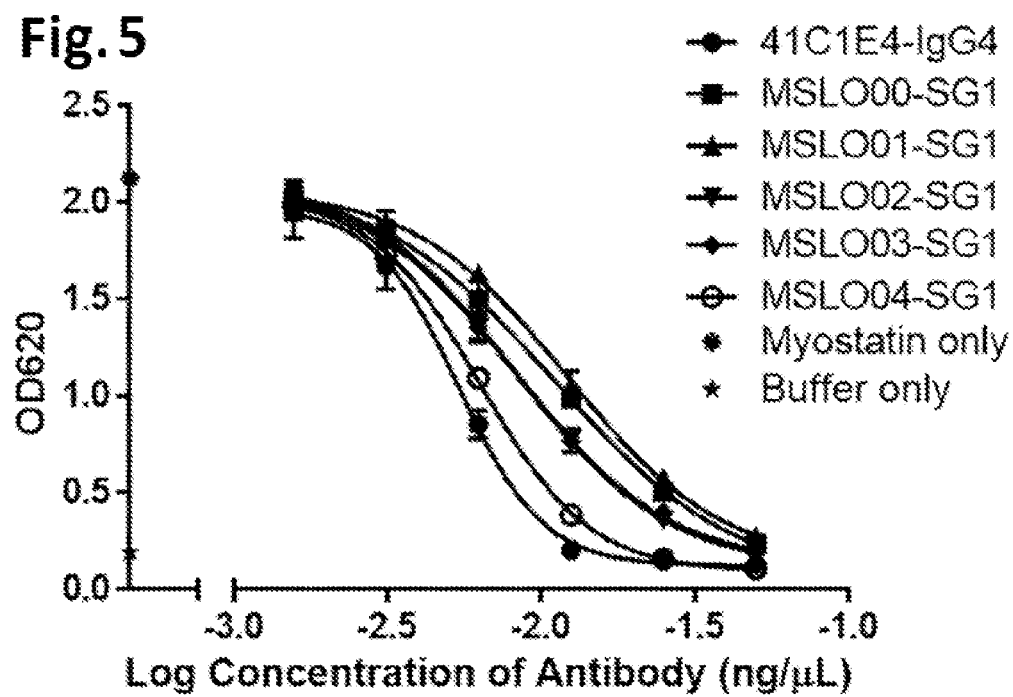

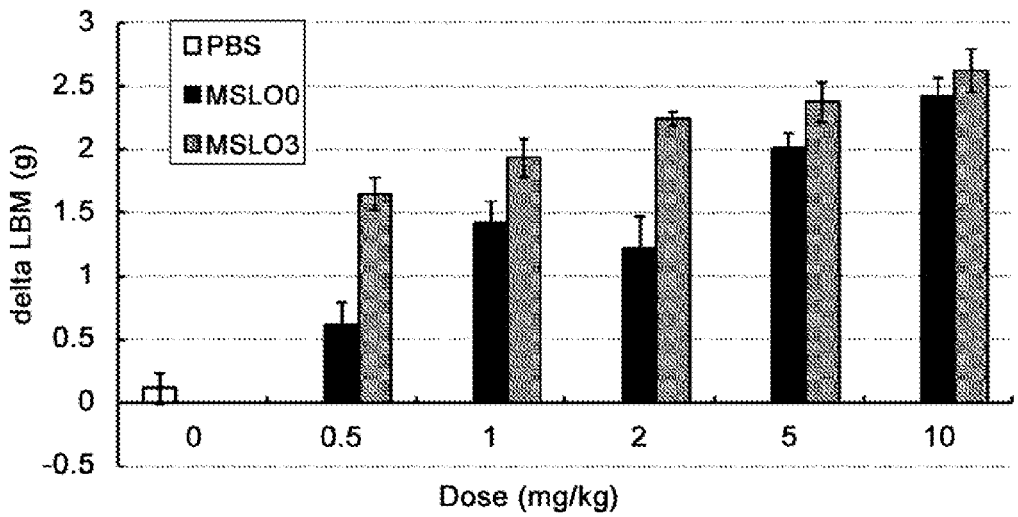
Fig. 7  delta LBM (g) (Day 0-14, mean±SE, N = 6)
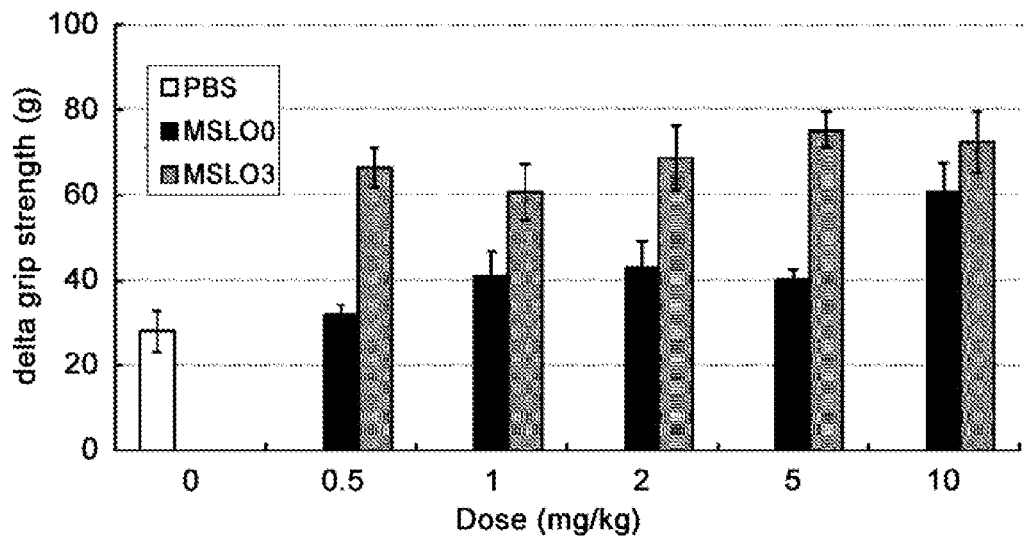
Fig. 8  delta grip strength (g) (Day -1-13, mean±SE, N = 6)

SEQUENCE LISTING

```
<160> NUMBER OF SEQ ID NOS: 102

<210> SEQ ID NO 1
<211> LENGTH: 375
<212> TYPE: PRT
<213> ORGANISM: Homo sapiens
```

```
<400> SEQUENCE: 1

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
370                 375

<210> SEQ ID NO 2
<211> LENGTH: 109
<212> TYPE: PRT
<213> ORGANISM: Homo sapiens
```

<400> SEQUENCE: 2

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
50              55                  60

Asn Pro Arg Gly Ser Ala Gly Pro Cys Cys Thr Pro Thr Lys Met Ser
65              70                  75                  80

Pro Ile Asn Met Leu Tyr Phe Asn Gly Lys Glu Gln Ile Ile Tyr Gly
            85                  90                  95

Lys Ile Pro Ala Met Val Val Asp Arg Cys Gly Cys Ser
            100                 105

<210> SEQ ID NO 3
<211> LENGTH: 375
<212> TYPE: PRT
<213> ORGANISM: Macaca fascicularis

<400> SEQUENCE: 3

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
50              55                  60

Arg Leu Glu Thr Ala Pro Asn Ile Ser Lys Asp Ala Ile Arg Gln Leu
65              70                  75                  80

Leu Pro Lys Ala Pro Pro Leu Arg Glu Leu Ile Asp Gln Tyr Asp Val
            85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
130             135                 140

Lys Ile Gln Tyr Asn Lys Val Val Lys Ala Gln Leu Trp Ile Tyr Leu
145             150                 155                 160

Arg Pro Val Glu Thr Pro Thr Thr Val Phe Val Gln Ile Leu Arg Leu
            165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
210             215                 220

Ile Glu Ile Lys Ala Leu Asp Glu Asn Gly His Asp Leu Ala Val Thr
225             230                 235                 240

Phe Pro Gly Pro Gly Glu Asp Gly Leu Asn Pro Phe Leu Glu Val Lys
            245                 250                 255

```
Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
            290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Ala Met Val
                355                 360                 365

Val Asp Arg Cys Gly Cys Ser
                370                 375

<210> SEQ ID NO 4
<211> LENGTH: 109
<212> TYPE: PRT
<213> ORGANISM: Macaca fascicularis

<400> SEQUENCE: 4

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 5
<211> LENGTH: 376
<212> TYPE: PRT
<213> ORGANISM: Mus musculus

<400> SEQUENCE: 5

Met Met Gln Lys Leu Gln Met Tyr Val Tyr Ile Tyr Leu Phe Met Leu
1               5                   10                  15

Ile Ala Ala Gly Pro Val Asp Leu Asn Glu Gly Ser Glu Arg Glu Glu
            20                  25                  30

Asn Val Glu Lys Glu Gly Leu Cys Asn Ala Cys Ala Trp Arg Gln Asn
        35                  40                  45

Thr Arg Tyr Ser Arg Ile Glu Ala Ile Lys Ile Gln Ile Leu Ser Lys
    50                  55                  60

Leu Arg Leu Glu Thr Ala Pro Asn Ile Ser Lys Asp Ala Ile Arg Gln
65                  70                  75                  80

Leu Leu Pro Arg Ala Pro Pro Leu Arg Glu Leu Ile Asp Gln Tyr Asp
                85                  90                  95
```

```
Val Gln Arg Asp Asp Ser Ser Asp Gly Ser Leu Glu Asp Asp Tyr
            100                 105                 110

His Ala Thr Thr Glu Thr Ile Ile Thr Met Pro Thr Glu Ser Asp Phe
            115                 120                 125

Leu Met Gln Ala Asp Gly Lys Pro Lys Cys Cys Phe Lys Phe Ser
130                 135                 140

Ser Lys Ile Gln Tyr Asn Lys Val Val Lys Ala Gln Leu Trp Ile Tyr
145                 150                 155                 160

Leu Arg Pro Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
                180                 185                 190

Leu Lys Leu Asp Met Ser Pro Gly Thr Gly Ile Trp Gln Ser Ile Asp
                195                 200                 205

Val Lys Thr Val Leu Gln Asn Trp Leu Lys Gln Pro Glu Ser Asn Leu
210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Asp Phe Gly Leu Asp
                260                 265                 270

Cys Asp Glu His Ser Thr Glu Ser Arg Cys Cys Arg Tyr Pro Leu Thr
                275                 280                 285

Val Asp Phe Glu Ala Phe Gly Trp Asp Trp Ile Ile Ala Pro Lys Arg
                290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
                340                 345                 350

Tyr Phe Asn Gly Lys Glu Gln Ile Ile Tyr Gly Lys Ile Pro Ala Met
                355                 360                 365

Val Val Asp Arg Cys Gly Cys Ser
                370                 375

<210> SEQ ID NO 6
<211> LENGTH: 109
<212> TYPE: PRT
<213> ORGANISM: Mus musculus

<400> SEQUENCE: 6

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
        50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
```

```
                        85                  90                  95
Lys Ile Pro Ala Met Val Val Asp Arg Cys Gly Cys Ser
                100                 105

<210> SEQ ID NO 7
<211> LENGTH: 328
<212> TYPE: PRT
<213> ORGANISM: Artificial sequence
<220> FEATURE:
<223> OTHER INFORMATION: An artificially synthesized sequence

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 8
<211> LENGTH: 987
<212> TYPE: DNA
<213> ORGANISM: Artificial sequence
<220> FEATURE:
<223> OTHER INFORMATION: An artificially synthesized sequence

<400> SEQUENCE: 8

```
gcttccacca agggcccatc ggtcttcccc ctggcaccct cctccaagtc cacctctggg      60
ggcacagcgg ccctgggctg cctggtcaag gactacttcc ccgaaccggt gacggtgtcg     120
tggaactcag gcgccctgac ctccggcgtg cacaccttcc cggctgtcct acagtcctca     180
ggactctact ccctctcctc cgtggtgacc gtgccctcca gtccttggg cacccagacc      240
tacatctgca acgtgaatca caagccctcc aacaccaagg tggacaagaa agttgagccc     300
aaatcttgtg acaaaactca cacatgccca ccgtgcccag cacctgaact cctggggggga   360
ccgtcagtct tcctcttccc cccaaaaccc aaggacaccc tcatgatctc ccggacccct     420
gaggtcacat gcgtggtggt ggacgtgtcc acgaagacc ctgaggtcaa gttcaactgg      480
tacgtggacg gcgtggaggt gcataatgcc aagacaaagc cgcgggagga gcagtacaac     540
tccacgtacc gtgtggtctc cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggaggaa      720
atgaccaaga accaggtctc cctgacctgc ctggtcaaag gcttctatcc ctccgacatc     780
gccgtggagt gggagtccaa tgggcagccg gagaacaact acaagaccac gcctcccgtg     840
ctggactccg acggctcctt cttcctctac tccaagctca ccgtggacaa gtccaggtgg     900
cagcagggga acgtcttctc atgctccgtg atgcatgagg ctctgcacaa ccactacacg     960
cagaagtcgc tctccctgtc tccgtag                                         987
```

<210> SEQ ID NO 9
<211> LENGTH: 107
<212> TYPE: PRT
<213> ORGANISM: Artificial sequence
<220> FEATURE:
<223> OTHER INFORMATION: An artificially synthesized sequence

<400> SEQUENCE: 9

```
Arg Thr Val Ala Ala Pro Ser Val Phe Ile Phe Pro Pro Ser Asp Glu
  1               5                  10                  15
Gln Leu Lys Ser Gly Thr Ala Ser Val Val Cys Leu Leu Asn Asn Phe
             20                  25                  30
Tyr Pro Arg Glu Ala Lys Val Gln Trp Lys Val Asp Asn Ala Leu Gln
         35                  40                  45
Ser Gly Asn Ser Gln Glu Ser Val Thr Glu Gln Asp Ser Lys Asp Cys
     50                  55                  60
Thr Tyr Ser Leu Ser Ser Thr Leu Thr Leu Ser Lys Ala Asp Tyr Glu
 65                  70                  75                  80
Lys His Lys Val Tyr Ala Cys Glu Val Thr His Gln Gly Leu Ser Ser
                 85                  90                  95
Pro Val Thr Lys Ser Phe Asn Arg Gly Glu Cys
            100                 105
```

<210> SEQ ID NO 10
<211> LENGTH: 324
<212> TYPE: DNA
<213> ORGANISM: Artificial sequence

```
<220> FEATURE:
<223> OTHER INFORMATION: An artificially synthesized sequence

<400> SEQUENCE: 10
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
tccaaggact gcacctactc cctctcctcc accctgacgc tgtccaaagc agactacgag     240
aaacacaaag tctacgcctg cgaagtcacc catcagggcc tgtcctcgcc cgtcacaaag     300
tccttcaaca ggggagagtg ttga                                            324

<210> SEQ ID NO 11
<211> LENGTH: 324
<212> TYPE: DNA
<213> ORGANISM: Artificial sequence
<220> FEATURE:
<223> OTHER INFORMATION: An artificially synthesized sequence

<400> SEQUENCE: 11
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agtaaggact gcacctacag tctcagtagt accctgacgc tgtccaaagc agactacgag     240
aaacacaaag tctacgcctg cgaagtcacc catcagggcc tgtcctcgcc cgtcacaaag     300
tccttcaaca ggggagagtg ttga                                            324

<210> SEQ ID NO 12
<211> LENGTH: 109
<212> TYPE: PRT
<213> ORGANISM: Artificial sequence
<220> FEATURE:
<223> OTHER INFORMATION: An artificially synthesized sequence

<400> SEQUENCE: 12

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Ser Trp Val Arg Gln Ala Pro Gly Lys Gly Leu Glu Trp Ile Gly
        35                  40                  45

Ile Ile Ser Ser Arg Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Val
                85                  90                  95

Val Leu Trp Gly Pro Gly Thr Leu Val Thr Val Ser Ser
            100                 105

<210> SEQ ID NO 13
<211> LENGTH: 119
<212> TYPE: PRT
<213> ORGANISM: Artificial sequence
<220> FEATURE:
<223> OTHER INFORMATION: An artificially synthesized sequence

<400> SEQUENCE: 13
```

Gln Ser Val Glu Glu Ser Gly Gly Arg Leu Val Thr Pro Gly Gly Ser
1               5                   10                  15

Leu Thr Leu Thr Cys Thr Val Ser Gly Phe Ser Leu Ser Asn Tyr Val
                20                  25                  30

Met Gly Trp Val Arg Gln Ala Pro Gly Lys Gly Leu Glu Trp Ile Gly
            35                  40                  45

Ile Ile Asn Ile Ser Gly Ser Thr Tyr Tyr Ala Ser Trp Ala Lys Gly
    50                  55                  60

Arg Phe Thr Ile Ser Arg Thr Ser Thr Val Asp Leu Lys Met Thr
65                  70                  75                  80

Ser Leu Thr Thr Glu Asp Thr Ala Thr Tyr Phe Cys Ala Arg Gly Gly
                85                  90                  95

Asp Asn Phe Gly Tyr Ser Tyr Ile Asp Phe Asn Leu Trp Gly Pro Gly
            100                 105                 110

Thr Leu Val Thr Val Ser Ser
            115

<210> SEQ ID NO 14
<211> LENGTH: 123
<212> TYPE: PRT
<213> ORGANISM: Artificial sequence
<220> FEATURE:
<223> OTHER INFORMATION: An artificially synthesized sequence

<400> SEQUENCE: 14

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Ser Ser Asn Val
                20                  25                  30

Met Gly Trp Val Arg Gln Ala Pro Gly Lys Gly Leu Glu Tyr Ile Gly
            35                  40                  45

Ile Ile Ile Tyr Gly Val Thr Thr Tyr Tyr Ala Thr Tyr Tyr Ala Ser
    50                  55                  60

Trp Ala Lys Gly Arg Phe Thr Ile Ser Lys Thr Ser Ser Thr Thr Val
65                  70                  75                  80

Asp Leu Lys Met Thr Ser Pro Thr Thr Glu Asp Thr Ala Thr Tyr Phe
                85                  90                  95

Cys Ala Arg Gly Ser Asp Ser Tyr Gly Tyr Ala Tyr Thr Phe Thr Leu
            100                 105                 110

Trp Gly Pro Gly Thr Leu Val Thr Val Ser Ser
            115                 120

<210> SEQ ID NO 15
<211> LENGTH: 118
<212> TYPE: PRT
<213> ORGANISM: Artificial sequence
<220> FEATURE:
<223> OTHER INFORMATION: An artificially synthesized sequence

<400> SEQUENCE: 15

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
                20                  25                  30

Met Ser Trp Val Arg Gln Ala Pro Gly Lys Gly Leu Glu Trp Ile Gly
            35                  40                  45

Tyr Ile Tyr Ala Gly Asn Gly Val Thr Tyr Tyr Ala Asn Trp Ala Lys

```
            50                  55                  60
Gly Arg Phe Thr Ile Ser Lys Thr Ser Thr Thr Val Asp Leu Lys
 65                  70                  75                  80

Met Thr Ser Leu Thr Ser Glu Asp Thr Ala Thr Tyr Phe Cys Gly Arg
                 85                  90                  95

Asp Leu Tyr Asn Ser Asp Trp Gly Leu Ala Leu Trp Gly Pro Gly Thr
            100                 105                 110

Leu Val Thr Val Ser Ser
        115

<210> SEQ ID NO 16
<211> LENGTH: 121
<212> TYPE: PRT
<213> ORGANISM: Artificial sequence
<220> FEATURE:
<223> OTHER INFORMATION: An artificially synthesized sequence

<400> SEQUENCE: 16

Gln Ser Leu Glu Glu Ser Gly Gly Arg Leu Val Thr Pro Gly Gly Ser
 1               5                  10                  15

Leu Thr Leu Thr Cys Thr Val Ser Gly Ile Asp Leu Ser Gly Tyr Ser
            20                  25                  30

Met Gly Trp Val Arg Gln Ala Pro Gly Lys Gly Leu Glu Tyr Ile Gly
        35                  40                  45

Ile Ile Ala Ser His Gly Asn Thr Tyr Tyr Ala Ser Trp Ala Lys Gly
    50                  55                  60

Arg Phe Thr Ile Ser Lys Thr Ser Thr Thr Val Asp Leu Lys Met
 65                  70                  75                  80

Thr Ser Leu Thr Thr Glu Asp Thr Ala Thr Tyr Phe Cys Gly Gly Asp
                 85                  90                  95

Val Ser Asp Ser Gly Asp Tyr Pro Tyr Tyr Gly Met Asp Pro Trp Gly
            100                 105                 110

Pro Gly Thr Leu Val Thr Val Ser Ser
        115                 120

<210> SEQ ID NO 17
<211> LENGTH: 122
<212> TYPE: PRT
<213> ORGANISM: Artificial sequence
<220> FEATURE:
<223> OTHER INFORMATION: An artificially synthesized sequence

<400> SEQUENCE: 17

Gln Ser Val Glu Glu Ser Gly Gly Arg Leu Val Thr Pro Gly Thr Pro
 1               5                  10                  15

Leu Thr Leu Thr Cys Thr Val Ser Arg Ile Asp Leu Ser Phe Tyr Ala
            20                  25                  30

Met Gly Trp Val Arg Arg Ala Pro Gly Lys Gly Leu Glu Tyr Ile Gly
        35                  40                  45

Ile Ile Ser Ser Gly Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Thr
 65                  70                  75                  80

Ser Pro Thr Thr Glu Asp Thr Ala Thr Tyr Phe Cys Ala Arg Gly Tyr
                 85                  90                  95

Asp Ser Gly Gly Asp Tyr Ala Arg Leu Tyr Tyr Gly Met Asp Leu Trp
            100                 105                 110
```

-continued

Gly Pro Gly Thr Leu Val Thr Val Ser Ser
        115                 120

<210> SEQ ID NO 18
<211> LENGTH: 121
<212> TYPE: PRT
<213> ORGANISM: Artificial sequence
<220> FEATURE:
<223> OTHER INFORMATION: An artificially synthesized sequence

<400> SEQUENCE: 18

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Tyr Met Tyr Trp Val Arg Gln Ala Pro Gly Lys Gly Leu Glu Trp Ile
        35                  40                  45

Ala Cys Ile His Ala Gly Ser Ser Gly Ser Thr Tyr Tyr Ala Ser Trp
    50                  55                  60

Ala Lys Gly Arg Phe Thr Ile Ser Lys Thr Ser Ser Thr Val Thr
65                  70                  75                  80

Leu Gln Met Thr Ser Leu Thr Ala Ala Asp Thr Ala Thr Tyr Phe Cys
            85                  90                  95

Ala Arg Gly Gly Ser Tyr Gly Tyr Pro Asp Tyr His Ser Leu Trp Gly
            100                 105                 110

Pro Gly Thr Leu Val Thr Val Ser Ser
        115                 120

<210> SEQ ID NO 19
<211> LENGTH: 117
<212> TYPE: PRT
<213> ORGANISM: Artificial sequence
<220> FEATURE:
<223> OTHER INFORMATION: An artificially synthesized sequence

<400> SEQUENCE: 19

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ser
            20                  25                  30

Met Thr Trp Val Arg Gln Ala Pro Gly Lys Gly Leu Glu Trp Ile Gly
        35                  40                  45

Val Ile Ser Tyr Gly Gly Val Thr Trp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Ala Tyr
            85                  90                  95

Gly Gly Val Ser Ile His Ser Phe Asn Leu Trp Gly Pro Gly Thr Leu
            100                 105                 110

Val Thr Val Ser Ser
115

<210> SEQ ID NO 20
<211> LENGTH: 119
<212> TYPE: PRT
<213> ORGANISM: Artificial sequence
<220> FEATURE:
<223> OTHER INFORMATION: An artificially synthesized sequence

```
<400> SEQUENCE: 20

Gln Ser Val Glu Glu Ser Gly Gly Arg Leu Val Thr Pro Thr Pro
1               5                   10                  15

Leu Thr Leu Thr Cys Thr Ala Ser Gly Phe Ser Phe Ser Ser Tyr Ala
                20                  25                  30

Met Ser Trp Val Arg Gln Ala Pro Gly Lys Gly Leu Glu Trp Ile Gly
            35                  40                  45

Ile Ile Tyr Gly Tyr Ser Gly Ser Thr Trp Tyr Ala Ser Trp Val Lys
50                  55                  60

Gly Arg Phe Thr Ile Ser Lys Thr Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Tyr Ala Ala Gly Thr Ile Ala Asp Gly Phe His Pro Trp Gly Pro Gly
                100                 105                 110

Thr Leu Val Thr Val Ser Ser
            115

<210> SEQ ID NO 21
<211> LENGTH: 107
<212> TYPE: PRT
<213> ORGANISM: Artificial sequence
<220> FEATURE:
<223> OTHER INFORMATION: An artificially synthesized sequence

<400> SEQUENCE: 21

Ala Leu Val Met Thr Gln Thr Pro Ala Ser Val Ser Ala Ala Val Gly
1               5                   10                  15

Gly Thr Val Thr Ile Asn Cys Gln Ala Ser Glu Ser Ile Tyr Ser Gly
                20                  25                  30

Leu Ala Trp Tyr Gln Gln Lys Pro Gly Gln Pro Pro Lys Leu Leu Ile
            35                  40                  45

Tyr Ser Ala Ser Thr Leu Ala Ser Gly Val Pro Ser Arg Phe Arg Gly
50                  55                  60

Ser Gly Ser Gly Thr Glu Tyr Thr Leu Thr Ile Asn Asp Leu Glu Cys
65                  70                  75                  80

Ala Asp Ala Ala Thr Tyr Tyr Cys Gln Ala Tyr Asp Ser Thr Asn Trp
                85                  90                  95

Thr Phe Gly Gly Gly Thr Glu Val Val Val Lys
                100                 105

<210> SEQ ID NO 22
<211> LENGTH: 110
<212> TYPE: PRT
<213> ORGANISM: Artificial sequence
<220> FEATURE:
<223> OTHER INFORMATION: An artificially synthesized sequence

<400> SEQUENCE: 22

Ala Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Ser Asn Glu
                20                  25                  30

Leu Ser Trp Tyr Arg Gln Lys Pro Gly Gln Pro Pro Lys Leu Leu Ile
            35                  40                  45

Tyr Leu Ala Ser Thr Leu Ala Ser Gly Val Pro Ser Arg Phe Lys Gly
50                  55                  60
```

-continued

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Thr Tyr Asp Gly Ile Ser Ser
                85                  90                  95

Tyr Gly Val Ala Phe Gly Gly Gly Thr Lys Val Val Val Glu
            100                 105                 110

<210> SEQ ID NO 23
<211> LENGTH: 111
<212> TYPE: PRT
<213> ORGANISM: Artificial sequence
<220> FEATURE:
<223> OTHER INFORMATION: An artificially synthesized sequence

<400> SEQUENCE: 23

Ala Val Val Leu Thr Gln Thr Ala Ser Pro Val Ser Ala Pro Val Gly
1               5                   10                  15

Gly Thr Val Thr Ile Lys Cys Gln Ala Ser Gln Ser Ile Ser Arg Tyr
                20                  25                  30

Leu Ala Trp Tyr Gln Gln Lys Pro Gly Gln Pro Pro Lys Leu Leu Ile
            35                  40                  45

Tyr Arg Ala Ser Thr Leu Ala Ser Gly Val Ser Ser Arg Phe Lys Gly
    50                  55                  60

Ser Arg Ser Gly Thr Glu Phe Thr Leu Thr Ile Ser Asp Leu Glu Cys
65                  70                  75                  80

Ala Asp Ala Ala Thr Tyr Tyr Cys Gln Asn Tyr Tyr Asp Gly Ser Thr
                85                  90                  95

Ser Gly Asp Ser Thr Phe Gly Gly Gly Thr Arg Val Val Val Glu
            100                 105                 110

<210> SEQ ID NO 24
<211> LENGTH: 110
<212> TYPE: PRT
<213> ORGANISM: Artificial sequence
<220> FEATURE:
<223> OTHER INFORMATION: An artificially synthesized sequence

<400> SEQUENCE: 24

Asp Val Val Met Thr Gln Thr Pro Ala Ser Val Ser Glu Pro Val Gly
1               5                   10                  15

Gly Thr Val Thr Ile Lys Cys Gln Ala Ser Gln Asn Ile Tyr Thr Asn
                20                  25                  30

Leu Ala Trp Tyr Gln Gln Lys Ser Gly Gln Arg Pro Lys Leu Leu Ile
            35                  40                  45

Tyr Ala Ala Ser Asn Leu Ala Ser Gly Val Pro Ser Arg Phe Ser Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Asn Asn Tyr Gly Ile Ser Ser
                85                  90                  95

Gly Gly Ala Thr Phe Gly Gly Gly Thr Thr Val Val Val Glu
            100                 105                 110

<210> SEQ ID NO 25
<211> LENGTH: 106
<212> TYPE: PRT
<213> ORGANISM: Artificial sequence
<220> FEATURE:
<223> OTHER INFORMATION: An artificially synthesized sequence

<400> SEQUENCE: 25

Glu Val Val Met Thr Gln Thr Pro Ser Ser Val Ser Glu Pro Val Gly
1               5                   10                  15

Gly Thr Val Thr Ile Lys Cys Gln Ala Ser Glu Asn Ile Tyr Ser Tyr
            20                  25                  30

Leu Ser Trp Tyr Gln Gln Lys Pro Gly Gln Pro Pro Lys Leu Leu Ile
        35                  40                  45

Tyr Gln Ala Ser Thr Leu Ala Ser Gly Val Ser Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser Asn Tyr His Gly Ser Ala
                85                  90                  95

Phe Gly Gly Gly Thr Thr Val Val Glu
            100                 105

<210> SEQ ID NO 26
<211> LENGTH: 111
<212> TYPE: PRT
<213> ORGANISM: Artificial sequence
<220> FEATURE:
<223> OTHER INFORMATION: An artificially synthesized sequence

<400> SEQUENCE: 26

Asp Val Val Met Thr Gln Thr Pro Ser Ser Lys Ser Ala Ala Val Gly
1               5                   10                  15

Asp Thr Val Thr Ile Lys Cys Gln Ala Ser Gln Ser Ile Tyr Ser Tyr
            20                  25                  30

Leu Ser Trp Tyr Gln Gln Lys Pro Gly Gln Pro Pro Lys Leu Leu Ile
        35                  40                  45

Tyr Gln Ala Ser Thr Leu Glu Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Asn Asn Tyr Asp Ser Ser Ser
                85                  90                  95

Asn Gly Phe Tyr Thr Phe Gly Gly Gly Thr Thr Val Val Glu
            100                 105                 110

<210> SEQ ID NO 27
<211> LENGTH: 106
<212> TYPE: PRT
<213> ORGANISM: Artificial sequence
<220> FEATURE:
<223> OTHER INFORMATION: An artificially synthesized sequence

<400> SEQUENCE: 27

Ala Phe Glu Leu Thr Gln Thr Pro Ser Ser Val Glu Ala Ala Val Gly
1               5                   10                  15

Gly Thr Val Thr Ile Lys Cys Gln Ala Ser Gln Ser Ile Tyr Ser Tyr
            20                  25                  30

Leu Ala Trp Tyr Gln Gln Thr Pro Gly Gln Pro Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Thr Tyr Asp Gly Ser Thr
                85                  90                  95

Phe Gly Gly Gly Thr Lys Val Val Val Glu
            100                 105

<210> SEQ ID NO 28
<211> LENGTH: 113
<212> TYPE: PRT
<213> ORGANISM: Artificial sequence
<220> FEATURE:
<223> OTHER INFORMATION: An artificially synthesized sequence

<400> SEQUENCE: 28

Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Leu Tyr Asn Asn
            20                  25                  30

Lys Asn Leu Ala Trp Tyr Gln Gln Lys Pro Gly Gln Pro Pro Lys Leu
        35                  40                  45

Leu Ile Tyr Tyr Ala Ser Thr Leu Ala Ser Gly Val Ser Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Glu Phe Ser Cys
                85                  90                  95

Ser Ser Ala Asp Cys Ile Ala Phe Gly Gly Gly Thr Thr Val Val Val
            100                 105                 110

Glu

<210> SEQ ID NO 29
<211> LENGTH: 110
<212> TYPE: PRT
<213> ORGANISM: Artificial sequence
<220> FEATURE:
<223> OTHER INFORMATION: An artificially synthesized sequence

<400> SEQUENCE: 29

Ala Leu Val Met Thr Gln Thr Pro Ala Ser Val Ser Ala Ala Val Gly
1               5                   10                  15

Gly Thr Val Thr Ile Asn Cys Gln Ala Ser Gln Ser Ile Gly Ser Ser
            20                  25                  30

Leu Ala Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80

Asp Asp Ala Ala Thr Tyr Tyr Cys Gln Gln Asp Tyr Thr Ser Ser Asn
                85                  90                  95

Val Asp Asn Thr Phe Gly Gly Gly Thr Lys Val Val Val Glu
            100                 105                 110

<210> SEQ ID NO 30
<211> LENGTH: 327
<212> TYPE: DNA
<213> ORGANISM: Artificial sequence
<220> FEATURE:
<223> OTHER INFORMATION: An artificially synthesized sequence

<400> SEQUENCE: 30

```
cagtcggtgg aggagtccgg gggtcgcctg gtcacgcctg ggacacccct gacactcacc    60
tgcacagcct ctggattctc cctcagtagc tactacatga gctgggtccg acaggctcca   120 gggaagggc tggaatggat cggaatcatt agtagtcgtg gtagcacata ctacgcgagc    180
tgggcgaaag gccgattcac catctccaaa acctcgacca cggtggatct gaaaatcacc   240
agtccgacaa ccgaggacac ggccacctat ttttgtgcca gaggtgttgt cttgtggggc   300
ccaggcaccc tggtcaccgt ctcctcc                                       327

<210> SEQ ID NO 31
<211> LENGTH: 357
<212> TYPE: DNA
<213> ORGANISM: Artificial sequence
<220> FEATURE:
<223> OTHER INFORMATION: An artificially synthesized sequence

<400> SEQUENCE: 31
cagtcggtgg aggagtccgg gggtcgcctg gtaacgcctg gaggatccct gacactcacc    60
tgcacagtct ctggattctc cctcagtaac tatgtaatgg gctgggtccg ccaggctcca   120 gggaagggc tggaatggat cggaatcatt aatattagtg gtagcacata ctacgcgagc    180
tgggcaaaag gccgattcac catctccaga acctcgacca cggtggatct gaaaatgacc   240
agtctgacaa ccgaggacac ggccacctat ttctgtgcca gagggggcga taattttggt   300
tatagttata ttgactttaa tttgtggggc ccaggcaccc tggtcaccgt ctcctcc      357

<210> SEQ ID NO 32
<211> LENGTH: 369
<212> TYPE: DNA
<213> ORGANISM: Artificial sequence
<220> FEATURE:
<223> OTHER INFORMATION: An artificially synthesized sequence

<400> SEQUENCE: 32
cagtcgctgg aggagtccgg gggtcgcctg gtaacgcctg gaggatccct gacactcacc    60
tgcacagtct ctggaatcga cctcagtagt aatgtaatgg gctgggtccg ccaggctcca   120 gggaagggc tggaatacat cggaatcatt atttatggtg ttaccacata ctacgccaca   180
tactacgcga gctgggcgaa aggccgattc accatctcca aaacctcgtc gaccacggtg   240
gatctgaaaa tgaccagtcc gacaaccgag gacacggcca cctatttctg tgccagaggg   300
agcgatagtt atggttatgc ttatactttt accttgtggg gcccaggcac cctggtcacc   360
gtctcctcc                                                           369

<210> SEQ ID NO 33
<211> LENGTH: 354
<212> TYPE: DNA
<213> ORGANISM: Artificial sequence
<220> FEATURE:
<223> OTHER INFORMATION: An artificially synthesized sequence

<400> SEQUENCE: 33
cagtcgctgg aggagtccgg gggtcgcctg gtcacgcctg ggacacccct gacactcacc    60
tgcacagtct ctggaatcga cctcagtagt tatgcaatga gttgggtccg ccaggctcca   120 gggaagggc tggagtggat cggatacatt tatgctggta atggtgtcac atactacgcg    180
aactgggcga aaggccgatt caccatctcc aaaacctcgt cgaccacggt ggatctgaaa    240
atgaccagtc tgacaagtga ggacacggcc acctatttct gtggcagaga tctttataat   300
```

```
agtgattggg gattggcctt gtggggccca ggcaccctgg tcaccgtctc ctcc         354

<210> SEQ ID NO 34
<211> LENGTH: 363
<212> TYPE: DNA
<213> ORGANISM: Artificial sequence
<220> FEATURE:
<223> OTHER INFORMATION: An artificially synthesized sequence

<400> SEQUENCE: 34
cagtcgctgg aggagtccgg gggtcgcctg gtaacgcctg gaggatccct gacactcacc    60
tgcacagtct ctggaatcga cctcagtggc tattcaatgg gctgggtccg ccaggctcca   120
gggaaggggc tggaatacat cggaatcatt gctagtcatg gtaacacata ctacgcgagc   180
tgggcgaaag gccgattcac catctccaaa acctcgtcga ccacggtgga tctgaaaatg   240
accagtctga caaccgagga cacggccacc tatttctgtg gtggcgatgt tagtgatagt   300
ggtgattatc cctactacgg catggacccc tggggcccag ggaccctcgt caccgtctcc   360
tcc                                                                363

<210> SEQ ID NO 35
<211> LENGTH: 366
<212> TYPE: DNA
<213> ORGANISM: Artificial sequence
<220> FEATURE:
<223> OTHER INFORMATION: An artificially synthesized sequence

<400> SEQUENCE: 35
cagtcggtgg aggagtccgg gggtcgcctg gtcacgcctg ggacacccct gacactcacc    60
tgcacagtct ctagaatcga cctcagtttc tatgcaatgg gctgggtccg ccgggctcca   120
gggaaggggc tggaatacat cggaatcatt agtagtggtg gtagcacata ctacgcgagc   180
tgggcgaaag gccgattcac catctccaaa acctcgacca cggtggatct gaaaatcacc   240
agtccgacaa ccgaggacac ggccacctat ttctgtgcca gaggttacga tagtggtggt   300
gattatgctc gactttacta cggcatggac ctctggggcc cagggaccct cgtcaccgtc   360
tcctcc                                                             366

<210> SEQ ID NO 36
<211> LENGTH: 363
<212> TYPE: DNA
<213> ORGANISM: Artificial sequence
<220> FEATURE:
<223> OTHER INFORMATION: An artificially synthesized sequence

<400> SEQUENCE: 36
cagtcgttgg aggagtccgg gggagacctg gtcaagcctg gggcatccct gacactcacc    60
tgcacagcct ctggattctc cttcagtagc agctactaca tgtactgggt ccgccaggct   120
ccagggaagg ggctggagtg gatcgcatgc attcatgctg gtagtagtgg tagcacttac   180
tacgcgagct gggcgaaagg ccgattcacc atctccaaaa cctcgtcgac cacggtgact   240
ctgcaaatga ccagtctgac agccgcggac acggccacct atttctgtgc gagagggggt   300
agttatggtt atcctgatta tcatagctta tggggcccag gcaccctggt caccgtctcc   360
tcc                                                                363

<210> SEQ ID NO 37
<211> LENGTH: 351
<212> TYPE: DNA
<213> ORGANISM: Artificial sequence
```

```
<220> FEATURE:
<223> OTHER INFORMATION: An artificially synthesized sequence

<400> SEQUENCE: 37
cagtcggtgg aggagtccgg gggtcgcctg gtcacgcctg ggacacccct gacactcacc      60
tgcacagtct ctggattctc cctcagtagc tattcaatga cctgggtccg ccaggctcca     120
gggaaggggc tggaatggat cggagtcatt agttatggtg gtgttacatg gtacgcgagc     180
tgggcgaaag gccgattcac catctccaaa acctcgacca cggtggatct gaaaatcacc     240
agtccgacaa ccgaggacac ggccacttat ttctgtgcca gagcgtatgg tggtgttagt     300
attcatagct ttaatttgtg gggcccaggc accctggtca ccgtctcctc c              351

<210> SEQ ID NO 38
<211> LENGTH: 357
<212> TYPE: DNA
<213> ORGANISM: Artificial sequence
<220> FEATURE:
<223> OTHER INFORMATION: An artificially synthesized sequence

<400> SEQUENCE: 38
cagtcggtgg aggagtccgg gggtcgcctg gtcacgcctg ggacacccct gacactcacc      60
tgcacagcct ctggattctc cttcagtagc tatgcaatga gctgggtccg ccaggctcca     120
gggaaggggc tggaatggat cggaatcatt tatggttata gtggtagtac atggtacgcg     180
agctgggtga aggccgatt caccatctcc aaaacctcga ccacggtgga tctgaaaatg      240
accagtctga caaccgagga cacggccacc tatttctgtg ccagaggata tgctgctggt     300
actattgcag atggttttca tccctggggc ccaggcaccc tggtcaccgt ctcctcc        357

<210> SEQ ID NO 39
<211> LENGTH: 321
<212> TYPE: DNA
<213> ORGANISM: Artificial sequence
<220> FEATURE:
<223> OTHER INFORMATION: An artificially synthesized sequence

<400> SEQUENCE: 39
gcccttgtga tgacccagac tccagcctcc gtgtctgcag ctgtgggagg cacagtcacc      60
atcaattgcc aggccagtga gagcatttat agtggtttgg cctggtatca gcagaaacca     120
gggcagcctc ccaagctcct gatctattct gcatccactc tggcatctgg ggtcccatcg     180
cggttcagag gcagtggatc tgggacagag tacactctca ccatcaacga cctggagtgt     240
gccgatgctg ccacttacta ctgtcaagcc tatgatagta ctaattggac tttcggcgga     300
gggaccgagg tggtggtcaa a                                                321

<210> SEQ ID NO 40
<211> LENGTH: 330
<212> TYPE: DNA
<213> ORGANISM: Artificial sequence
<220> FEATURE:
<223> OTHER INFORMATION: An artificially synthesized sequence

<400> SEQUENCE: 40
gctgttgtga tgacccagac tccagcctcc gtgtctgaac tgtgggagg cacagtcacc       60 atcaagtgcc aggccagtca gagcattagc aatgaattat cctggtatcg ccagaaacca     120
gggcagcctc ccaagctcct gatctatctt gcatctacgc tggcatctgg ggtcccatcg     180
cggttcaaag gcagtggatc tgggacagac ttcactctca ccatcagcga cctggagtgt     240
```

```
gccgatgctg ccacttacta ctgtcaaacc tatgatggta ttagtagtta tggtgttgct   300
ttcggcggag ggaccaaggt ggtcgtcgaa                                    330

<210> SEQ ID NO 41
<211> LENGTH: 333
<212> TYPE: DNA
<213> ORGANISM: Artificial sequence
<220> FEATURE:
<223> OTHER INFORMATION: An artificially synthesized sequence

<400> SEQUENCE: 41
gccgtcgtgc tgacccagac tgcatccccc gtgtctgcac ctgtgggagg cacagtcacc    60
atcaagtgcc aggccagtca gagcattagt agatacttag cctggtatca gcagaaacca   120
gggcagcctc ccaagctcct gatctacagg gcatccactc tggcgtctgg ggtctcatcg   180
cggttcaaag gcagtagatc tgggacagag ttcactctca ccatcagcga cctggagtgt   240
gccgatgctg ccacttacta ctgtcaaaat tattatgatg gtagtactag tggtgatagt   300
actttcggcg agggaccagg gtggtcgtc gag                                 333

<210> SEQ ID NO 42
<211> LENGTH: 330
<212> TYPE: DNA
<213> ORGANISM: Artificial sequence
<220> FEATURE:
<223> OTHER INFORMATION: An artificially synthesized sequence

<400> SEQUENCE: 42
gatgttgtga tgacccagac tccagcctcc gtgtctgaac ctgtgggagg cacagtcacc    60
atcaagtgcc aggccagtca gaatatttac accaatttag cctggtatca gcagaaatca   120
gggcagcgtc ccaagctcct gatctatgct gcatccaatc tggcatctgg ggtcccatcg   180
cggttcagtg gcagtggatc tgggacagag tacactctca ccatcagcga cctggagtgt   240
gccgatgctg ccacttacta ctgtcaaaac aattatggta ttagtagtgg tggtgctact   300
ttcggcggag ggaccacggt ggtcgtcgaa                                    330

<210> SEQ ID NO 43
<211> LENGTH: 316
<212> TYPE: DNA
<213> ORGANISM: Artificial sequence
<220> FEATURE:
<223> OTHER INFORMATION: An artificially synthesized sequence

<400> SEQUENCE: 43
gaagtagtga tgacccagac tccatcctcc gtgtctgaac ctgtgggagg cacagtcacc    60
atcaagtgcc aggccagtga gaacatttac agctacttat cctggtatca gcagaaacca   120
gggcagcctc ccaagctcct gatctaccag gcatccactc tggcatctgg ggtctcatcg   180
cggttcaaag gcagtggatc tgggacacag ttcactctca ccatcagcga cctggagtgt   240
gccgatgctg ccacttacta ctgtcaaagc aattatcatg gtagtgcttt cggcggaggg   300
accacggtgg tcgtcg                                                   316

<210> SEQ ID NO 44
<211> LENGTH: 333
<212> TYPE: DNA
<213> ORGANISM: Artificial sequence
<220> FEATURE:
<223> OTHER INFORMATION: An artificially synthesized sequence

<400> SEQUENCE: 44
```

```
gatgttgtga tgacccagac tccatcctcc aagtctgcag ctgtgggaga cacagtcacc      60
atcaagtgcc aggccagtca gagcatttac agctacttat cctggtatca gcagaaacca     120
gggcagcctc ccaagctcct aatctaccag gcatccactc tggaatctgg ggtcccatcg     180
cggttcaaag gcagtggatc tgggacacag ttcactctca ccatcagcga cctggagtgt     240
gccgatgctg ccacttacta ctgtcaaaat aattatgata gtagtagtaa tggttttat      300 actttcggcg gagggaccac ggtggtcgtc gaa                                  333
```

<210> SEQ ID NO 45
<211> LENGTH: 318
<212> TYPE: DNA
<213> ORGANISM: Artificial sequence
<220> FEATURE:
<223> OTHER INFORMATION: An artificially synthesized sequence

<400> SEQUENCE: 45

```
gcattcgaat tgacccagac tccatcctcc gtggaggcag ctgtgggagg cacagtcacc      60
atcaagtgcc aggccagtca gagcatttac agctacttgg cctggtatca gcagacacca     120
gggcagcctc ccaagctcct gatctatgaa gcatccaaac tggcctctgg ggtcccatcg     180
cggttcagcg gcagtggatc tgggacagag ttcactctca ccatcagcga cctggagtgt     240
gccgatgctg ccacttacta ctgtcaaacc tattatgatg gtagcacttt cggcggaggg     300
accaaggtgg tcgtcgaa                                                   318
```

<210> SEQ ID NO 46
<211> LENGTH: 339
<212> TYPE: DNA
<213> ORGANISM: Artificial sequence
<220> FEATURE:
<223> OTHER INFORMATION: An artificially synthesized sequence

<400> SEQUENCE: 46

```
gcccaagtgc tgacccagac tccatcctcc gtgtctgcag ctgtgggagg cacagtcacc      60
atcaactgcc aggccagtca gagtctttat aataacaaaa atttagcctg gtatcagcag     120
aaaccagggc agcctcccaa gctcctgatc tattatgcat ccactctggc atctggggtc     180
tcatcgcggt tcaaaggcag tggatctggg acacagttca ctctcaccat cagcggcgtg     240
cagtgtgacg atgctgccac ttactactgt caaggcaatt tagttgtag tagtgctgat      300 tgtattgctt tcggcggagg gaccacggtg gtcgtcgaa                            339
```

<210> SEQ ID NO 47
<211> LENGTH: 330
<212> TYPE: DNA
<213> ORGANISM: Artificial sequence
<220> FEATURE:
<223> OTHER INFORMATION: An artificially synthesized sequence

<400> SEQUENCE: 47

```
gcccttgtga tgacccagac tccagcctcc gtgtctgcag ctgtgggagg cacagtcacc      60
atcaattgcc aggccagtca gagcattggt agtagcttag cctggtatca acagaaacca     120
gggcagcgtc ccaagctcct gatctacagg gcatccactc tggcatctgg ggtctcatcg     180
cggttcaaag gcagtggatc tgggacacag ttcactctca ccatcagcgg cgtggagtgt     240
gacgatgctg ccacttacta ctgtcaacag gattatacta gtagtaatgt tgataatact     300
ttcggcggag ggaccaaggt ggtcgtcgaa                                      330
```

<210> SEQ ID NO 48
<211> LENGTH: 122
<212> TYPE: PRT
<213> ORGANISM: Artificial sequence
<220> FEATURE:
<223> OTHER INFORMATION: An artificially synthesized sequence

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Leu Ser Asn Tyr
            20                  25                  30

Val Met Gly Trp Val Arg Gln Ala Pro Gly Lys Gly Leu Glu Trp Ile
        35                  40                  45

Gly Ile Ile Asn Ile Ser Gly Ser Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Gly Gly Asp Asn Phe Gly Tyr Ser Tyr Ile Asp Phe Asn Leu Trp
            100                 105                 110

Gly Gln Gly Thr Leu Val Thr Val Ser Ser
        115                 120

<210> SEQ ID NO 49
<211> LENGTH: 122
<212> TYPE: PRT
<213> ORGANISM: Artificial sequence
<220> FEATURE:
<223> OTHER INFORMATION: An artificially synthesized sequence

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Leu Ser His Tyr
            20                  25                  30

Val Lys Gly Trp Val Arg Gln Ala Pro Gly Lys Gly Leu Glu Trp Ile
        35                  40                  45

Gly Ile Ile Asn Ile Ser Gly Ser Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Gly His Asp Asn Phe Gly Tyr Ser Tyr His Asp Phe Asn Leu Trp
            100                 105                 110

Gly Gln Gly Thr Leu Val Thr Val Ser Ser
        115                 120

<210> SEQ ID NO 50
<211> LENGTH: 122
<212> TYPE: PRT
<213> ORGANISM: Artificial sequence
<220> FEATURE:
<223> OTHER INFORMATION: An artificially synthesized sequence

<400> SEQUENCE: 50

Glu Val Gln Leu Val Glu Ser Gly Gly Gly Leu Val Gln Pro Gly Gly

```
                1               5                   10                  15
Ser Leu Arg Leu Ser Cys Ala Val Ser Gly Phe Thr Leu Ser His Tyr
                20                  25                  30

Val Lys Gly Trp Val Arg Gln Ala Pro Gly Lys Gly Leu Glu Trp Ile
            35                  40                  45

Gly Ile Ile Asn Ile Glu Gly Ser Thr Tyr Tyr Ala Ser Trp Ala Glu
        50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Gly His Asp Asn Phe Gly Tyr Ser Tyr His Asp Phe Asn Leu Trp
                100                 105                 110

Gly Gln Gly Thr Leu Val Thr Val Ser Ser
                115                 120

<210> SEQ ID NO 51
<211> LENGTH: 122
<212> TYPE: PRT
<213> ORGANISM: Artificial sequence
<220> FEATURE:
<223> OTHER INFORMATION: An artificially synthesized sequence

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Leu Ser His Tyr
                20                  25                  30

Val Lys Gly Trp Val Arg Gln Ala Pro Gly Lys Gly Leu Glu Trp Ile
            35                  40                  45

Gly Ile Ile Asn Ile Glu Gly Glu Thr Tyr Tyr Ala Ser Trp Ala Lys
        50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Gly His Asp Asn Phe Gly Tyr Ser Tyr His Asp Phe Asn Leu Trp
                100                 105                 110

Gly Gln Gly Thr Leu Val Thr Val Ser Ser
                115                 120

<210> SEQ ID NO 52
<211> LENGTH: 110
<212> TYPE: PRT
<213> ORGANISM: Artificial sequence
<220> FEATURE:
<223> OTHER INFORMATION: An artificially synthesized sequence

<400> SEQUENCE: 52

Ala Val Val Met Thr Gln Ser Pro Ala Thr Leu Ser Leu Ser Pro Gly
1               5                   10                  15

Glu Arg Val Thr Leu Ser Cys Gln Ala Ser Gln Ser Ile Ser Asn Glu
                20                  25                  30

Leu Ser Trp Tyr Gln Gln Lys Pro Gly Gln Pro Pro Lys Leu Leu Ile
            35                  40                  45

Tyr Leu Ala Ser Thr Leu Ala Ser Gly Val Pro Ser Arg Phe Lys Gly
        50                  55                  60
```

```
Ser Gly Ser Gly Thr Asp Phe Thr Leu Thr Ile Ser Ser Leu Gln Pro
 65                  70                  75                  80

Glu Asp Ala Ala Thr Tyr Tyr Cys Gln Thr Tyr Asp Gly Ile Ser Ser
                 85                  90                  95

Tyr Gly Val Ala Phe Gly Gln Gly Thr Lys Val Glu Ile Lys
            100                 105                 110
```

<210> SEQ ID NO 53
<211> LENGTH: 110
<212> TYPE: PRT
<213> ORGANISM: Artificial sequence
<220> FEATURE:
<223> OTHER INFORMATION: An artificially synthesized sequence

<400> SEQUENCE: 53

```
Ala Val Val Met Thr Gln Ser Pro Ala Thr Leu Ser Leu Ser Pro Gly
 1                5                  10                  15

Glu Arg Val Thr Leu Ser Cys Gln Ala Ser Gln Ser Ile His His Glu
                 20                  25                  30

Leu Ser Trp Tyr Gln Gln Lys Pro Gly Gln Pro Pro Lys Leu Leu Ile
             35                  40                  45

Tyr Leu Ala Ser Thr Leu Ala Ser Gly Val Pro Ser Arg Phe Lys Gly
 50                  55                  60

Ser Gly Ser Gly Thr Asp Phe Thr Leu Thr Ile Ser Ser Leu Gln Pro
 65                  70                  75                  80

Glu Asp Ala Ala Thr Tyr Tyr Cys Gln Thr Tyr Asp Gly Ile Ser His
                 85                  90                  95

Tyr Gly Val Ala Phe Gly Gln Gly Thr Lys Val Glu Ile Lys
            100                 105                 110
```

<210> SEQ ID NO 54
<211> LENGTH: 110
<212> TYPE: PRT
<213> ORGANISM: Artificial sequence
<220> FEATURE:
<223> OTHER INFORMATION: An artificially synthesized sequence

<400> SEQUENCE: 54

```
Ala Val Val Met Thr Gln Ser Pro Ala Thr Leu Ser Leu Ser Pro Gly
 1                5                  10                  15

Glu Arg Val Thr Leu Ser Cys Gln Ala Ser Glu Ser Ile His His Glu
                 20                  25                  30

Leu Ser Trp Tyr Gln Gln Lys Pro Gly Gln Pro Pro Lys Leu Leu Ile
             35                  40                  45

Tyr Leu Ala Ser Thr Leu Ala Ser Gly Val Pro Ser Arg Phe Lys Gly
 50                  55                  60

Ser Gly Ser Gly Thr Asp Phe Thr Leu Thr Ile Ser Ser Leu Gln Pro
 65                  70                  75                  80

Glu Asp Ala Ala Thr Tyr Tyr Cys Gln Thr Tyr Asp Gly Ile Ser His
                 85                  90                  95

Tyr Gly Val Ala Phe Gly Gln Gly Thr Lys Val Glu Ile Lys
            100                 105                 110
```

<210> SEQ ID NO 55
<211> LENGTH: 110
<212> TYPE: PRT
<213> ORGANISM: Artificial sequence
<220> FEATURE:
<223> OTHER INFORMATION: An artificially synthesized sequence

<400> SEQUENCE: 55

Ala Val Val Met Thr Gln Ser Pro Ala Thr Leu Ser Leu Ser Pro Gly
1               5                   10                  15

Glu Arg Val Thr Leu Ser Cys Gln Ala Ser Gln Ser Ile His His Asp
            20                  25                  30

Leu Ser Trp Tyr Gln Gln Lys Pro Gly Gln Pro Pro Lys Leu Leu Ile
        35                  40                  45

Tyr Leu Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Thr Tyr Asp Gly Ile Ser His
                85                  90                  95

Tyr Gly Val Ala Phe Gly Gln Gly Thr Lys Val Glu Ile Lys
            100                 105                 110

<210> SEQ ID NO 56
<211> LENGTH: 366
<212> TYPE: DNA
<213> ORGANISM: Artificial sequence
<220> FEATURE:
<223> OTHER INFORMATION: An artificially synthesized sequence

<400> SEQUENCE: 56
gaagtgcagc tggtcgagag cggggggggg ctggtgcagc caggaggatc actgcgactg      60
agctgcgctg tctccgggtt cacactgtcc aactacgtga tgggatgggt cagacaggca     120
cctgggaagg gactggagtg gatcggaatc attaatatct ctggcagtac ttactatgcc     180
tcttgggcta agggccggtt cactatctct agagacaaca gtaaaaatac cgtgtacctg     240
cagatgaact cactgagggc agaagatacc gccgtgtatt tttgtgcccg cggaggcgac     300
aacttcgggt acagctatat tgattttaat ctgtggggcc aggggaccct ggtgacagtc     360
agctcc                                                               366

<210> SEQ ID NO 57
<211> LENGTH: 366
<212> TYPE: DNA
<213> ORGANISM: Artificial sequence
<220> FEATURE:
<223> OTHER INFORMATION: An artificially synthesized sequence

<400> SEQUENCE: 57
gaagtgcagc tggtcgagag cggggggggg ctggtgcagc caggaggatc actgcgactg      60
agctgcgctg tctccgggtt cacactgtcc cactacgtga agggatgggt cagacaggca     120
cctgggaagg gactggagtg gatcggaatc attaatatct ctggcagtac ttactatgcc     180
tcttgggcta agggccggtt cactatctct agagacaaca gtaaaaatac cgtgtacctg     240
cagatgaact cactgagggc agaagatacc gccgtgtatt tttgtgcccg cggacacgac     300
aacttcgggt acagctatca tgattttaat ctgtggggcc aggggaccct ggtgacagtc     360
agctcc                                                               366

<210> SEQ ID NO 58
<211> LENGTH: 366
<212> TYPE: DNA
<213> ORGANISM: Artificial sequence
<220> FEATURE:
<223> OTHER INFORMATION: An artificially synthesized sequence

<400> SEQUENCE: 58

| gaagtgcagc tggtcgagag cggggggggg ctggtgcagc caggaggatc actgcgactg | 60 |
| agctgcgctg tctccgggtt cacactgtcc cactacgtga agggatgggt cagacaggca | 120 |
| cctgggaagg gactggagtg gatcggaatc attaatatcg agggcagtac ttactatgcc | 180 |
| tcttgggctg agggccggtt cactatctct agagacaaca gtaaaaatac cgtgtacctg | 240 |
| cagatgaact cactgagggc agaagatacc gccgtgtatt tttgtgcccg cggacacgac | 300 |
| aacttcgggt acagctatca tgattttaat ctgtggggcc aggggaccct ggtgacagtc | 360 |
| agctcc | 366 |

<210> SEQ ID NO 59
<211> LENGTH: 366
<212> TYPE: DNA
<213> ORGANISM: Artificial sequence
<220> FEATURE:
<223> OTHER INFORMATION: An artificially synthesized sequence

<400> SEQUENCE: 59

| gaagtgcagc tggtcgagag cggggggggg ctggtgcagc caggaggatc actgcgactg | 60 |
| agctgcgctg tctccgggtt cacactgtcc cactacgtga agggatgggt cagacaggca | 120 |
| cctgggaagg gactggagtg gatcggaatc attaatatcg agggcgagac ttactatgcc | 180 |
| tcttgggcta agggccggtt cactatctct agagacaaca gtaaaaatac cgtgtacctg | 240 |
| cagatgaact cactgagggc agaagatacc gccgtgtatt tttgtgcccg cggacacgac | 300 |
| aacttcgggt acagctatca tgattttaat ctgtggggcc aggggaccct ggtgacagtc | 360 |
| agctcc | 366 |

<210> SEQ ID NO 60
<211> LENGTH: 330
<212> TYPE: DNA
<213> ORGANISM: Artificial sequence
<220> FEATURE:
<223> OTHER INFORMATION: An artificially synthesized sequence

<400> SEQUENCE: 60

| gccgtcgtga tgactcagag ccctgctaca ctgtcactga gccctggaga gcgagttact | 60 |
| ctgagctgcc aggcatccca gtctatcagt aacgaactgt cctggtatca gcagaagcca | 120 |
| gggcagcccc ctaaactgct gatctacctg gcatctaccc tggccagtgg cgtgccctct | 180 |
| agattcaaag gcagcgggtc cggaacagac tttaccctga caatcagctc cctgcagcca | 240 |
| gaggacgcag ctacttacta ttgtcagacc tacgatggaa tctctagtta tggagtggca | 300 |
| ttcggacagg ggaccaaggt cgagatcaag | 330 |

<210> SEQ ID NO 61
<211> LENGTH: 330
<212> TYPE: DNA
<213> ORGANISM: Artificial sequence
<220> FEATURE:
<223> OTHER INFORMATION: An artificially synthesized sequence

<400> SEQUENCE: 61

| gccgtcgtga tgactcagag ccctgctaca ctgtcactga gccctggaga gcgagttact | 60 |
| ctgagctgcc aggcatccca gtctatccat cacgaactgt cctggtatca gcagaagcca | 120 |
| gggcagcccc ctaaactgct gatctacctg gcatctaccc tggccagtgg cgtgccctct | 180 |
| agattcaaag gcagcgggtc cggaacagac tttaccctga caatcagctc cctgcagcca | 240 |

```
gaggacgcag ctacttacta ttgtcagacc tacgatggaa tctctcatta tggagtggca    300
ttcggacagg ggaccaaggt cgagatcaag                                     330

<210> SEQ ID NO 62
<211> LENGTH: 330
<212> TYPE: DNA
<213> ORGANISM: Artificial sequence
<220> FEATURE:
<223> OTHER INFORMATION: An artificially synthesized sequence

<400> SEQUENCE: 62
gccgtcgtga tgactcagag ccctgctaca ctgtcactga gccctggaga gcgagttact     60
ctgagctgcc aggcatccga gtctatccat cacgaactgt cctggtatca gcagaagcca    120
gggcagcccc ctaaactgct gatctacctg gcatctaccc tggccagtgg cgtgccctct    180
agattcaaag gcagcgggtc cggaacagac tttaccctga caatcagctc cctgcagcca    240
gaggacgcag ctacttacta ttgtcagacc tacgatggaa tctctcatta tggagtggca    300
ttcggacagg ggaccaaggt cgagatcaag                                     330

<210> SEQ ID NO 63
<211> LENGTH: 330
<212> TYPE: DNA
<213> ORGANISM: Artificial sequence
<220> FEATURE:
<223> OTHER INFORMATION: An artificially synthesized sequence

<400> SEQUENCE: 63
gccgtcgtga tgactcagag ccctgctaca ctgtcactga gccctggaga gcgagttact     60
ctgagctgcc aggcatccca gtctatccat cacgacctgt cctggtatca gcagaagcca    120
gggcagcccc ctaaactgct gatctacctg gcatctaccc tggccagtgg cgtgccctct    180
agattcaaag gcagcgggtc cggaacagac tttaccctga caatcagctc cctgcagcca    240
gaggacgcag ctacttacta ttgtcagacc tacgatggaa tctctcatta tggagtggca    300
ttcggacagg ggaccaaggt cgagatcaag                                     330

<210> SEQ ID NO 64
<211> LENGTH: 328
<212> TYPE: PRT
<213> ORGANISM: Artificial sequence
<220> FEATURE:
<223> OTHER INFORMATION: An artificially synthesized sequence

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 65
<211> LENGTH: 107
<212> TYPE: PRT
<213> ORGANISM: Artificial sequence
<220> FEATURE:
<223> OTHER INFORMATION: An artificially synthesized sequence

<400> SEQUENCE: 65

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 66
<211> LENGTH: 987
<212> TYPE: DNA
<213> ORGANISM: Artificial sequence
```

<220> FEATURE:
<223> OTHER INFORMATION: An artificially synthesized sequence

<400> SEQUENCE: 66

```
gcttccacca agggcccatc ggtcttcccc ctggcaccct cctccaagtc gacctctggg      60
ggcacagcgg ccctgggctg cctggtcaag gactacttcc ccgaaccggt gacggtgtcg     120
tggaactcag gcgccctgac cagtggcgtg cacaccttcc cggctgtcct acagtcctca     180
ggactctact ccctcagtag tgtggtgacc gtgccctcca gtagtttggg cacccagacc     240
tacatctgca acgtgaatca caagcccagt aacaccaagg tggacaagaa agttgagccc     300
aaatcttgtg acaaaactca cacatgccca ccgtgcccag cacctgagct cctgggggga     360
ccgtcagtct tcctcttccc cccaaaaccc aaggacaccc tcatgatctc ccggacccct     420
gaggtcacat gcgtggtggt ggacgtgagt cacgaagacc ctgaggtcaa gttcaactgg     480
tacgtggacg gcgtggaggt gcataatgcc aagacaaagc cgcgggagga gcagtacaac     540
agtacgtacc gtgtggtcag tgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccggaggag     720
atgaccaaga accaggtcag tctgacctgc ctggtcaaag gcttctatcc cagtgacatc     780
gccgtggagt gggagagtaa tgggcagccg gagaacaact acaagaccac gcctcccgtg     840
ctggactccg acggctcctt cttcctctac agtaagctca ccgtggacaa gagtaggtgg     900
cagcagggga acgtcttctc atgctccgtg atgcatgagg ctctgcacaa ccactacacg     960
cagaagagtc tctccctgtc tccgtga                                          987
```

<210> SEQ ID NO 67
<211> LENGTH: 324
<212> TYPE: DNA
<213> ORGANISM: Artificial sequence
<220> FEATURE:
<223> OTHER INFORMATION: An artificially synthesized sequence

<400> SEQUENCE: 67

```
cgtacggtgg ctgcaccatc tgtcttcatc ttcccgccat ctgatgagca gttgaaatct      60
ggtaccgcct ctgttgtgtg cctgctgaat aacttctatc ccagagaggc caaagtacag     120
tggaaggtgg ataacgccct ccaatcgggt aactcccagg agagtgtcac agagcaggac     180
agtaaggaca gtacctacag tctcagtagt accctgacgc tgtccaaagc agactacgag     240
aaacacaaag tctacgcctg cgaagtcacc catcagggcc tgtcctcgcc cgtcacaaag     300
tccttcaaca ggggagagtg ttga                                             324
```

<210> SEQ ID NO 68
<211> LENGTH: 328
<212> TYPE: PRT
<213> ORGANISM: Artificial sequence
<220> FEATURE:
<223> OTHER INFORMATION: An artificially synthesized sequence

<400> SEQUENCE: 68

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Arg Gly Gly Pro Lys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 69
<211> LENGTH: 984
<212> TYPE: DNA
<213> ORGANISM: Artificial sequence
<220> FEATURE:
<223> OTHER INFORMATION: An artificially synthesized sequence

<400> SEQUENCE: 69
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact ccggggggga     360
ccgaaagtct tcctcttccc cccaaaaccc aaggacaccc tcatgatctc ccggacccct     420

```
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccg                                           984
```

<210> SEQ ID NO 70
<211> LENGTH: 5
<212> TYPE: PRT
<213> ORGANISM: Artificial sequence
<220> FEATURE:
<223> OTHER INFORMATION: An artificially synthesized sequence

<400> SEQUENCE: 70

Asn Tyr Val Met Gly
1               5

<210> SEQ ID NO 71
<211> LENGTH: 5
<212> TYPE: PRT
<213> ORGANISM: Artificial sequence
<220> FEATURE:
<223> OTHER INFORMATION: An artificially synthesized sequence

<400> SEQUENCE: 71

His Tyr Val Lys Gly
1               5

<210> SEQ ID NO 72
<211> LENGTH: 16
<212> TYPE: PRT
<213> ORGANISM: Artificial sequence
<220> FEATURE:
<223> OTHER INFORMATION: An artificially synthesized sequence

<400> SEQUENCE: 72

Ile Ile Asn Ile Ser Gly Ser Thr Tyr Tyr Ala Ser Trp Ala Lys Gly
1               5                   10                  15

<210> SEQ ID NO 73
<211> LENGTH: 16
<212> TYPE: PRT
<213> ORGANISM: Artificial sequence
<220> FEATURE:
<223> OTHER INFORMATION: An artificially synthesized sequence

<400> SEQUENCE: 73

Ile Ile Asn Ile Glu Gly Ser Thr Tyr Tyr Ala Ser Trp Ala Glu Gly
1               5                   10                  15

<210> SEQ ID NO 74
<211> LENGTH: 16
<212> TYPE: PRT
<213> ORGANISM: Artificial sequence
<220> FEATURE:
<223> OTHER INFORMATION: An artificially synthesized sequence

```
<400> SEQUENCE: 74

Ile Ile Asn Ile Glu Gly Glu Thr Tyr Tyr Ala Ser Trp Ala Lys Gly
1               5                   10                  15

<210> SEQ ID NO 75
<211> LENGTH: 14
<212> TYPE: PRT
<213> ORGANISM: Artificial sequence
<220> FEATURE:
<223> OTHER INFORMATION: An artificially synthesized sequence

<400> SEQUENCE: 75

Gly Gly Asp Asn Phe Gly Tyr Ser Tyr Ile Asp Phe Asn Leu
1               5                   10

<210> SEQ ID NO 76
<211> LENGTH: 14
<212> TYPE: PRT
<213> ORGANISM: Artificial sequence
<220> FEATURE:
<223> OTHER INFORMATION: An artificially synthesized sequence

<400> SEQUENCE: 76

Gly His Asp Asn Phe Gly Tyr Ser Tyr His Asp Phe Asn Leu
1               5                   10

<210> SEQ ID NO 77
<211> LENGTH: 11
<212> TYPE: PRT
<213> ORGANISM: Artificial sequence
<220> FEATURE:
<223> OTHER INFORMATION: An artificially synthesized sequence

<400> SEQUENCE: 77

Gln Ala Ser Gln Ser Ile Ser Asn Glu Leu Ser
1               5                   10

<210> SEQ ID NO 78
<211> LENGTH: 11
<212> TYPE: PRT
<213> ORGANISM: Artificial sequence
<220> FEATURE:
<223> OTHER INFORMATION: An artificially synthesized sequence

<400> SEQUENCE: 78

Gln Ala Ser Gln Ser Ile His His Glu Leu Ser
1               5                   10

<210> SEQ ID NO 79
<211> LENGTH: 11
<212> TYPE: PRT
<213> ORGANISM: Artificial sequence
<220> FEATURE:
<223> OTHER INFORMATION: An artificially synthesized sequence

<400> SEQUENCE: 79

Gln Ala Ser Glu Ser Ile His His Glu Leu Ser
1               5                   10

<210> SEQ ID NO 80
<211> LENGTH: 11
<212> TYPE: PRT
<213> ORGANISM: Artificial sequence
<220> FEATURE:
<223> OTHER INFORMATION: An artificially synthesized sequence
```

```
<400> SEQUENCE: 80

Gln Ala Ser Gln Ser Ile His His Asp Leu Ser
1               5                   10

<210> SEQ ID NO 81
<211> LENGTH: 7
<212> TYPE: PRT
<213> ORGANISM: Artificial sequence
<220> FEATURE:
<223> OTHER INFORMATION: An artificially synthesized sequence

<400> SEQUENCE: 81

Leu Ala Ser Thr Leu Ala Ser
1               5

<210> SEQ ID NO 82
<211> LENGTH: 12
<212> TYPE: PRT
<213> ORGANISM: Artificial sequence
<220> FEATURE:
<223> OTHER INFORMATION: An artificially synthesized sequence

<400> SEQUENCE: 82

Gln Thr Tyr Asp Gly Ile Ser Ser Tyr Gly Val Ala
1               5                   10

<210> SEQ ID NO 83
<211> LENGTH: 12
<212> TYPE: PRT
<213> ORGANISM: Artificial sequence
<220> FEATURE:
<223> OTHER INFORMATION: An artificially synthesized sequence

<400> SEQUENCE: 83

Gln Thr Tyr Asp Gly Ile Ser His Tyr Gly Val Ala
1               5                   10

<210> SEQ ID NO 84
<211> LENGTH: 5
<212> TYPE: PRT
<213> ORGANISM: Artificial sequence
<220> FEATURE:
<223> OTHER INFORMATION: An artificially synthesized sequence
<220> FEATURE:
<221> NAME/KEY: misc_feature
<222> LOCATION: (1)..(1)
<223> OTHER INFORMATION: Xaa is N or H
<220> FEATURE:
<221> NAME/KEY: misc_feature
<222> LOCATION: (4)..(4)
<223> OTHER INFORMATION: Xaa is M or K

<400> SEQUENCE: 84

Xaa Tyr Val Xaa Gly
1               5

<210> SEQ ID NO 85
<211> LENGTH: 16
<212> TYPE: PRT
<213> ORGANISM: Artificial sequence
<220> FEATURE:
<223> OTHER INFORMATION: An artificially synthesized sequence
<220> FEATURE:
<221> NAME/KEY: misc_feature
<222> LOCATION: (5)..(5)
<223> OTHER INFORMATION: Xaa is S or E
<220> FEATURE:
<221> NAME/KEY: misc_feature
<222> LOCATION: (7)..(7)
```

```
<223> OTHER INFORMATION: Xaa is S or E
<220> FEATURE:
<221> NAME/KEY: misc_feature
<222> LOCATION: (15)..(15)
<223> OTHER INFORMATION: Xaa is K or E

<400> SEQUENCE: 85

Ile Ile Asn Ile Xaa Gly Xaa Thr Tyr Tyr Ala Ser Trp Ala Xaa Gly
1               5                   10                  15

<210> SEQ ID NO 86
<211> LENGTH: 14
<212> TYPE: PRT
<213> ORGANISM: Artificial sequence
<220> FEATURE:
<223> OTHER INFORMATION: An artificially synthesized sequence
<220> FEATURE:
<221> NAME/KEY: misc_feature
<222> LOCATION: (2)..(2)
<223> OTHER INFORMATION: Xaa is G or H
<220> FEATURE:
<221> NAME/KEY: misc_feature
<222> LOCATION: (10)..(10)
<223> OTHER INFORMATION: Xaa is I or H

<400> SEQUENCE: 86

Gly Xaa Asp Asn Phe Gly Tyr Ser Tyr Xaa Asp Phe Asn Leu
1               5                   10

<210> SEQ ID NO 87
<211> LENGTH: 11
<212> TYPE: PRT
<213> ORGANISM: Artificial sequence
<220> FEATURE:
<223> OTHER INFORMATION: An artificially synthesized sequence
<220> FEATURE:
<221> NAME/KEY: misc_feature
<222> LOCATION: (4)..(4)
<223> OTHER INFORMATION: Xaa is Q or E
<220> FEATURE:
<221> NAME/KEY: misc_feature
<222> LOCATION: (7)..(7)
<223> OTHER INFORMATION: Xaa is S or H
<220> FEATURE:
<221> NAME/KEY: misc_feature
<222> LOCATION: (8)..(8)
<223> OTHER INFORMATION: Xaa is N or H
<220> FEATURE:
<221> NAME/KEY: misc_feature
<222> LOCATION: (9)..(9)
<223> OTHER INFORMATION: Xaa is E or D

<400> SEQUENCE: 87

Gln Ala Ser Xaa Ser Ile Xaa Xaa Xaa Leu Ser
1               5                   10

<210> SEQ ID NO 88
<211> LENGTH: 12
<212> TYPE: PRT
<213> ORGANISM: Artificial sequence
<220> FEATURE:
<223> OTHER INFORMATION: An artificially synthesized sequence
<220> FEATURE:
<221> NAME/KEY: misc_feature
<222> LOCATION: (8)..(8)
<223> OTHER INFORMATION: Xaa is S or H

<400> SEQUENCE: 88

Gln Thr Tyr Asp Gly Ile Ser Xaa Tyr Gly Val Ala
1               5                   10
```

```
<210> SEQ ID NO 89
<211> LENGTH: 30
<212> TYPE: PRT
<213> ORGANISM: Artificial sequence
<220> FEATURE:
<223> OTHER INFORMATION: An artificially synthesized sequence

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Leu Ser
            20                  25                  30

<210> SEQ ID NO 90
<211> LENGTH: 14
<212> TYPE: PRT
<213> ORGANISM: Artificial sequence
<220> FEATURE:
<223> OTHER INFORMATION: An artificially synthesized sequence

<400> SEQUENCE: 90

Trp Val Arg Gln Ala Pro Gly Lys Gly Leu Glu Trp Ile Gly
1               5                   10

<210> SEQ ID NO 91
<211> LENGTH: 32
<212> TYPE: PRT
<213> ORGANISM: Artificial sequence
<220> FEATURE:
<223> OTHER INFORMATION: An artificially synthesized sequence

<400> SEQUENCE: 91

Arg Phe Thr Ile Ser Arg Asp Asn Ser Lys Asn Thr Val Tyr Leu Gln
1               5                   10                  15

Met Asn Ser Leu Arg Ala Glu Asp Thr Ala Val Tyr Phe Cys Ala Arg
            20                  25                  30

<210> SEQ ID NO 92
<211> LENGTH: 11
<212> TYPE: PRT
<213> ORGANISM: Artificial sequence
<220> FEATURE:
<223> OTHER INFORMATION: An artificially synthesized sequence

<400> SEQUENCE: 92

Trp Gly Gln Gly Thr Leu Val Thr Val Ser Ser
1               5                   10

<210> SEQ ID NO 93
<211> LENGTH: 23
<212> TYPE: PRT
<213> ORGANISM: Artificial sequence
<220> FEATURE:
<223> OTHER INFORMATION: An artificially synthesized sequence

<400> SEQUENCE: 93

Ala Val Val Met Thr Gln Ser Pro Ala Thr Leu Ser Leu Ser Pro Gly
1               5                   10                  15

Glu Arg Val Thr Leu Ser Cys
            20

<210> SEQ ID NO 94
<211> LENGTH: 15
<212> TYPE: PRT
<213> ORGANISM: Artificial sequence
<220> FEATURE:
```

-continued

<223> OTHER INFORMATION: An artificially synthesized sequence

<400> SEQUENCE: 94

Trp Tyr Gln Gln Lys Pro Gly Gln Pro Pro Lys Leu Leu Ile Tyr
1               5                   10                  15

<210> SEQ ID NO 95
<211> LENGTH: 32
<212> TYPE: PRT
<213> ORGANISM: Artificial sequence
<220> FEATURE:
<223> OTHER INFORMATION: An artificially synthesized sequence

<400> SEQUENCE: 95

Gly Val Pro Ser Arg Phe Lys Gly Ser Gly Ser Gly Thr Asp Phe Thr
1               5                   10                  15

Leu Thr Ile Ser Ser Leu Gln Pro Glu Asp Ala Ala Thr Tyr Tyr Cys
            20                  25                  30

<210> SEQ ID NO 96
<211> LENGTH: 10
<212> TYPE: PRT
<213> ORGANISM: Artificial sequence
<220> FEATURE:
<223> OTHER INFORMATION: An artificially synthesized sequence

<400> SEQUENCE: 96

Phe Gly Gln Gly Thr Lys Val Glu Ile Lys
1               5                   10

<210> SEQ ID NO 97
<211> LENGTH: 242
<212> TYPE: PRT
<213> ORGANISM: Homo sapiens

<400> SEQUENCE: 97

Glu Asn Ser Glu Gln Lys Glu Asn Val Glu Lys Glu Gly Leu Cys Asn
1               5                   10                  15

Ala Cys Thr Trp Arg Gln Asn Thr Lys Ser Ser Arg Ile Glu Ala Ile
            20                  25                  30

Lys Ile Gln Ile Leu Ser Lys Leu Arg Leu Glu Thr Ala Pro Asn Ile
        35                  40                  45

Ser Lys Asp Val Ile Arg Gln Leu Leu Pro Lys Ala Pro Pro Leu Arg
    50                  55                  60

Glu Leu Ile Asp Gln Tyr Asp Val Gln Arg Asp Asp Ser Ser Asp Gly
65                  70                  75                  80

Ser Leu Glu Asp Asp Asp Tyr His Ala Thr Thr Glu Thr Ile Ile Thr
                85                  90                  95

Met Pro Thr Glu Ser Asp Phe Leu Met Gln Val Asp Gly Lys Pro Lys
            100                 105                 110

Cys Cys Phe Phe Lys Phe Ser Ser Lys Ile Gln Tyr Asn Lys Val Val
        115                 120                 125

Lys Ala Gln Leu Trp Ile Tyr Leu Arg Pro Val Glu Thr Pro Thr Thr
    130                 135                 140

Val Phe Val Gln Ile Leu Arg Leu Ile Lys Pro Met Lys Asp Gly Thr
145                 150                 155                 160

Arg Tyr Thr Gly Ile Arg Ser Leu Lys Leu Asp Met Asn Pro Gly Thr
                165                 170                 175

Gly Ile Trp Gln Ser Ile Asp Val Lys Thr Val Leu Gln Asn Trp Leu
            180                 185                 190

Lys Gln Pro Glu Ser Asn Leu Gly Ile Glu Ile Lys Ala Leu Asp Glu
            195                 200                 205

Asn Gly His Asp Leu Ala Val Thr Phe Pro Gly Pro Gly Glu Asp Gly
        210                 215                 220

Leu Asn Pro Phe Leu Glu Val Lys Val Thr Asp Thr Pro Lys Arg Ser
225                 230                 235                 240

Arg Arg

<210> SEQ ID NO 98
<211> LENGTH: 242
<212> TYPE: PRT
<213> ORGANISM: Macaca fascicularis

<400> SEQUENCE: 98

Glu Asn Ser Glu Gln Lys Glu Asn Val Glu Lys Glu Gly Leu Cys Asn
1               5                   10                  15

Ala Cys Thr Trp Arg Gln Asn Thr Lys Ser Ser Arg Ile Glu Ala Ile
            20                  25                  30

Lys Ile Gln Ile Leu Ser Lys Leu Arg Leu Glu Thr Ala Pro Asn Ile
        35                  40                  45

Ser Lys Asp Ala Ile Arg Gln Leu Leu Pro Lys Ala Pro Pro Leu Arg
    50                  55                  60

Glu Leu Ile Asp Gln Tyr Asp Val Gln Arg Asp Asp Ser Ser Asp Gly
65                  70                  75                  80

Ser Leu Glu Asp Asp Asp Tyr His Ala Thr Thr Glu Thr Ile Ile Thr
                85                  90                  95

Met Pro Thr Glu Ser Asp Phe Leu Met Gln Val Asp Gly Lys Pro Lys
            100                 105                 110

Cys Cys Phe Phe Lys Phe Ser Ser Lys Ile Gln Tyr Asn Lys Val Val
        115                 120                 125

Lys Ala Gln Leu Trp Ile Tyr Leu Arg Pro Val Glu Thr Pro Thr Thr
    130                 135                 140

Val Phe Val Gln Ile Leu Arg Leu Ile Lys Pro Met Lys Asp Gly Thr
145                 150                 155                 160

Arg Tyr Thr Gly Ile Arg Ser Leu Lys Leu Asp Met Asn Pro Gly Thr
                165                 170                 175

Gly Ile Trp Gln Ser Ile Asp Val Lys Thr Val Leu Gln Asn Trp Leu
            180                 185                 190

Lys Gln Pro Glu Ser Asn Leu Gly Ile Glu Ile Lys Ala Leu Asp Glu
        195                 200                 205

Asn Gly His Asp Leu Ala Val Thr Phe Pro Gly Pro Gly Glu Asp Gly
    210                 215                 220

Leu Asn Pro Phe Leu Glu Val Lys Val Thr Asp Thr Pro Lys Arg Ser
225                 230                 235                 240

Arg Arg

<210> SEQ ID NO 99
<211> LENGTH: 242
<212> TYPE: PRT
<213> ORGANISM: Mus musculus

<400> SEQUENCE: 99

Glu Gly Ser Glu Arg Glu Glu Asn Val Glu Lys Glu Gly Leu Cys Asn
1               5                   10                  15

Ala Cys Ala Trp Arg Gln Asn Thr Arg Tyr Ser Arg Ile Glu Ala Ile

```
                    20                  25                  30
Lys Ile Gln Ile Leu Ser Lys Leu Arg Leu Glu Thr Ala Pro Asn Ile
                35                  40                  45

Ser Lys Asp Ala Ile Arg Gln Leu Leu Pro Arg Ala Pro Pro Leu Arg
            50                  55                  60

Glu Leu Ile Asp Gln Tyr Asp Val Gln Arg Asp Ser Ser Asp Gly
65                  70                  75                  80

Ser Leu Glu Asp Asp Tyr His Ala Thr Thr Glu Thr Ile Ile Thr
                    85                  90                  95

Met Pro Thr Glu Ser Asp Phe Leu Met Gln Ala Asp Gly Lys Pro Lys
                100                 105                 110

Cys Cys Phe Phe Lys Phe Ser Ser Lys Ile Gln Tyr Asn Lys Val Val
                115                 120                 125

Lys Ala Gln Leu Trp Ile Tyr Leu Arg Pro Val Lys Thr Pro Thr Thr
                130                 135                 140

Val Phe Val Gln Ile Leu Arg Leu Ile Lys Pro Met Lys Asp Gly Thr
145                 150                 155                 160

Arg Tyr Thr Gly Ile Arg Ser Leu Lys Leu Asp Met Ser Pro Gly Thr
                165                 170                 175

Gly Ile Trp Gln Ser Ile Asp Val Lys Thr Val Leu Gln Asn Trp Leu
                180                 185                 190

Lys Gln Pro Glu Ser Asn Leu Gly Ile Glu Ile Lys Ala Leu Asp Glu
                195                 200                 205

Asn Gly His Asp Leu Ala Val Thr Phe Pro Gly Pro Gly Glu Asp Gly
                210                 215                 220

Leu Asn Pro Phe Leu Glu Val Lys Val Thr Asp Thr Pro Lys Arg Ser
225                 230                 235                 240

Arg Arg

<210> SEQ ID NO 100
<211> LENGTH: 266
<212> TYPE: PRT
<213> ORGANISM: Homo sapiens

<400> SEQUENCE: 100

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
                20                  25                  30

Val Glu Lys Glu Gly Leu Cys Asn Ala Cys Thr Trp Arg Gln Asn Thr
            35                  40                  45

Lys Ser Ser Arg Ile Glu Ala Ile Lys Ile Gln Ile Leu Ser Lys Leu
        50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
                100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
        130                 135                 140

Lys Ile Gln Tyr Asn Lys Val Val Lys Ala Gln Leu Trp Ile Tyr Leu
```

```
            145                 150                 155                 160
Arg Pro Val Glu Thr Pro Thr Thr Val Phe Val Gln Ile Leu Arg Leu
                    165                 170                 175

Ile Lys Pro Met Lys Asp Gly Thr Arg Tyr Thr Gly Ile Arg Ser Leu
                    180                 185                 190

Lys Leu Asp Met Asn Pro Gly Thr Gly Ile Trp Gln Ser Ile Asp Val
                    195                 200                 205

Lys Thr Val Leu Gln Asn Trp Leu Lys Gln Pro Glu Ser Asn Leu Gly
                    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                    245                 250                 255

Val Thr Asp Thr Pro Lys Arg Ser Arg Arg
                    260                 265

<210> SEQ ID NO 101
<211> LENGTH: 266
<212> TYPE: PRT
<213> ORGANISM: Macaca fascicularis

<400> SEQUENCE: 101

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
                    20                  25                  30

Val Glu Lys Glu Gly Leu Cys Asn Ala Cys Thr Trp Arg Gln Asn Thr
                35                  40                  45

Lys Ser Ser Arg Ile Glu Ala Ile Lys Ile Gln Ile Leu Ser Lys Leu
            50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Arg Glu Leu Ile Asp Gln Tyr Asp Val
                    85                  90                  95

Gln Arg Asp Asp Ser Ser Asp Gly Ser Leu Glu Asp Asp Asp Tyr His
                    100                 105                 110

Ala Thr Thr Glu Thr Ile Ile Thr Met Pro Thr Glu Ser Asp Phe Leu
                115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                    165                 170                 175

Ile Lys Pro Met Lys Asp Gly Thr Arg Tyr Thr Gly Ile Arg Ser Leu
                    180                 185                 190

Lys Leu Asp Met Asn Pro Gly Thr Gly Ile Trp Gln Ser Ile Asp Val
                    195                 200                 205

Lys Thr Val Leu Gln Asn Trp Leu Lys Gln Pro Glu Ser Asn Leu Gly
                    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                    245                 250                 255
```

```
Val Thr Asp Thr Pro Lys Arg Ser Arg Arg
            260                 265

<210> SEQ ID NO 102
<211> LENGTH: 267
<212> TYPE: PRT
<213> ORGANISM: Mus musculus

<400> SEQUENCE: 102

Met Met Gln Lys Leu Gln Met Tyr Val Tyr Ile Tyr Leu Phe Met Leu
1               5                   10                  15

Ile Ala Ala Gly Pro Val Asp Leu Asn Glu Gly Ser Glu Arg Glu Glu
                20                  25                  30

Asn Val Glu Lys Glu Gly Leu Cys Asn Ala Cys Ala Trp Arg Gln Asn
                35                  40                  45

Thr Arg Tyr Ser Arg Ile Glu Ala Ile Lys Ile Gln Ile Leu Ser Lys
50                      55                  60

Leu Arg Leu Glu Thr Ala Pro Asn Ile Ser Lys Asp Ala Ile Arg Gln
65                  70                  75                  80

Leu Leu Pro Arg Ala Pro Pro Leu Arg Glu Leu Ile Asp Gln Tyr Asp
                85                  90                  95

Val Gln Arg Asp Asp Ser Ser Asp Gly Ser Leu Glu Asp Asp Asp Tyr
                100                 105                 110

His Ala Thr Thr Glu Thr Ile Ile Thr Met Pro Thr Glu Ser Asp Phe
            115                 120                 125

Leu Met Gln Ala Asp Gly Lys Pro Lys Cys Cys Phe Phe Lys Phe Ser
            130                 135                 140

Ser Lys Ile Gln Tyr Asn Lys Val Val Lys Ala Gln Leu Trp Ile Tyr
145                 150                 155                 160

Leu Arg Pro Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
                180                 185                 190

Leu Lys Leu Asp Met Ser Pro Gly Thr Gly Ile Trp Gln Ser Ile Asp
            195                 200                 205

Val Lys Thr Val Leu Gln Asn Trp Leu Lys Gln Pro Glu Ser Asn Leu
            210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg
                260                 265
```

ANTI-MYOSTATIN ANTIBODIES AND METHODS OF USE

CROSS-REFERENCE TO RELATED APPLICATIONS

This application is a divisional of U.S. patent application Ser. No. 16/065,192, § 371 filing date of Jun. 22, 2018, which is a U.S. National Phase of PCT Application No. PCT/JP2016/088302, filed Dec. 22, 2016, which claims the benefit of Japanese Patent Application No. 2015-253346, filed Dec. 25, 2015, each of which is incorporated herein by reference in its entirety.

REFERENCE TO SEQUENCE LISTING SUBMITTED ELECTRONICALLY

The content of the electronically submitted sequence listing (Name: 6663_0205_sequence_listing.txt; Size: 93.6 kilobytes; and Date of Creation: May 12, 2022) filed with the application is incorporated herein by reference in its entirety.

TECHNICAL FIELD

The present invention relates to anti-myostatin antibodies and methods of using the same.

BACKGROUND ART

Myostatin, also referred to as growth differentiation factor-8 (GDF-8), is a secreted protein and is a member of the transforming growth factor-beta (TGF-beta) superfamily of proteins. Members of this superfamily possess growth-regulatory and morphogenetic properties (See, e.g., NPL 1, NPL 2, and PTL 1). Myostatin is expressed primarily in the developing and adult skeletal muscle and functions as a negative regulator of muscle growth. Systemic overexpression of myostatin in adult mice leads to muscle wasting (See, e.g., NPL 3) while, conversely, a myostatin knockout mouse is characterized by hypertrophy and hyperplasia of the skeletal muscle resulting in two- to threefold greater muscle mass than their wild type littermates (See, e.g., NPL 4).

Like other members of the TGF-beta family, myostatin is synthesized as a large precursor protein containing an N-terminal propeptide domain, and a C-terminal domain considered as the active molecule (See, e.g., NPL 5; PTL 2). Two molecules of myostatin precursor are covalently linked via a single disulfide bond present in the C-terminal growth factor domain. Active mature myostatin (disulfide-bonded homodimer consisting of the C-terminal growth factor domain) is liberated from myostatin precursor through multiple steps of proteolytic processing. In the first step of the myostatin activation pathway, a peptide bond between the N-terminal propeptide domain and the C-terminal growth factor domain, Arg266-Asp267, is cleaved by a furin-type proprotein convertase in both chains of the homodimeric precursor. But the resulting two propeptides and one mature myostatin (disulfide-bonded homodimer consisting of the growth factor domains) remain associated, forming a non-covalent inactive complex, that is latent myostatin. Mature myostatin can then be liberated from latent myostatin through degradation of the propeptide. Members of the bone morphogenetic protein 1 (BMP-1) family of metalloproteinases cleave a single peptide bond within the propeptide, Arg98-Asp99, with concomitant release of the mature myostatin (See, e.g., NPL 6). Moreover, the latent myostatin can be activated in vitro by dissociating the complex with either acid or heat treatment as well (See, e.g., NPL 7).

Myostatin exerts its effects through a transmembrane serine/threonine kinase heterotetramer receptor family, activation of which enhances receptor transphosphorylation, leading to the stimulation of serine/threonine kinase activity. It has been shown that the myostatin pathway involves an active myostatin dimer binding to the activin receptor type IIB (ActRIIB) with high affinity, which then recruits and activates the transphosphorylation of the low affinity receptor, the activin-like kinase 4 (ALK4) or activin-like kinase 5 (ALK5). It has also been shown that the proteins Smad 2 and Smad 3 are subsequently activated and form complexes with Smad 4, which are then translocated to the nucleus for the activation of target gene transcription. It has been demonstrated that ActRIIB is able to mediate the influence of myostatin in vivo, as expression of a dominant negative form of ActRIIB in mice mimics myostatin gene knockout (See, e.g., NPL 8).

A number of disorders or conditions are associated with muscle wasting (i.e., loss of or functional impairment of muscle tissue), such as muscular dystrophy (MD; including Duchenne muscular dystrophy), amyotrophic lateral sclerosis (ALS), muscle atrophy, organ atrophy, frailty, congestive obstructive pulmonary disease (COPD), sarcopenia, and cachexia resulting from cancer or other disorders, as well as renal disease, cardiac failure or disease, and liver disease. Patients will benefit from an increase in muscle mass and/or muscle strength; however, there are presently limited treatments available for these disorders. Thus, due to its role as a negative regulator of skeletal muscle growth, myostatin becomes a desirable target for therapeutic or prophylactic intervention for such disorders or conditions, or for monitoring the progression of such disorders or conditions. In particular, agents that inhibit the activity of myostatin may be therapeutically beneficial.

Inhibition of myostatin expression leads to both muscle hypertrophy and hyperplasia (NPL 4). Myostatin negatively regulates muscle regeneration after injury and lack of myostatin in myostatin null mice results in accelerated muscle regeneration (See, e.g., NPL 9). Anti-myostatin (GDF-8) antibodies described in, e.g., PTL 3, PTL 4, PTL 5, PTL 6, PTL 7, PTL 8, PTL 9, PTL 10, and PTL 11 have been shown to bind to myostatin and inhibit myostatin activity in vitro and in vivo, including myostatin activity associated with the negative regulation of skeletal muscle mass. Myostatin-neutralizing antibodies increase body weight, skeletal muscle mass, and muscle size and strength in the skeletal muscle of wild type mice (See, e.g., NPL 10) and the mdx mice, a model for muscular dystrophy (See, e.g., NPL 11; NPL 12). However, there is a further need for improvements in efficacy and convenience of agents that bind myostatin and antagonize its activity in the art.

CITATION LIST

Patent Literature

[PTL 1] U.S. Pat. No. 5,827,733
[PTL 2] WO 94/021681
[PTL 3] U.S. Pat. No. 6,096,506
[PTL 4] WO 2004/037861
[PTL 5] U.S. Pat. No. 7,320,789
[PTL 6] U.S. Pat. No. 7,807,159
[PTL 7] U.S. Pat. No. 7,888,486
[PTL 8] WO 2005/094446
[PTL 9] U.S. Pat. No. 7,632,499
[PTL 10] WO 2010/070094
[PTL 11] U.S. Pat. No. 8,415,459

Non Patent Literature

[NPL 1] Kingsley et al (1994) Genes Dev 8(2): 133-146
[NPL 2] Hoodless et al (1998) Curr Top Microbiol Immunol 228: 235-272
[NPL 3] Zimmers et al (2002) Science 296(5572): 1486-1488
[NPL 4] McPherron et al (1997) Nature 387(6628): 83-90
[NPL 5] McPherron and Lee (1997) Proc Natl Acad Sci USA 94(23): 12457-12461
[NPL 6] Szlama et al (2013) FEBS J 280(16): 3822-3839
[NPL 7] Lee (2008) PloS One 3(2): e1628
[NPL 8] Lee and McPherron (2001) Proc Natl Acad Sci USA 98(16): 9306-9311
[NPL 9] McCroskery et al (2005) J Cell Sci 118(15): 3531-3541
[NPL 10] Whittemore et al (2003) Biochem Biophys Res Commun 300(4): 965-971
[NPL 11] Bogdanovich et al (2002) Nature 420(6914): 418-421
[NPL 12] Wagner et al (2002) Ann Neurol 52(6): 832-836

SUMMARY OF INVENTION

Technical Problem

An objective of the invention is to provide anti-myostatin antibodies and methods of using the same.

Solution to Problem

The invention provides anti-myostatin antibodies and methods of using the same.

In some embodiments, an isolated anti-myostatin antibody of the present invention binds to mature myostatin. In some embodiments, uptake of an isolated anti-myostatin antibody of the present invention into cells is enhanced when complexed with an antigen. In further embodiments, the uptake is caused by the interaction between Fc region of the antibody and Fc gamma R on the cells. In further embodiments, the antibody shows at least 2.5-fold higher uptake compared with a reference antibody which is identical to the antibody except that Fc region of the reference antibody has no Fc gamma R-binding activity. In some embodiments, an isolated anti-myostatin antibody of the present invention has an inhibitory activity against myostatin. In some embodiments, an isolated anti-myostatin antibody of the present invention binds to the same epitope as an antibody described in Table 2 or 3. In some embodiments, an isolated anti-myostatin antibody of the present invention competes for binding to myostatin with an antibody described in Table 2 or 3. In some embodiments, an isolated anti-myostatin antibody of the present invention binds to mature myostatin with higher affinity at neutral pH than at acidic pH.

In some embodiments, an isolated anti-myostatin antibody of the present invention is a monoclonal antibody. In some embodiments, an isolated anti-myostatin antibody of the present invention is a human, humanized, or chimeric antibody. In some embodiments, an isolated anti-myostatin antibody of the present invention is an antibody fragment that binds to myostatin. In some embodiments, an isolated anti-myostatin antibody of the present invention is a full length IgG antibody.

In some embodiments, an isolated anti-myostatin antibody of the present invention comprises (a) HVR-H3 comprising the amino acid sequence $GX_1DNFGYSYX_2DFNL$, wherein $X_1$ is G or H, $X_2$ is I or H (SEQ ID NO: 86), (b) HVR-L3 comprising the amino acid sequence $QTYDGISX_1YGVA$, wherein $X_1$ is S or H (SEQ ID NO: 88), and (c) HVR-H2 comprising the amino acid sequence $IINIX_1GX_2TYYASWAX_3G$, wherein $X_1$ is S or E, $X_2$ is S or E, $X_3$ is K or E (SEQ ID NO: 85).

In some embodiments, an isolated anti-myostatin antibody of the present invention comprises (a) HVR-H1 comprising the amino acid sequence $X_1YVX_2G$, wherein $X_1$ is N or H, $X_2$ is M or K (SEQ ID NO: 84), (b) HVR-H2 comprising the amino acid sequence $IINIX_1GX_2TYYASWAX_3G$, wherein $X_1$ is S or E, $X_2$ is S or E, $X_3$ is K or E (SEQ ID NO: 85), and (c) HVR-H3 comprising the amino acid sequence $GX_1DNFGYSYX_2DFNL$, wherein $X_1$ is G or H, $X_2$ is I or H (SEQ ID NO: 86). In further embodiments, the antibody comprises (a) HVR-L1 comprising the amino acid sequence $QASX_1SIX_2X_3X_4LS$, wherein $X_1$ is Q or E, $X_2$ is S or H, $X_3$ is N or H, $X_4$ is E or D (SEQ ID NO: 87); (b) HVR-L2 comprising the amino acid sequence LASTLAS (SEQ ID NO: 81); and (c) HVR-L3 comprising the amino acid sequence $QTYDGISX_1YGVA$, wherein $X_1$ is S or H (SEQ ID NO: 88).

In some embodiments, an isolated anti-myostatin antibody of the present invention comprises (a) HVR-L1 comprising the amino acid sequence $QASX_1SIX_2X_3X_4LS$, wherein $X_1$ is Q or E, $X_2$ is S or H, $X_3$ is N or H, $X_4$ is E or D (SEQ ID NO: 87); (b) HVR-L2 comprising the amino acid sequence LASTLAS (SEQ ID NO: 81); and (c) HVR-L3 comprising the amino acid sequence $QTYDGISX_1YGVA$, wherein $X_1$ is S or H (SEQ ID NO: 88).

In some embodiments, an isolated anti-myostatin antibody of the present invention comprises a heavy chain variable domain framework FR1 comprising the amino acid sequence of SEQ ID NO: 89; FR2 comprising the amino acid sequence of SEQ ID NO: 90; FR3 comprising the amino acid sequence of SEQ ID NO: 91; and FR4 comprising the amino acid sequence of SEQ ID NO: 92. In some embodiments, an isolated anti-myostatin antibody of the present invention comprises a light chain variable domain framework FR1 comprising the amino acid sequence of SEQ ID NO: 93; FR2 comprising the amino acid sequence of SEQ ID NO: 94; FR3 comprising the amino acid sequence of SEQ ID NO: 95; and FR4 comprising the amino acid sequence of SEQ ID NO: 96.

In some embodiments, an isolated anti-myostatin antibody of the present invention comprises (a) a VH sequence having at least 95% sequence identity to the amino acid sequence of any one of SEQ ID NOs: 48-51; (b) a VL sequence having at least 95% sequence identity to the amino acid sequence of any one of SEQ ID NOs: 52-55; or (c) a VH sequence as in (a) and a VL sequence as in (b). In further embodiments, the antibody comprises a VH sequence of any one of SEQ ID NOs: 48-51. In further embodiments, the antibody comprises a VL sequence of any one of SEQ ID NOs: 52-55.

The invention provides an antibody comprising a VH sequence of any one of SEQ ID NOs: 48-51 and a VL sequence of any one of SEQ ID NOs: 52-55.

The invention also provides isolated nucleic acids encoding an anti-myostatin antibody of the present invention. The invention also provides host cells comprising a nucleic acid of the present invention. The invention also provides a method of producing an antibody comprising culturing a host cell of the present invention so that the antibody is produced.

The invention also provides a pharmaceutical formulation comprising an anti-myostatin antibody of the present invention and a pharmaceutically acceptable carrier.

Anti-myostatin antibodies of the present invention may be for use as a medicament. Anti-myostatin antibodies of the present invention may be for use in treating a muscle wasting disease. Anti-myostatin antibodies of the present invention may be for use in increasing mass of muscle tissue. Anti-myostatin antibodies of the present invention may be for use in increasing strength of muscle tissue.

Anti-myostatin antibodies of the present invention may be used in the manufacture of a medicament. In some embodiments, the medicament is for treatment of a muscle wasting disease. In some embodiments, the medicament is for increasing mass of muscle tissue. In some embodiments, the medicament is for increasing strength of muscle tissue.

The invention also provides a method of treating an individual having a muscle wasting disease. In some embodiments, the method comprises administering to the individual an effective amount of an anti-myostatin antibody of the present invention. The invention also provides a method of increasing mass of muscle tissue in an individual. In some embodiments, the method comprises administering to the individual an effective amount of an anti-myostatin antibody of the present invention to increase mass of muscle tissue. The invention also provides a method of increasing strength of muscle tissue in an individual. In some embodiments, the method comprises administering to the individual an effective amount of an anti-myostatin antibody of the present invention to increase strength of muscle tissue.

BRIEF DESCRIPTION OF DRAWINGS

FIG. 3 illustrates in vivo efficacy of anti-mature myostatin antibodies on muscle mass, as described in Example 5. Each of the anti-mature myostatin antibodies 41C1E4, MST0226-G1m and MST0796-G1m was administered in mice, and lean body mass (LBM) was measured on day 0, 4, 7 and 14. * indicates $p<0.05$,  indicates $p<0.01$, and * indicates $p<0.001$ in comparison to the PBS group by Dunnett's test.

FIG. 4 illustrates in vivo efficacy of anti-mature myostatin antibodies on muscle mass, as described in Example 5. Each of the anti-mature myostatin antibodies 41C1E4, MST0226-G1m and MST0796-G1m was administered in mice, and weight of quadriceps, gastrocnemius, plantaris, masseter, and soleus muscles was measured. The vertical axis shows a percent increment of muscle weight compared to the PBS group. * indicates $p<0.05$,  indicates $p<0.01$, and * indicates $p<0.001$ in comparison to the PBS group by Dunnett's test.

FIG. 5 illustrates inhibition of myostatin activity by anti-mature myostatin antibodies, as described in Example 6. The activity of myostatin was measured using HEK Blue Assay in the presence of an anti-mature myostatin antibody 41C1E4, MSLO00-SG1, MSLO01-SG1, MSLO02-SG1, MSLO03-SG1, or MSLO04-SG1 at various concentrations.

FIG. 6A illustrates plasma total myostatin concentrations measured when the antibody having G1-type Fc region was administered. BLQ (below the limit of quantitation) indicates that the measured concentration was below the lower limit of quantitation in the myostatin concentration measurement assay. FIG. 6B illustrates ratios of (plasma total myostatin concentration measured when the antibody having F760-type Fc region was administered)/(plasma total myostatin concentration measured when the antibody having G1-type Fc region was administered). In this assay, a higher value of the ratio means that the antibody has a higher ability to be taken up into cells with its antigen (mature myostatin) through the interaction of the Fc region of the antibody and Fc gamma R on the cells, which results in enhanced antigen clearance from plasma.

FIG. 7 illustrates in vivo efficacy of anti-mature myostatin antibodies on muscle mass, as described in Example 8. Each of the anti-mature myostatin antibodies MSLO00-SG1 and MSLO03-SG1 was administered at doses of 0.5 mg/kg, 1 mg/kg, 2 mg/kg, 5 mg/kg and 10 mg/kg in mice, and lean body mass (LBM) was measured. The vertical axis shows an increment of LBM between day 0 and day 14.

FIG. 8 illustrates in vivo efficacy of anti-mature myostatin antibodies on grip strength, as described in Example 8. Each of the anti-mature myostatin antibodies MSLO00-SG1 and MSLO03-SG1 was administered at doses of 0.5 mg/kg, 1 mg/kg, 2 mg/kg, 5 mg/kg and 10 mg/kg in mice, and grip strength of the mice was measured. The vertical axis shows an increment of grip strength between day −1 and day 13.

DESCRIPTION OF EMBODIMENTS

Figure 1:
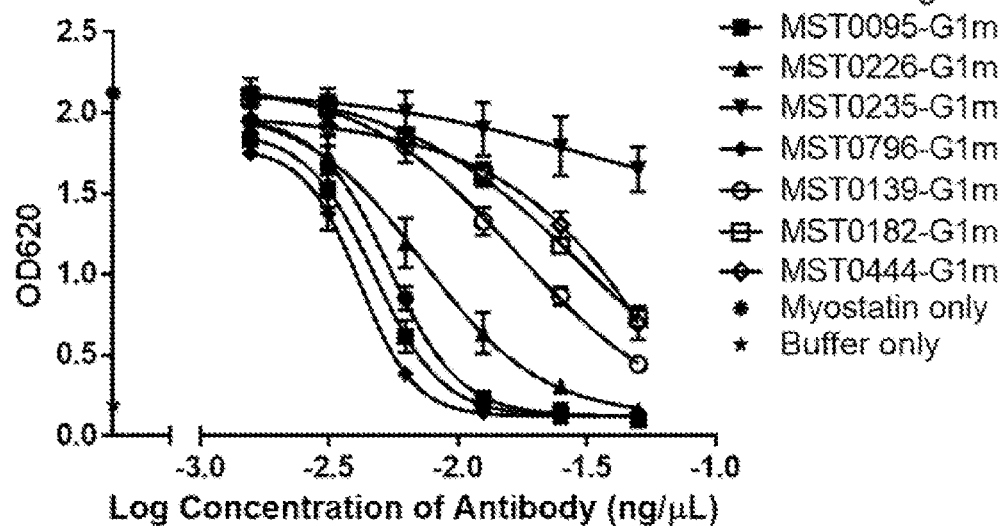
FIG. 1 illustrates inhibition of myostatin activity by anti-mature myostatin antibodies, as described in Example 3. The activity of myostatin was measured using HEK Blue Assay in the presence of an anti-mature myostatin antibody 41C1E4, MST0095-G1m, MST0226-G1m, MST0235-G1m, MST0796-G1m, MST0139-G1m, MST0182-G1m, or MST0444-G1m at various concentrations.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3d edition (2001) Cold Spring Harbor Laboratory Press, Cold Spring Harbor, N.Y.; Current Protocols in Molecular Biology (F. M. Ausubel, et al. eds., (2003)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, A Laboratory Manual, and Animal Cell Culture (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane, Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

I. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application. All references cited herein, including patent applications and publications, are incorporated by reference in their entirety.

For purposes of interpreting this specification, the following definitions will apply and whenever appropriate, terms used in the singular will also include the plural and vice versa. It is to be understood that the terminology used herein is for the purpose of describing particular embodiments only, and is not intended to be limiting. In the event that any definition set forth below conflicts with any document incorporated herein by reference, the definition set forth below shall control.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-myostatin antibody" and "an antibody that binds to myostatin" refer to an antibody that is capable of binding myostatin with sufficient affinity such that the antibody is useful as a diagnostic and/or therapeutic agent in targeting myostatin. In one embodiment, the extent of binding of an anti-myostatin antibody to an unrelated, non-myostatin protein is less than about 10% of the binding of the antibody to myostatin as measured, e.g., by a radioimmunoassay (RIA). In certain embodiments, an antibody that binds to myostatin has a dissociation constant (Kd) of 1 micro M or less, 100 nM or less, 10 nM or less, 1 nM or less, 0.1 nM or less, 0.01 nM or less, or 0.001 nM or less (e.g. $10^{-8}$ M or less, e.g. from $10^{-8}$M to $10^{-13}$ M, e.g., from $10^{-9}$M to $10^{-13}$ M). In certain embodiments, an anti myostatin antibody binds to an epitope of myostatin that is conserved among myostatin from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay, and/or conversely, the reference antibody blocks binding of the antibody to its antigen in a competition assay. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called alpha, delta, epsilon, gamma, and mu, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamycin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1 q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" includes any determinant capable of being bound by an antibody. An epitope is a region of an antigen that is bound by an antibody that targets that antigen, and includes specific amino acids that directly contact the antibody. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the Fc gamma RI, Fc gamma RII, and Fc gamma RIII subclasses, including allelic variants and alternatively spliced forms of those receptors. Fc gamma RII receptors include Fc gamma RIIA (an "activating receptor") and Fc gamma RIIB (an "inhibiting receptor"), which have similar amino acid sequences that differ primarily in the cytoplasmic domains thereof. Activating receptor Fc gamma RIIA contains an immunoreceptor tyrosine-based activation motif (ITAM) in its cytoplasmic domain. Inhibiting receptor Fc gamma RIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.). Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. J. Biol. Chem. 9(2):6591-6604 (2001).

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-myostatin antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (kappa) and lambda (lambda), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, CA, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "myostatin", as used herein, refers to any native myostatin from any vertebrate source, including mammals such as primates (e.g. humans) and rodents (e.g., mice and rats), unless otherwise indicated. The term encompasses "full-length", unprocessed myostatin as well as any form of myostatin that results from processing in the cell. The term also encompasses naturally occurring variants of myostatin, e.g., splice variants or allelic variants. The amino acid sequence of an exemplary human myostatin (promyostatin) is shown in SEQ ID NO: 1. The amino acid sequence of an exemplary C-terminal growth factor domain of human myostatin is shown in SEQ ID NO: 2. The amino acid sequence of an exemplary N-terminal propeptide domain of human myostatin is shown in SEQ ID NO: 97 or 100. Active mature myostatin is a disulfide-bonded homodimer consisting of two C-terminal growth factor domains. Inactive latent myostatin is a noncovalently-associated complex of two propeptides and the mature myostatin. The amino acid sequence of an exemplary cynomolgus monkey and murine myostatin (promyostatin) are shown in SEQ ID NO: 3 and 5, respectively. The amino acid sequence of an exemplary C-terminal growth factor domain of cynomolgus monkey and murine myostatin are shown in SEQ ID NO: 4 and 6, respectively. The amino acid sequence of an exemplary N-terminal propeptide domain of cynomolgus monkey and murine myostatin are shown in SEQ ID NO: 98 or 101, and 99 or 102, respectively. Amino acid residues 1-24 of SEQ ID NOs: 1, 3, 5, 100, 101, and 102 correspond to a signal sequence that is removed during processing in the cell and is thus missing from the exemplary amino acid sequence shown in SEQ ID NOs: 97, 98, and 99.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W. H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

In one aspect, the invention is based, in part, on anti-myostatin antibodies and uses thereof. In certain embodiments, antibodies that bind to myostatin are provided. Antibodies of the invention are useful, e.g., for the diagnosis or treatment of a muscle wasting disease.

A. Exemplary Anti-myostatin Antibodies

In one aspect, the invention provides isolated antibodies that bind to myostatin. In certain embodiments, an anti-myostatin antibody of the present invention binds to mature myostatin. Mature myostatin is a disulfide-bonded homodimer of a polypeptide having an amino acid sequence of, for example, SEQ ID NO: 2 in human, SEQ ID NO: 4 in cynomolgus monkey, and SEQ ID NO: 6 in mouse. In some embodiments, an anti-myostatin antibody of the present invention forms a complex with the antigen, myostatin (also described herein as an antigen-antibody complex or an immune complex). In a further embodiment, the antigen-antibody complex comprises at least two antibody molecules of the present invention. In a further embodiment, the antigen-antibody complex comprises at least two antigen molecules. In a further embodiment, the antigen-antibody complex comprises at least two myostatin mature form molecules.

In some embodiments, an anti-myostatin antibody of the present invention is taken up into cells. In another embodiments, an antigen-antibody complex formed by an anti-myostatin antibody of the present invention is taken up into cells. In further embodiments, uptake of an anti-myostatin antibody of the present invention into cells is enhanced when the antibody forms a complex with the antigen. In further embodiments, uptake of the antibody is enhanced when the antibody forms a complex with the antigen compared with when the antibody does not form a complex with the antigen. Enhanced uptake of an antigen-antibody complex into cells can lead to enhanced antigen clearance from plasma when the antibody is administered in a subject. In another embodiment, clearance of the antigen from plasma is enhanced when an anti-myostatin antibody of the present invention is administered in a subject.

In some embodiments, an anti-myostatin antibody of the present invention is taken up into cells through the interaction between an Fc region of the antibody and an Fc receptor on the surface of the cells. In certain embodiment, the Fc region of an anti-myostatin antibody of the present invention has an Fc receptor-binding activity. In further embodiments, the Fc receptor can be Fc gamma receptor (Fc gamma R), which includes, for example, Fc gamma RI including isoforms Fc gamma RIa, Fc gamma RIb, and Fc gamma RIc; Fc gamma RII including isoforms Fc gamma RIIa (including allotypes H131 (type H) and R131 (type R)), Fc gamma RIIb (including Fc gamma RIIb-1 and Fc gamma RIIb-2), and Fc gamma RIIc; and Fc gamma RIII including isoforms Fc gamma RIIIa (including allotypes V158 and F158), and Fc gamma RIIIb (including allotypes Fc gamma RIIIb-NA1 and Fc gamma RIIIb-NA2).

In another embodiment, an anti-myostatin antibody of the present invention shows higher uptake into cells when compared with an antibody which is identical to the anti-myostatin antibody except that the Fc region has no Fc gamma R-binding activity. In further embodiment, an anti-myostatin antibody of the present invention shows at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6.0, 7.0, 8.0, 9.0, 10, 20, 50, 100, 200, 500, or 1000 fold higher uptake into cells when compared with an antibody which is identical to the anti-myostatin antibody except that the Fc region has no Fc gamma R-binding activity. In another embodiment, when compared between two antibodies both of which are constructed by modifying an anti-myostatin antibody of the present invention, one of which is an antibody having an Fc region with Fc gamma R binding activity and the other of which is an antibody having an Fc region without Fc gamma R binding activity, the former antibody shows higher uptake into cells than the latter antibody. In certain embodiments, a modified antibody having a heavy chain constant region of G1m (SEQ ID NO: 7) or SG1 (SEQ ID NO: 64) can be used as an antibody having an Fc region with Fc gamma R binding activity. In certain embodiments, a modified antibody having a heavy chain constant region of F760 (SEQ ID NO: 68) can be used as an antibody having an Fc region without Fc gamma R binding activity. In further embodiments, the former antibody shows at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6.0, 7.0, 8.0, 9.0, 10, 20, 50, 100, 200, 500, or 1000 fold higher uptake into cells than the latter antibody.

In another aspect, the invention provides anti-myostatin antibodies that exhibit pH-dependent binding characteristics. As used herein, the expression "pH-dependent binding" means that the antibody exhibits "reduced binding to myostatin at acidic pH as compared to its binding at neutral pH" (for purposes of the present disclosure, both expressions may be used interchangeably). For example, antibodies "with pH-dependent binding characteristics" include antibodies that bind to myostatin with higher affinity at neutral pH than at acidic pH. In certain embodiments, the antibodies of the present invention bind to myostatin with at least 2, 3, 5, 10, 15, 20, 25, 30, 35, 40, 45, 50, 55, 60, 65, 70, 75, 80, 85, 90, 95, 100, 200, 400, 1000, 10000, or more times higher affinity at neutral pH than at acidic pH.

When an antigen is a soluble protein, the binding of an antibody to the antigen can result in an extended half-life of the antigen in plasma (i.e., reduced clearance of the antigen from plasma), since the antibody can have a longer half-life in plasma than the antigen itself and may serve as a carrier for the antigen. This is due to the recycling of the antigen-antibody complex by FcRn through the endosomal pathway in cell (Roopenian and Akilesh (2007) Nat Rev Immunol 7(9): 715-725). However, an antibody with pH-dependent binding characteristics, which binds to its antigen in neutral extracellular environment while releasing the antigen into acidic endosomal compartments following its entry into cells, is expected to have superior properties in terms of antigen neutralization and clearance relative to its counterpart that binds in a pH-independent manner (Igawa et al (2010) Nature Biotechnol 28(11); 1203-1207; Devanaboyina et al (2013) mAbs 5(6): 851-859; International Patent Application Publication No: WO 2009/125825).

The "affinity" of an antibody for myostatin, for purposes of the present disclosure, is expressed in terms of the KD of the antibody. The KD of an antibody refers to the equilibrium dissociation constant of an antibody-antigen interaction. The greater the KD value is for an antibody binding to its antigen, the weaker its binding affinity is for that particular antigen. Accordingly, as used herein, the expression "higher affinity at neutral pH than at acidic pH" (or the equivalent expression "pH-dependent binding") means that the KD of the antibody binding to myostatin at acidic pH is greater than the KD of the antibody binding to myostatin at neutral pH. For example, in the context of the present invention, an antibody is considered to bind to myostatin with higher affinity at neutral pH than at acidic pH if the KD of the antibody binding to myostatin at acidic pH is at least 2 times greater than the KD of the antibody binding to myostatin at neutral pH. Thus, the present invention includes antibodies that bind to myostatin at acidic pH with a KD that is at least 2, 3, 5, 10, 15, 20, 25, 30, 35, 40, 45, 50, 55, 60, 65, 70, 75, 80, 85, 90, 95, 100, 200, 400, 1000, 10000, or more times greater than the KD of the antibody binding to myostatin at neutral pH. In another embodiment, the KD value of the antibody at neutral pH can be $10^{-7}$M, $10^{-8}$ M, $10^{-9}$M, $10^{-10}$ M, $10^{-11}$M, $10^{-12}$ M, or less. In another embodiment, the KD value of the antibody at acidic pH can be $10^{-9}$ M, $10^{-8}$ M, $10^{-7}$ M, $10^{-6}$ M, or greater.

The binding properties of an antibody for a particular antigen may also be expressed in terms of the kd of the antibody. The kd of an antibody refers to the dissociation rate constant of the antibody with respect to a particular antigen and is expressed in terms of reciprocal seconds (i.e., $sec^{-1}$). An increase in kd value signifies weaker binding of an antibody to its antigen. The present invention therefore includes antibodies that bind to myostatin with a higher kd value at acidic pH than at neutral pH. The present invention includes antibodies that bind to myostatin at acidic pH with a kd that is at least 2, 3, 5, 10, 15, 20, 25, 30, 35, 40, 45, 50, 55, 60, 65, 70, 75, 80, 85, 90, 95, 100, 200, 400, 1000, 10000, or more times greater than the kd of the antibody binding to myostatin at neutral pH. In another embodiment, the kd value of the antibody at neutral pH can be $10^{-2}$ 1/s, $10^{-3}$ 1/s, $10^{4}$ 1/s, $10^{-5}$ 1/s, $10^{-6}$ 1/s, or less. In another embodiment, the kd value of the antibody at acidic pH can be $10^{-3}$ 1/s, $10^{-2}$ 1/s, $10^{4}$ 1/s, or greater.

In certain instances, a "reduced binding to myostatin at acidic pH as compared to its binding at neutral pH" is expressed in terms of the ratio of the KD value of the antibody binding to myostatin at acidic pH to the KD value of the antibody binding to myostatin at neutral pH (or vice versa). For example, an antibody may be regarded as exhibiting "reduced binding to myostatin at acidic pH as compared to its binding at neutral pH", for purposes of the present invention, if the antibody exhibits an acidic/neutral KD ratio of 2 or greater. In certain exemplary embodiments, the acidic/neutral KD ratio for an antibody of the present invention can be 2, 3, 5, 10, 15, 20, 25, 30, 35, 40, 45, 50, 55, 60, 65, 70, 75, 80, 85, 90, 95, 100, 200, 400, 1000, 10000, or greater. In another embodiment, the KD value of the antibody at neutral pH can be $10^{-7}$ M, $10^{-8}$ M, $10^{-9}$ M, $10^{-10}$ M, $10^{-11}$ M, $10^{-12}$ M, or less. In another embodiment, the KD value of the antibody at acidic pH can be $10^{-9}$M, $10^{-8}$ M, $10^{-7}$ M, $10^{-6}$ M, or greater.

In certain instances, a "reduced binding to myostatin at acidic pH as compared to its binding at neutral pH" is expressed in terms of the ratio of the kd value of the antibody binding to myostatin at acidic pH to the kd value of the antibody binding to myostatin at neutral pH (or vice versa). For example, an antibody may be regarded as exhibiting "reduced binding to myostatin at acidic pH as compared to its binding at neutral pH", for purposes of the present invention, if the antibody exhibits an acidic/neutral kd ratio of 2 or greater. In certain exemplary embodiments, the acidic/neutral kd ratio for an antibody of the present invention can be 2, 3, 5, 10, 15, 20, 25, 30, 35, 40, 45, 50, 55, 60, 65, 70, 75, 80, 85, 90, 95, 100, 200, 400, 1000, 10000, or greater. In another embodiment, the kd value of the antibody at neutral pH can be $10^{-2}$ 1/s, $10^{-3}$ 1/s, $10^{-4}$ 1/s, $10^{-5}$ 1/s, $10^{-6}$ 1/s, or less. In another embodiment, the kd value of the antibody at acidic pH can be $10^{-3}$ 1/s, $10^{-2}$ 1/s, $10^{-1}$ 1/s, or greater.

As used herein, the expression "acidic pH" means a pH of 4.0 to 6.5. The expression "acidic pH" includes pH values of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, and 6.5. In particular aspects, the "acidic pH" is 5.8.

As used herein, the expression "neutral pH" means a pH of 6.7 to about 10.0. The expression "neutral pH" includes pH values of 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0. In particular aspects, the "neutral pH" is 7.4.

KD values, and kd values, as expressed herein, may be determined using a surface plasmon resonance-based biosensor to characterize antibody-antigen interactions. (See, e.g., Example 6, herein). KD values, and kd values can be determined at 25 degrees C. or 37 degrees C.

An anti-myostatin antibody of the present invention forms a large immune complex with antigen (myostatin). In this invention, a "large" immune complex (i.e. antigen-antibody complex) means an immune complex containing two or more antibody molecules and two or more antigen molecules. Myostatin can form a large immune complex when being bound by an appropriate antibody. Without being bound by a particular theory, this is possible because myostatin (including mature myostatin) exists as a homodimer containing two myostatin molecules (for example, human, cynomolgus monkey and mouse mature myostatin exists as a homodimer of a polypeptide comprising an amino acid sequence of SEQ ID NO: 2, SEQ ID NO: 4, and SEQ ID NO: 6, respectively). Two molecules of an anti-myostatin antibody of the present invention may bind one each to the two myostatin molecules in the homodimer. Furthermore, because an antibody such as IgG is also a homodimer (or a heterotetramer) having two antigen binding sites, one antibody molecule may bind to two antigen molecules which may be in a single homodimer or in separate homodimers. As such, multiple myostatin molecules and multiple antibody molecules can be included in an immune complex formed by myostatin and an anti-myostatin antibody. A large immune complex containing two or more antibody molecules can bind to Fc receptors on a cell surface more strongly than an immune complex containing only one antibody molecule, because multiple interactions (avidity) between multiple Fc regions and Fc receptors caused by the former, large immune complex is larger than a single interaction (affinity) caused by the latter immune complex. Thus, such a large immune complex that can strongly bind to Fc receptors due to avidity effect through the multiple Fc regions in the complex could be efficiently taken up into cells expressing Fc receptors. In one embodiment, an anti-myostatin antibody of the present invention has two antigen-binding domains such as Fab, each of which binds to the same epitope on a myostatin molecule. In another embodiment, an anti-myostatin antibody of the present invention has two antigen-binding domains binding to different epitopes on a myostatin molecule, much like a bispecific antibody.

Furthermore, an antibody with pH-dependent binding characteristics is thought to have superior properties in terms of antigen neutralization and clearance relative to its counterpart that binds in a pH-independent manner (Igawa et al (2010) Nature Biotechnol 28(11); 1203-1207; Devanaboyina et al (2013) mAbs 5(6): 851-859; International Patent Application Publication No: WO 2009/125825). Therefore, an antibody having both properties mentioned above, that is, an antibody which forms a large immune complex containing two or more antibody molecules and which binds to an antigen in a pH-dependent manner, is expected to have even more superior properties for highly accelerated elimination of antigens from plasma (International Patent Application Publication No: WO 2013/081143).

In some embodiments, an anti-myostatin antibody of the present invention has an inhibitory activity against myostatin. In another embodiment, an anti-myostatin antibody of the present invention blocks myostatin signaling through myostatin receptor such as activin receptor type IIB (ActRIIB).

In certain embodiments, an anti-myostatin antibody of the present invention binds to myostatin from more than one species. In further embodiments, the anti-myostatin antibody binds to myostatin from a human and non-human animal. In further embodiments, the anti-myostatin antibody binds to myostatin from human, mouse, and monkey (e.g. cynomolgus, rhesus macaque, marmoset, chimpanzee, or baboon).

In one aspect, the invention provides an anti-myostatin antibody comprising at least one, two, three, four, five, or six HVRs selected from (a) HVR-H1 comprising the amino acid sequence of any one of SEQ ID NOs: 70-71, 84; (b) HVR-H2 comprising the amino acid sequence of any one of SEQ ID NOs: 72-74, 85; (c) HVR-H3 comprising the amino acid sequence of any one of SEQ ID NOs: 75-76, 86; (d) HVR-L1 comprising the amino acid sequence of any one of SEQ ID NOs: 77-80, 87; (e) HVR-L2 comprising the amino acid sequence of SEQ ID NO: 81; and (0 HVR-L3 comprising the amino acid sequence of any one of SEQ ID NOs: 82-83, 88.

In one aspect, the invention provides an antibody comprising at least one, at least two, or all three VH HVR sequences selected from (a) HVR-H1 comprising the amino acid sequence of any one of SEQ ID NOs: 70-71, 84; (b) HVR-H2 comprising the amino acid sequence of any one of SEQ ID NOs: 72-74, 85; and (c) HVR-H3 comprising the amino acid sequence of any one of SEQ ID NOs: 75-76, 86. In one embodiment, the antibody comprises HVR-H3 comprising the amino acid sequence of any one of SEQ ID NOs: 75-76, 86. In another embodiment, the antibody comprises HVR-H3 comprising the amino acid sequence of any one of SEQ ID NOs: 75-76, 86 and HVR-L3 comprising the amino acid sequence of any one of SEQ ID NOs: 82-83, 88. In a further embodiment, the antibody comprises HVR-H3 comprising the amino acid sequence of any one of SEQ ID NOs: 75-76, 86, HVR-L3 comprising the amino acid sequence of any one of SEQ ID NOs: 82-83, 88, and HVR-H2 comprising the amino acid sequence of any one of SEQ ID NOs: 72-74, 85. In a further embodiment, the antibody comprises (a) HVR-H1 comprising the amino acid sequence of any one of SEQ ID NOs: 70-71, 84; (b) HVR-H2 comprising the amino acid sequence of any one of SEQ ID NOs: 72-74, 85; and (c) HVR-H3 comprising the amino acid sequence of any one of SEQ ID NOs: 75-76, 86.

In another aspect, the invention provides an antibody comprising at least one, at least two, or all three VL HVR sequences selected from (a) HVR-L1 comprising the amino acid sequence of any one of SEQ ID NOs: 77-80, 87; (b) HVR-L2 comprising the amino acid sequence of SEQ ID NO: 81; and (c) HVR-L3 comprising the amino acid sequence of any one of SEQ ID NOs: 82-83, 88. In one embodiment, the antibody comprises (a) HVR-L1 comprising the amino acid sequence of any one of SEQ ID NOs: 77-80, 87; (b) HVR-L2 comprising the amino acid sequence of SEQ ID NO: 81; and (c) HVR-L3 comprising the amino acid sequence of any one of SEQ ID NOs: 82-83, 88.

In another aspect, an antibody of the invention comprises (a) a VH domain comprising at least one, at least two, or all three VH HVR sequences selected from (i) HVR-H1 comprising the amino acid sequence of any one of SEQ ID NOs: 70-71, 84, (ii) HVR-H2 comprising the amino acid sequence of any one of SEQ ID NOs: 72-74, 85, and (iii) HVR-H3 comprising the amino acid sequence of any one of SEQ ID NOs: 75-76, 86; and (b) a VL domain comprising at least one, at least two, or all three VL HVR sequences selected from (i) HVR-L1 comprising the amino acid sequence of any one of SEQ ID NOs: 77-80, 87, (ii) HVR-L2 comprising the amino acid sequence of SEQ ID NO: 81, and (iii) HVR-L3 comprising the amino acid sequence of any one of SEQ ID NOs: 82-83, 88.

In another aspect, the invention provides an antibody comprising (a) HVR-H1 comprising the amino acid sequence of any one of SEQ ID NOs: 70-71, 84; (b) HVR-H2 comprising the amino acid sequence of any one of SEQ ID NOs: 72-74, 85; (c) HVR-H3 comprising the amino acid sequence of any one of SEQ ID NOs: 75-76, 86; (d) HVR-L1 comprising the amino acid sequence of any one of SEQ ID NOs: 77-80, 87; (e) HVR-L2 comprising the amino acid sequence of SEQ ID NO: 81; and (0 HVR-L3 comprising the amino acid sequence of any one of SEQ ID NOs: 82-83, 88.

In certain embodiments, any one or more amino acids of an anti-myostatin antibody as provided above are substituted at the following HVR positions:
  in HVR-H1 (SEQ ID NO: 70): positions 1, and 4
  in HVR-H2 (SEQ ID NO: 72): positions 5, 7, and 15
  in HVR-H3 (SEQ ID NO: 75): positions 2, and 10
  in HVR-L1 (SEQ ID NO: 77): positions 4, 7, 8, and 9
  in HVR-L3 (SEQ ID NO: 82): position 8.

In certain embodiments, the substitutions are conservative substitutions, as provided herein. In certain embodiments, any one or more of the following substitutions may be made in any combination:
  in HVR-H1 (SEQ ID NO: 70): N1H; M4K
  in HVR-H2 (SEQ ID NO: 72): S5E; S7E; K15E
  in HVR-H3 (SEQ ID NO: 75): G2H; I10H
  in HVR-L1 (SEQ ID NO: 77): Q4E; S7H; N8H; E9D
  in HVR-L3 (SEQ ID NO: 82): S8H.

All possible combinations of the above substitutions are encompassed by the consensus sequences of SEQ ID NOs: 84, 85, 86, 87, and 88 for HVR-H1, HVR-H2, HVR-H3, HVR-L1, and HVR-L3, respectively.

In any of the above embodiments, an anti-myostatin antibody is humanized. In one embodiment, an anti-myostatin antibody comprises HVRs as in any of the above embodiments, and further comprises an acceptor human framework, e.g. a human immunoglobulin framework or a human consensus framework. In another embodiment, an anti-myostatin antibody comprises HVRs as in any of the above embodiments, and further comprises a VH or VL comprising an FR sequence. In a further embodiment, the anti-myostatin antibody comprises the following heavy chain or light chain variable domain FR sequences: For the heavy chain variable domain, FR1 comprises the amino acid sequence of SEQ ID NO: 89, FR2 comprises the amino acid sequence of SEQ ID NO: 90, FR3 comprises the amino acid sequence of SEQ ID NO: 91, FR4 comprises the amino acid sequence of SEQ ID NO: 92. For the light chain variable domain, FR1 comprises the amino acid sequence of SEQ ID NO: 93, FR2 comprises the amino acid sequence of SEQ ID NO: 94, FR3 comprises the amino acid sequence of SEQ ID NO: 95, FR4 comprises the amino acid sequence of SEQ ID NO: 96.

In another aspect, an anti-myostatin antibody comprises a heavy chain variable domain (VH) sequence having at least 90%, 91%, 92%, 93%, 94%, 95%, 96%, 97%, 98%, 99%, or 100% sequence identity to the amino acid sequence of any one of SEQ ID NOs: 48-51. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence (such as the amino acid sequence of any one of SEQ ID NOs: 48-51), but an anti-myostatin antibody comprising that sequence retains the ability to bind to myostatin. In certain embodiments, a total of 1 to 10 amino acids have been substituted, inserted and/or deleted in any one of SEQ ID NOs: 48-51. In certain embodiments, substitutions, insertions, or deletions occur in regions outside the HVRs (i.e., in the FRs). Optionally, the anti-myostatin antibody comprises the VH sequence in any one of SEQ ID NOs: 48-51, including post-translational modifications of that sequence. In a particular embodiment, the VH comprises one, two or three HVRs selected from: (a) HVR-H1 comprising the amino acid sequence of any one of SEQ ID NOs: 70-71, 84, (b) HVR-H2 comprising the amino acid sequence of any one of SEQ ID NOs: 72-74, 85, and (c) HVR-H3 comprising the amino acid sequence of any one of SEQ ID NOs: 75-76, 86.

In another aspect, an anti-myostatin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of any one of SEQ ID NOs: 52-55. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence (such as the amino acid sequence of any one of SEQ ID NOs: 52-55), but an anti-myostatin antibody comprising that sequence retains the ability to bind to myostatin. In certain embodiments, a total of 1 to 10 amino acids have been substituted, inserted and/or deleted in any one of SEQ ID NOs: 52-55. In certain embodiments, the substitutions, insertions, or deletions occur in regions outside the HVRs (i.e., in the FRs). Optionally, the anti-myostatin antibody comprises the VL sequence in any one of SEQ ID NOs: 52-55, including post-translational modifications of that sequence. In a particular embodiment, the VL comprises one, two or three HVRs selected from (a) HVR-L1 comprising the amino acid sequence of any one of SEQ ID NOs: 77-80, 87; (b) HVR-L2 comprising the amino acid sequence of SEQ ID NO: 81; and (c) HVR-L3 comprising the amino acid sequence of any one of SEQ ID NOs: 82-83, 88.

In another aspect, an anti-myostatin antibody is provided, wherein the antibody comprises a VH as in any of the embodiments provided above, and a VL as in any of the embodiments provided above. In one embodiment, the antibody comprises the VH and VL sequences in any one of SEQ ID NOs: 48-51 and any one of SEQ ID NOs: 52-55, respectively, including post-translational modifications of those sequences.

In certain embodiments, an anti-myostatin antibody of the present invention comprises a VH as in any of the embodiments provided above and a heavy chain constant region comprising the amino acid sequence of any one of SEQ ID NOs: 7, 64, and 68. In certain embodiments, an anti-myostatin antibody of the present invention comprises a VL as in any of the embodiments provided above and a light chain constant region comprising the amino acid sequence of any one of SEQ ID NOs: 9 and 65.

In one aspect, the invention provides an anti-myostatin antibody described in Table 2 or Table 3.

In a further aspect, the invention provides an antibody that binds to the same epitope as an anti-myostatin antibody provided herein. For example, in certain embodiments, an antibody is provided that binds to the same epitope as an antibody described in Table 2 or 3. In certain embodiments, an antibody is provided that binds to the same epitope as any one of the antibodies selected from the group consisting of: MST0226, MST0796, MST0139, MST0182, MSLO00, MSLO01, MSLO02, MSLO03, and MSLO04 described in Example 2 or 6. In another aspect, the invention provides an antibody that competes for binding myostatin with an anti-myostatin antibody provided herein. For example, in certain embodiments, an antibody is provided that competes for binding myostatin with an antibody described in Table 2 or 3. In certain embodiments, an antibody is provided that competes for binding myostatin with any one of the antibodies selected from the group of consisting of: MST0226, MST0796, MST0139, MST0182, MSLO00, MSLO01, MSLO02, MSLO03, and MSLO04 described in Example 2 or 6. It is expected that the epitopes bound by the antibodies described above are located in conformationally appropriate positions to form a large antigen-antibody complex when bound by the antibodies. Therefore, not only the antibodies described above but also antibodies that bind to the same epitopes as them or antibodies that compete for binding myostatin with them would be useful in the present invention.

In a further aspect of the invention, an anti-myostatin antibody according to any of the above embodiments is a monoclonal antibody, including a chimeric, humanized or human antibody. In one embodiment, an anti-myostatin antibody is an antibody fragment, e.g., a Fv, Fab, Fab', scFv, diabody, or F(ab')2 fragment. In another embodiment, the antibody is a full length IgG antibody, e.g., an intact IgG1 or IgG4 antibody or other antibody class or isotype as defined herein.

In a further aspect, an anti-myostatin antibody according to any of the above embodiments may incorporate any of the features, singly or in combination, as described in Sections 1-7 below.

1. Antibody Affinity

In certain embodiments, an antibody provided herein has a dissociation constant (Kd) of 1 micro M or less, 100 nM or less, 10 nM or less, 1 nM or less, 0.1 nM or less, 0.01 nM or less, or 0.001 nM or less (e.g. $10^{-8}$ M or less, e.g. from $10^{-8}$M to $10^{-13}$M, e.g., from $10^{-9}$M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER (registered trademark) multi-well plates (Thermo Scientific) are coated overnight with 5 micro g/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23 degrees C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20 (registered trademark)) in PBS.

When the plates have dried, 150 micro 1/well of scintillant (MICROSCINT-20 ™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE (registered trademark) surface plasmon resonance assay. For example, an assay using a BIACORE (registered trademark)-2000 or a BIACORE (registered trademark)-3000 (BIAcore, Inc., Piscataway, N.J.) is performed at 25 degrees C. with immobilized antigen CM5 chips at ~10 response units (RU). In one embodiment, carboxymethylated dextran biosensor chips (CMS, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 micro g/ml (~0.2 micro M) before injection at a flow rate of 5 micro 1/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25 degrees C. at a flow rate of approximately 25 micro 1/min. Association rates ($k_{on}$) and dissociation rates ($k_{off}$) are calculated using a simple one-to-one Langmuir binding model (BIACORE (registered trademark) Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25 degrees C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')₂, Fv, and scFv fragments, and other fragments described below. For a review of certain antibody fragments, see Hudson et al. Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr.

Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HUMAB (registered trademark) technology; U.S. Pat. No. 7,041,870 describing K-M MOUSE (registered trademark) technology, and U.S. Patent Application Publication No. US 2007/0061900, describing VELOCIMOUSE (registered trademark) technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for myostatin and the other is for any other antigen. In certain embodiments, bispecific antibodies may bind to two different epitopes of myostatin. Bispecific antibodies may also be used to localize cytotoxic agents to cells which express myostatin. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to myostatin as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val, Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or residues that contact antigen, with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be analyzed to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue.

Other insertional variants of the antibody molecule include the fusion to the N- or C-terminus of the antibody to an enzyme (e.g. for ADEPT) or a polypeptide which increases the serum half-life of the antibody.

b) Glycosylation variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about +/−3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc region variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks Fc gamma R binding (hence likely lacking ADCC activity), but retains FcRn binding ability. The primary cells for mediating ADCC, NK cells, express Fc gamma RIII only, whereas monocytes express Fc gamma RI, Fc gamma RII and Fc gamma RIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA); and Cyto-Tox 96 (registered trademark) non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

d) Cysteine engineered antibody variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-myostatin antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., a Y0, NS0, and Sp20 cell). In one embodiment, a method of making an anti-myostatin antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-myostatin antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR$^-$ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Antibodies with pH-dependent characteristics may be obtained by using screening methods and/or mutagenesis methods e.g., as described in WO 2009/125825. The screening methods may comprise any process by which an antibody having pH-dependent binding characteristics is identified within a population of antibodies specific for a particular antigen. In certain embodiments, the screening methods may comprise measuring one or more binding parameters (e.g., KD or kd) of individual antibodies within an initial population of antibodies both at acidic and neutral pH. The binding parameters of the antibodies may be measured using, e.g., surface plasmon resonance, or any other analytic method that allows for the quantitative or qualitative assessment of the binding characteristics of an antibody to a particular antigen. In certain embodiments, the screening methods may comprise identifying an antibody that binds to an antigen with an acidic/neutral KD ratio of 2 or greater. Alternatively, the screening methods may comprise identifying an antibody that binds to an antigen with an acidic/neutral kd ratio of 2 or greater.

In another embodiment, the mutagenesis methods may comprise incorporating a deletion, substitution, or addition of an amino acid within the heavy and/or light chain of the antibody to enhance the pH-dependent binding of the antibody to an antigen. In certain embodiments, the mutagenesis may be carried out within one or more variable domains of the antibody, e.g., within one or more HVRs (e.g., CDRs). For example, the mutagenesis may comprise substituting an amino acid within one or more HVRs (e.g., CDRs) of the antibody with another amino acid. In certain embodiments, the mutagenesis may comprise substituting one or more amino acids in at least one HVR (e.g., CDR) of the antibody with a histidine. In certain embodiments, "enhanced pH-dependent binding" means that the mutated version of the antibody exhibits a greater acidic/neutral KD ratio, or a greater acidic/neutral kd ratio, than the original "parent" (i.e., the less pH-dependent) version of the antibody prior to mutagenesis. In certain embodiments, the mutated version of the antibody has an acidic/neutral KD ratio of 2 or greater. Alternatively, the mutated version of the antibody has an acidic/neutral kd ratio of 2 or greater.

C. Assays

Anti-myostatin antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, BIAcore, etc.

In another aspect, competition assays may be used to identify an antibody that competes for binding to myostatin with any anti-myostatin antibody described herein. In certain embodiments, when such a competing antibody is present in excess, it blocks (e.g., reduces) the binding of a reference antibody to myostatin by at least 10%, 15%, 20%, 25%, 30%, 35%, 40%, 45%, 50%, 55%, 60%, 65%, 70%, 75% or more. In some instances, binding is inhibited by at least 80%, 85%, 90%, 95%, or more. In certain embodiments, such a competing antibody binds to the same epitope (e.g., a linear or a conformational epitope) that is bound by an anti-myostatin antibody described herein (e.g., an anti-myostatin antibody described in Table 2 or 3). Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized myostatin is incubated in a solution comprising a first labeled antibody that binds to myostatin and a second unlabeled antibody that is being tested for its ability to compete with the first antibody for binding to myostatin. The second antibody may be present in a hybridoma supernatant. As a control, immobilized myostatin is incubated in a solution comprising the first labeled antibody but not the second unlabeled antibody. After incubation under conditions permissive for binding of the first antibody to myostatin, excess unbound antibody is removed, and the amount of label associated with immobilized myostatin is measured. If the amount of label associated with immobilized myostatin is substantially reduced in the test sample relative to the control sample, then that indicates that the second antibody is competing with the first antibody for binding to myostatin. See Harlow and Lane (1988) Antibodies: A Laboratory Manual ch.14 (Cold Spring Harbor Laboratory, Cold Spring Harbor, N.Y.).

In another aspect, an antibody that binds to the same epitope as an anti-myostatin antibody provided herein or that competes for binding myostatin with an anti-myostatin antibody provided herein may be identified using sandwich assays. Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. See David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme. An antibody which simultaneously binds to myostatin with an anti-myostatin antibody provided herein can be determined to be an antibody that binds to a different epitope from the anti-myostatin antibody. Therefore, an antibody which does not simultaneously bind to myostatin with an anti-myostatin antibody provided herein can be determined to be an antibody that binds to the same epitope as the anti-myostatin antibody or that competes for binding myostatin with the anti-myostatin antibody.

In one aspect, the binding activity of an Fc region of an antibody towards an Fc receptor (e.g., Fc gamma R) can be measured by the Amplified Luminescent Proximity Homogeneous Assay (ALPHA), the BIACORE method which utilizes the surface plasmon resonance (SPR) phenomena, or such, in addition to ELISA or fluorescence activated cell sorting (FACS) (Proc Natl Acad Sci USA (2006) 103(11): 4005-4010). For example, in the BIACORE method, Fc receptors are subjected to interaction as an analyte with an antibody comprising an Fc region immobilized or captured onto the sensor chips using Protein A, Protein L, Protein A/G, Protein G, anti-lamda chain antibodies, anti-kappa chain antibodies, antigenic peptides, antigenic proteins, or such.

2. Activity Assays

In one aspect, assays are provided for identifying anti-myostatin antibodies having biological activity. Biological activity may include, e.g., an inhibitory activity against myostatin. Antibodies having such biological activity in vivo and/or in vitro are also provided.

In certain embodiments, an antibody of the invention is tested for such biological activity.

In certain embodiments, whether a test antibody has an inhibitory activity against myostatin is determined by detecting mature myostatin activity, for example, the activity of binding to a myostatin receptor, or the activity of mediating signal transduction in a cell expressing a myostatin receptor. Cells useful for such an assay can be those that express an endogenous myostatin receptor, for example, L6 myocytes, or can be those that are genetically modified, transiently or stably, to express a transgene encoding a myostatin receptor, for example, an activin receptor such as an activin type II receptor (See, for example, Thies et al (2001) Growth Factors 18(4): 251-259). Binding of myostatin to a myostatin receptor can be detected by using a receptor binding assay. Myostatin mediated signal transduction can be detected at any level in the signal transduction pathway, for example, by examining phosphorylation of a Smad polypeptide, examining expression of a myostatin regulated gene including a reporter gene, or measuring proliferation of a myostatin-dependent cell. Where a decreased mature myostatin activity is detected in the presence of (or following contact with) the test antibody, the test antibody is identified as an antibody that has an inhibitory activity against myostatin.

Inhibition of myostatin activity can also be detected and/or measured using the methods set forth and exemplified in the working examples. Using assays of these or other suitable types, test antibodies can be screened for those capable of inhibiting myostatin activity. In certain embodiments, inhibition of myostatin activity includes at least a 5%, 10%, 15%, 20%, 25%, 30%, 35%, or 40% or greater decrease of myostatin activity in the assay as compared to a negative control under similar conditions. In some embodiments, it refers to the inhibition of myostatin activity of at least 45%, 50%, 55%, 60%, 65%, 70%, 75%, 80%, 85%, 90%, or 95% or greater.

In certain embodiments, whether a test antibody is taken up into cells can be determined by cell imaging analysis. A fluorescence-labeled antibody is contacted with cells expressing an Fc receptor (e.g., Fc gamma R) in the absence and presence of antigen, and the resulting fluorescence intensity of the cells is measured using an image analyser. Cells useful for such an assay can be those that express an endogenous Fc receptor, or can be those that are genetically modified, transiently or stably, to express a transgene encoding an Fc receptor. Where an increased fluorescence intensity is detected in the presence of the antigen compared with in the absence of the antigen, it is determined that uptake of the test antibody into cells is enhanced when the test antibody is complexed with the antigen.

In another embodiment, uptake of an antibody into cells can be evaluated, for example by detecting formation of an immune complex (such as a "large" immune complex defined above) in vitro. In certain embodiments, formation of an immune complex is detected by a method such as size exclusion (gel filtration) chromatography, ultracentrifugation, light scattering, electron microscope, or mass spectrometry (Mol Immunol (2002) 39: 77-84, Mol Immunol (2009) 47: 357-364). These methods make use of the property that the size of an immune complex containing two or more antibodies is larger than that of an immune complex containing one antibody. Where a large difference is observed between the molecular sizes detected in the presence of the antigen and in the absence of the antigen, it is determined that uptake of the antibody into cells is enhanced when complexed with its antigen. In another embodiments, formation of an immune complex is detected by a binding assay to an Fc receptor (e.g., Fc gamma R) using such as ELISA, FACS, or SPR (surface plasmon resonance assay; for example, using Biacore) (J Biol Chem (2001) 276 (9): 6591-6604; J Immunol Methods (1982) 50: 109-114; J Immunol (2010) 184 (4): 1968-1976; mAbs (2009) 1(5): 491-504). These methods make use of the property that an immune complex containing two or more antibodies can bind to an Fc receptor more strongly than an immune complex containing only one antibody. Where a large difference is observed between the binding signals detected in the presence of the antigen and in the absence of the antigen, it is determined that uptake of the antibody into cells is enhanced when it is complexed with its antigen.

In another embodiment, uptake of an antibody into cells can be evaluated, for example by administering a test antibody to an animal (e.g., a mouse) and measuring the clearance of the antigen from plasma. Where an accelerated elimination of antigens from plasma is observed in a test antibody-administered animal compared to in a reference antibody-administered animal, it is determined that uptake of the test antibody into cells is enhanced when complexed with its antigen. As described above, an antibody which forms an immune complex containing two or more antibodies (and/or two or more antigens) is expected to accelerate the elimination of antigens from plasma. In certain embodiments, an antibody which does not form a large immune complex containing two or more antibodies can be used as a reference antibody. In certain embodiments, the difference between the two antibodies can be evaluated using a ratio of the plasma antigen concentration. For example, a large value of the ratio of (plasma antigen concentration measured in a reference antibody-administered animal)/(plasma antigen concentration measured in a test antibody-administered animal) indicates that the test antibody can accelerate elimination of antigens from plasma compared to the reference antibody and/or that uptake of the test antibody into cells is enhanced as compared to the reference antibody. In certain embodiments, such a large value of the ratio of (plasma antigen concentration measured in a reference antibody-administered animal)/(plasma antigen concentration measured in a test antibody-administered animal) can be at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6.0, 7.0, 8.0, 9.0, 10, 20, 50, 100, 200, 500, or 1000.

In another embodiment, uptake of an antibody into cells can be evaluated, for example by administering a test antibody to an animal (e.g., a mouse) and measuring the clearance of antigen from plasma. As described above, uptake of an immune complex into cells is expected to be caused through the interaction between an Fc region of the antibody and an Fc receptor (e.g., Fc gamma R) on the cells. Therefore, the extent of the cellular uptake of one test antibody can be evaluated by comparing antigen clearance from plasma caused by the test antibody and that caused by a reference antibody, the reference antibody being identical with the test antibody except that it has an Fc region with no Fc receptor (e.g., Fc gamma R) binding activity. In a certain embodiment, the extent of the cellular uptake of one test antibody can be evaluated by making two modified antibodies, one of which has an Fc region with Fc receptor (e.g., Fc gamma R) binding activity and the other of which has an Fc region without Fc receptor (e.g., Fc gamma R) binding activity, and comparing antigen clearance from plasma caused by the two antibodies. The difference in the antibody clearance reflects how large amounts of the test antibody complexed with its antigen are taken up into cells and cleared from plasma through an Fc receptor (e.g., Fc gamma R), and it is determined that the larger the difference is, the higher the uptake of the test antibody into cells is when it is complexed with its antigen. In certain embodiments, a modified antibody having a heavy chain constant region of G1m (SEQ ID NO: 7) or SG1 (SEQ ID NO: 64) can be used as an antibody which has an Fc region with Fc gamma R binding activity. In certain embodiments, a modified antibody having a heavy chain constant region of F760 (SEQ ID NO: 68) can be used as an antibody which has an Fc region without Fc gamma R binding activity. In certain embodiments, the difference between the two antibodies can be evaluated using a ratio of the plasma antigen concentration. For example, a large value of the ratio of (plasma antigen concentration measured in an animal to which the antibody without Fc gamma R binding activity is administered)/(plasma antigen concentration measured in an animal to which the antibody with Fc gamma R binding activity is administered) indicates that the uptake of the test antibody into cells is high. In certain embodiments, such a large value of the ratio of (plasma antigen concentration measured in an animal to which the antibody without Fc gamma R binding activity is administered)/(plasma antigen concentration measured in an animal to which the antibody with Fc gamma R binding activity is administered) can be at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6.0, 7.0, 8.0, 9.0, 10, 20, 50, 100, 200, 500, or 1000.

In those in vivo tests, an antibody can be administered via intradermal, intravenous, intravitreal, subcutaneous, intraperitoneal, parenteral or intramuscular injection. For example, an antibody can be administered via intravenous injection, as exemplified in Example 4. In certain embodiments, an antigen can be externally administered to an animal in addition to an antibody, either by co-injection with an antibody or by a separate steady-state infusion. For example, an antigen can be co-injected with an antibody, as exemplified in Example 4. In certain embodiments, plasma antigen concentration can be measured as free antigen concentration in plasma which means the concentration of the antigen not bound by an antibody in plasma, or total antigen concentration in plasma which means the sum of the concentrations of the antibody-bound antigen and the non-antibody-bound antigen in plasma (Pharm Res. 2006 January; 23 (1): 95-103). For example, plasma antigen concentration can be measured as total antigen concentration in plasma, as exemplified in Example 4. In certain embodiments, plasma antigen concentration can be measured at 15 minutes, 1 hour, 2 hours, 4 hours, 8 hours, 12 hours, 1 day, 2 days, 3 days, 4 days, 7 days, 14 days, 28 days, 56 days, or 84 days after antibody administration. For example, plasma antigen concentration can be measured at 7 days after antibody administration, as exemplified in Example 4.

In certain embodiments, an anti-myostatin antibody of the present invention can be obtained using assays as described above for evaluating cellular uptake of an antibody into cells. For example, such an antibody can be obtained by preparing a group of anti-myostatin antibodies, performing assays as described above on the antibodies, and selecting an antibody whose uptake into cells is determined to be high when complexed with its antigen. In further embodiments, antibodies obtained by immunizing animals against myostatin or obtained by screening antibody libraries against myostatin can be used as a group of anti-myostatin antibodies.

In other embodiments, an anti-myostatin antibody of the present invention can be obtained using competition assays described above for identifying an antibody that competes for binding to myostatin. For example, such an antibody can be obtained by preparing a group of anti-myostatin antibodies, performing competition assays as described above on the antibodies, and selecting an antibody which competes for binding to myostatin with an anti-myostatin antibody described herein. Alternatively, an antibody which competes for binding to myostatin with an anti-myostatin antibody described in Table 2 or 3 can be selected. Alternatively, an antibody which competes for binding to myostatin with any one of the antibodies selected from the group of consisting of: MST0226, MST0796, MST0139, MST0182, MSLO00, MSLO01, MSLO02, MSLO03, and MSLO04 described in Examples 2 or 6 can be selected. In further embodiments, antibodies obtained by immunizing animals against myostatin or obtained by screening antibody libraries against myostatin can be used as a group of anti-myostatin antibodies.

D. Immunoconjugates

The invention also provides immunoconjugates comprising an anti-myostatin antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U. S. A).

E. Methods and Compositions for Diagnostics and Detection

In certain embodiments, any of the anti-myostatin antibodies provided herein is useful for detecting the presence of myostatin in a biological sample. The term "detecting" as used herein encompasses quantitative or qualitative detection. In certain embodiments, a biological sample comprises a cell or tissue, such as serum, whole blood, plasma, biopsy sample, tissue sample, cell suspension, saliva, sputum, oral fluid, cerebrospinal fluid, amniotic fluid, ascites fluid, milk, colostrum, mammary gland secretion, lymph, urine, sweat, lacrimal fluid, gastric fluid, synovial fluid, peritoneal fluid, ocular lens fluid or mucus.

In one embodiment, an anti-myostatin antibody for use in a method of diagnosis or detection is provided. In a further aspect, a method of detecting the presence of myostatin in a biological sample is provided. In certain embodiments, the method comprises contacting the biological sample with an anti-myostatin antibody as described herein under conditions permissive for binding of the anti-myostatin antibody to myostatin, and detecting whether a complex is formed between the anti-myostatin antibody and myostatin. Such method may be an in vitro or in vivo method. In one embodiment, an anti-myostatin antibody is used to select subjects eligible for therapy with an anti-myostatin antibody, e.g. where myostatin is a biomarker for selection of patients.

Exemplary disorders that may be diagnosed using an antibody of the invention include muscular dystrophy (MD; including Duchenne muscular dystrophy), amyotrophic lateral sclerosis (ALS), muscle atrophy, organ atrophy, carpal tunnel syndrome, frailty, congestive obstructive pulmonary disease (COPD), sarcopenia, cachexia, muscle wasting syndromes, HIV-induced muscle wasting, type 2 diabetes, impaired glucose tolerance, metabolic syndrome (including syndrome X), insulin resistance (including resistance induced by trauma, e.g., burns or nitrogen imbalance), adipose tissue disorders (e.g., obesity, dyslipidemia, nonalcoholic fatty liver disease, etc.), osteoporosis, osteopenia, osteoarthritis, and metabolic bone disorders (including low bone mass, premature gonadal failure, androgen suppression, vitamin D deficiency, secondary hyperparathyroidism, nutritional deficiencies, and anorexia nervosa).

In certain embodiments, labeled anti-myostatin antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-myostatin antibody as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX (registered trademark), Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-myostatin antibodies provided herein may be used in therapeutic methods.

In one aspect, an anti-myostatin antibody for use as a medicament is provided. In further aspects, an anti-myostatin antibody for use in treating a muscle wasting disease is provided. In certain embodiments, an anti-myostatin antibody for use in a method of treatment is provided. In certain embodiments, the invention provides an anti-myostatin antibody for use in a method of treating an individual having a muscle wasting disease comprising administering to the individual an effective amount of the anti-myostatin antibody. In one such embodiment, the method further comprises administering to the individual an effective amount of at least one additional therapeutic agent. In further embodiments, the invention provides an anti-myostatin antibody for use in increasing mass of muscle tissue. In certain embodiments, the invention provides an anti-myostatin antibody for use in a method of increasing mass of muscle tissue in an individual comprising administering to the individual an effective amount of the anti-myostatin antibody to increase mass of muscle tissue. In further embodiments, the invention provides an anti-myostatin antibody for use in increasing strength of muscle tissue. In certain embodiments, the invention provides an anti-myostatin antibody for use in a method of increasing strength of muscle tissue in an individual comprising administering to the individual an effective amount of the anti-myostatin antibody to increase strength of muscle tissue. An "individual" according to any of the above embodiments is preferably a human.

In further embodiments, the invention provides an anti-myostatin antibody for use in enhancing the clearance of myostatin from plasma. In certain embodiments, the invention provides an anti-myostatin antibody for use in a method of enhancing the clearance of myostatin from plasma in an individual comprising administering to the individual an effective amount of the anti-myostatin antibody to enhance the clearance of myostatin from plasma. In one embodiment, an anti-myostatin antibody which forms a large immune complex containing two or more antibody molecules enhances the clearance of myostatin from plasma, compared to an anti-myostatin antibody which does not form such a large immune complex. In another embodiment, an anti-myostatin antibody with pH-dependent binding characteristics enhances the clearance of myostatin from plasma, compared to an anti-myostatin antibody which does not have pH-dependent binding characteristics. In a further embodiment, an anti-myostatin antibody with a pH-dependent binding characteristic between binding at pH5.8 and pH7.4 enhances the clearance of myostatin from plasma, compared to an anti-myostatin antibody which does not have pH-dependent binding characteristics. In a further embodiment, an anti-myostatin antibody having both properties, that is, an antibody which forms a large immune complex containing two or more antibody molecules and which has pH-dependent binding characteristics, enhances the clearance of myostatin from plasma. An "individual" according to any of the above embodiments is preferably a human.

In a further aspect, the invention provides the use of an anti-myostatin antibody in the manufacture or preparation of a medicament. In one embodiment, the medicament is for treatment of a muscle wasting disease. In a further embodiment, the medicament is for use in a method of treating a muscle wasting disease comprising administering to an individual having a muscle wasting disease an effective amount of the medicament. In one such embodiment, the method further comprises administering to the individual an effective amount of at least one additional therapeutic agent. In a further embodiment, the medicament is for increasing mass of muscle tissue. In a further embodiment, the medicament is for use in a method of increasing mass of muscle tissue in an individual comprising administering to the individual an effective amount of the medicament to increase mass of muscle tissue. In a further embodiment, the medicament is for increasing strength of muscle tissue. In a further embodiment, the medicament is for use in a method of increasing strength of muscle tissue in an individual comprising administering to the individual an effective amount of the medicament to increase strength of muscle tissue. An "individual" according to any of the above embodiments may be a human.

In a further embodiment, the medicament is for enhancing the clearance of myostatin from plasma. In a further embodiment, the medicament is for use in a method of enhancing the clearance of myostatin from plasma in an individual comprising administering to the individual an effective amount of the medicament to enhance the clearance of myostatin from plasma. An "individual" according to any of the above embodiments is preferably a human.

In a further aspect, the invention provides a method for treating a muscle wasting disease. In one embodiment, the method comprises administering to an individual having such a muscle wasting disease an effective amount of an anti-myostatin antibody. In one such embodiment, the method further comprises administering to the individual an effective amount of at least one additional therapeutic agent. An "individual" according to any of the above embodiments may be a human.

In a further aspect, the invention provides a method for increasing mass of muscle tissue in an individual. In one embodiment, the method comprises administering to the individual an effective amount of an anti-myostatin antibody to increase mass of muscle tissue. In one embodiment, an "individual" is a human.

In a further aspect, the invention provides a method for increasing strength of muscle tissue in an individual. In one embodiment, the method comprises administering to the individual an effective amount of an anti-myostatin antibody to increase strength of muscle tissue. In one embodiment, an "individual" is a human.

In a further embodiment, the invention provides a method for enhancing the clearance of myostatin from plasma in an individual. In one embodiment, the method comprises administering to the individual an effective amount of an anti-myostatin antibody to enhance the clearance of myostatin from plasma. In one embodiment, an "individual" is a human.

In a further aspect, the invention provides pharmaceutical formulations comprising any of the anti-myostatin antibodies provided herein, e.g., for use in any of the above therapeutic methods. In one embodiment, a pharmaceutical formulation comprises any of the anti-myostatin antibodies provided herein and a pharmaceutically acceptable carrier.

In another embodiment, a pharmaceutical formulation comprises any of the anti-myostatin antibodies provided herein and at least one additional therapeutic agent.

In a further aspect, the pharmaceutical formulation is for treatment of a muscle wasting disease. In a further embodiment, the pharmaceutical formulation is for increasing mass of muscle tissue. In a further embodiment, the pharmaceutical formulation is for increasing strength of muscle tissue. In a further embodiment, the pharmaceutical formulation is for enhancing the clearance of myostatin from plasma. In one embodiment, the pharmaceutical formulation is administered to an individual having a muscle wasting disease. An "individual" according to any of the above embodiments is preferably a human.

It is believed that an anti-myostatin antibody which can form a large immune complex, for example an immune complex containing two or more antibodies and two or more antigens, can be taken up into cells efficiently, and such enhanced uptake of an immune complex into cells can lead to enhanced antigen clearance from plasma, compared to a conventional anti-myostatin antibody which does not form a large immune complex. An anti-myostatin antibody which additionally has pH-dependent antigen binding characteristics would be able to further enhance antigen clearance from plasma, since such an antibody can bind to the antigen in neutral extracellular environment and release it into acidic endosomal compartments following the uptake of the antigen-antibody complex into cells.

In a further aspect, the invention provides methods for preparing a medicament or a pharmaceutical formulation, comprising mixing any of the anti-myostatin antibodies provided herein with a pharmaceutically acceptable carrier, e.g. for use in any of the above therapeutic methods. In one embodiment, the methods for preparing a medicament or a pharmaceutical formulation further comprise adding at least one additional therapeutic agent to the medicament or pharmaceutical formulation.

In certain embodiments, a muscle wasting disease is selected from the group consisting of muscular dystrophy (MD; including Duchenne muscular dystrophy), amyotrophic lateral sclerosis (ALS), muscle atrophy, organ atrophy, carpal tunnel syndrome, frailty, congestive obstructive pulmonary disease (COPD), sarcopenia, cachexia, muscle wasting syndromes, HIV-induced muscle wasting, type 2 diabetes, impaired glucose tolerance, metabolic syndrome (including syndrome X), insulin resistance (including resistance induced by trauma, e.g., burns or nitrogen imbalance), adipose tissue disorders (e.g., obesity, dyslipidemia, nonalcoholic fatty liver disease, etc.), osteoporosis, osteopenia, osteoarthritis, and metabolic bone disorders (including low bone mass, premature gonadal failure, androgen suppression, vitamin D deficiency, secondary hyperparathyroidism, nutritional deficiencies, and anorexia nervosa).

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-myostatin antibody and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 micro g/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 micro g/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

It is understood that any of the above formulations or therapeutic methods may be carried out using an immunoconjugate of the invention in place of or in addition to an anti-myostatin antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-myostatin antibody.

III. EXAMPLES

The following are examples of methods and compositions of the invention. It is understood that various other embodiments may be practiced, given the general description provided above.

Example 1

Expression and Purification of Human, Cynomolgus Monkey, and Mouse Myostatin Mature Form Human latent myostatin (also described herein as myostatin latent form) (SEQ ID NO:1) was expressed transiently using FreeStyle293-F cell line (Thermo Fisher, Carlsbad, CA, USA). Conditioned media containing expressed human myostatin latent form was acidified to pH 6.8 and diluted with ½ vol of milliQ water, followed by application to a Q-sepharose FF anion exchange column (GE healthcare, Uppsala, Sweden). The flow-through fraction was adjusted to pH 5.0 and applied to a SP-sepharose HP cation exchange column (GE healthcare, Uppsala, Sweden), and then eluted with a NaCl gradient. Fractions containing the human myostatin latent form were collected and subsequently subjected to a Superdex 200 gel filtration column (GE healthcare, Uppsala, Sweden) equilibrated with 1× PBS. Fractions containing the human myostatin latent form were then pooled and stored at −80 degrees C.

Human mature myostatin (also described herein as myostatin mature form) (SEQ ID NO: 2) was purified from the purified latent form. The latent form was acidified by addition of 0.1% trifluoroacetic acid (TFA) and applied to a Vydac 214TP C4 reverse phase column (Grace, Deerfield, IL, USA) and eluted with a TFA/CH$_3$CN gradient. Fractions containing mature myostatin were pooled, dried and stored at −80 degrees C. To reconstitute, mature myostatin was dissolved in 4 mM HCl.

Expression and purification of myostatin latent and mature form from cynomolgus monkey (cynomolgus or cyno) (SEQ ID NOs: 3 and 4, respectively) and mouse (SEQ ID NOs: 5 and 6, respectively) were all done exactly the same way as the human counterpart.

The sequence homology of myostatin mature form among human, cynomolgus monkey and mouse are 100% identical, therefore in all the necessary experiments, regardless of species, SEQ ID NO: 2 was used as myostatin mature form (recombinant mature myostatin).

Example 2

Identification of Anti-Mature Myostatin Antibody

Anti-mature myostatin antibodies were prepared, selected, and assayed as follows.

Twelve to sixteen week old NZW rabbits were immunized intradermally with human mature myostatin, human latent myostatin or mature myostatin conjugated with KLH (50-100 micro g/dose/rabbit). This dose was repeated 4-5 times. One week after the final immunization, the spleen and blood from immunized rabbit was collected. Antigen-specific B-cells were stained with labelled antigen, sorted with FCM cell sorter (FACS aria III, BD), and plated in 96-well plates at one cell/well density together with 25,000 cells/well of EL4 cells (European Collection of Cell Cultures) and with rabbit T-cell conditioned medium diluted 20 times, and were cultured for 7-12 days. EL4 cells were treated with mitomycin C (Sigma) for 2 hours and washed 3 times in advance. The rabbit T-cell conditioned medium was prepared by culturing rabbit thymocytes in RPMI-1640 containing Phytohemagglutinin-M (Roche), phorbol 12-myristate 13-acetate (Sigma) and 2% FBS. After cultivation, B-cell culture supernatants were collected for further analysis and pellets were cryopreserved.

ELISA assay was used to test specificity of antibodies in B-cell culture supernatant. Streptavidin (GeneScript) was coated onto a 384-well MAXISorp (Nunc) at 50 nM in PBS for 1 hour at room temperature. Plates were then blocked with Blocking One (Nacalai Tesque) diluted 5 times. Human latent myostatin or mature myostatin was labelled with NHS-PEG4-Biotin (PIERCE) and was added to the blocked ELISA plates, incubated for 1 hour, and washed with Tris-buffered saline with 0.05% Tween-20 (TBS-T). B-cell culture supernatants were added to the ELISA plates, incubated for 1 hour, and washed with TBS-T. Binding was detected by goat anti-rabbit IgG-horseradish peroxidase (BETHYL) followed by the addition of ABTS (KPL).

A total of 28,547 of B-cell lines were screened for binding to mature myostatin and/or human latent myostatin and 1154 lines were selected and designated MST0001-0254, 0288-0629, 0633-0676, 0760-0909, 0911-0931, and 1120-1462. RNA was purified from corresponding cell pellets by using ZR-96 Quick-RNA kits (ZYMO RESEARCH).

The DNA of their variable regions of the heavy and light chain were amplified by reverse transcription PCR and cloned into expression vectors with the heavy chain constant region G1m sequence (SEQ ID NO: 8 (the amino acid sequence is shown in SEQ ID NO: 7)) and with the light chain constant region k0MTC (SEQ ID NO: 10 (the amino acid sequence is shown in SEQ ID NO: 9)) or k0MC sequence (SEQ ID NO: 11 (the amino acid sequence is shown in SEQ ID NO: 9)), respectively. Recombinant antibodies were expressed transiently using the FreeStyle FS293-F cells and 293fectin (Life technologies), according to the manufacturer's instructions. Culture supernatant or recombinant antibodies were used for screening. Recombinant antibodies were purified with protein A (GE Healthcare) and eluted in D-PBS, TBS (Tris-buffered saline), or His buffer (20 mM Histidine, 150 mM NaCl, pH6.0). Size exclusion chromatography was further conducted to remove high molecular weight and/or low molecular weight component, if necessary. Several recombinant antibodies of which sequences are shown in Table 2 were selected for further experiments below.

TABLE 2

Anti-mature myostatin antibodies and their DNA and amino acid sequences (shown as SEQ ID NOs)

| Antibody name | Abbreviation | Variable region | | | | Constant region | | | |
| --- | --- | --- | --- | --- | --- | --- | --- | --- | --- |
| | | Heavy | | Light | | Heavy | | Light | |
| | | DNA | Protein | DNA | Protein | DNA | Protein | DNA | Protein |
| MS_MST0095Hf-G1m/MST0095Lf-kOMTC | MST0095-G1m or MST0095-G1 | 30 | 12 | 39 | 21 | 8 | 7 | 10 | 9 |
| MS_MST0226Hc-G1m/MST0226La-kOMTC | MS10226-G1m or MS10226-G1 | 31 | 13 | 40 | 22 | 8 | 7 | 10 | 9 |
| MS_MST0235Hc-G1m/MST0235Lc-kOMTC | MS10235-G1m, MS10235-G1, or MST0235Hc-G1m | 32 | 14 | 41 | 23 | 8 | 7 | 10 | 9 |
| MS_MST0796Hg-G1m/MST0796La-kOMTC | MS10796-G1m or MS10796-G1 | 33 | 15 | 42 | 24 | 8 | 7 | 10 | 9 |
| MS_MST0139Ha-G1m/MST0139Lc-kOMTC | MST0139-G1m, MST0139-G1, or MST0139Ha-G1m | 34 | 16 | 43 | 25 | 8 | 7 | 10 | 9 |
| MS_MST0182Hc-G1m/MST0182La-kOMTC | MST0182-G1m, MST0182-G1, or MST0182Hc-G1m | 35 | 17 | 44 | 26 | 8 | 7 | 10 | 9 |
| MS_MST0711Ha-G1m/MST0711Lb-kOMTC | MST0711-G1m, MST0711-G1, or MST0711Ha-G1m | 36 | 18 | 45 | 27 | 8 | 7 | 10 | 9 |
| MS_MST0250Hc-G1m/MST0250Ld-kOMTC | MST0250-G1m, MST0250-G1, or MST0250Hc-G1m | 37 | 19 | 46 | 28 | 8 | 7 | 10 | 9 |
| MS_MST0444Hb-G1m/MST0444La-kOMTC | MS10444-G1m, MS10444-G1, or MST0444Hb-G1m | 38 | 20 | 47 | 29 | 8 | 7 | 10 | 9 |

Example 3

Characterization of Anti-Mature Myostatin Antibody (HEK Blue Assay (BMP-1 Activation))

Reporter gene assay was used to assess the biological activity of active myostatin in vitro. HEK-Blue™ TGF-beta cells (Invivogen), which express a Smad3/4-binding elements (SBE)-inducible SEAP (Secreted embryonic alkaline phosphatase) reporter genes, allow the detection of bioactive myostatin by monitoring the activation of the activin type 1 and type 2 receptors. Myostatin mature form stimulates the production of SEAP into cell supernatant by activating Smad3/4 signal through the binding to its receptor. The quantity of SEAP secreted is then assessed using QUAN-TIBlue™ (Invivogen).

HEK-Blue™ TGF-beta cells were maintained in DMEM medium (Gibco) supplemented with 10% fetal bovine serum, 50 micro g/mL streptomycin, 50 U/mL penicillin, 100 micro g/mL Normocin™, 30 micro g/mL of Blasticidin, 200 micro g/mL of HygroGold™ and 100 micro g/mL of Zeocin™. During functional assay, cells were changed to assay medium (DMEM with 0.1% bovine serum albumin, streptomycin, penicillin and Normocin™) and seeded to 96-well plate. Recombinant mature myostatin and anti-mature myostatin antibody were incubated at 37 degrees C. for 30 minutes. The sample mixtures were transferred to cells. After 20-hour incubation, cell supernatant was mixed with QUANTIBlue™ and the optical density at 620 nm was measured in a colorimetric plate reader.

41C1E4 and MYO029 were used as positive controls. Both 41C1E4 and MY029 are anti-mature myostatin antibodies and their sequences are described in U.S. Pat. No. 7,632,499 and WO2004037861, respectively.

As shown as FIG. 1, all anti-mature myostatin antibodies inhibited the secretion of SEAP. This indicates that the antibodies block the binding of mature myostatin to its receptor.

Example 4

Comparison of Plasma Total Myostatin Concentration Between Antibodies with Fc Gamma R Binding and with Abolished Fc Gamma R Binding in Mice In Vivo Test Using C.B-17 Scid Mice The kinetics of total exogenous and endogenous myostatin was assessed in vivo upon administration of an anti-mature myostatin antibody and recombinant mature myostatin in C.B-17 scid mice (In Vivos, Singapore). An anti-mature myostatin antibody (0.6 mg/ml) and recombinant mature myostatin (0.05 mg/ml) was administered at a single dose of 10 ml/kg into the caudal vein. Blood was collected at 7 days after administration. The collected blood was centrifuged immediately at 14,000 rpm in 4 degrees C. for 10 minutes to separate the plasma. The separated plasma was stored at or below −80 degrees C. until measurement. The anti-mature myostatin antibodies used are those prepared based on MST0226, MST0796, MST0139, MST0182, 41C1E4 and MY0029 which are described above. To assess the effects of Fc gamma R binding on myostatin accumulation, two types of modified anti-mature myostatin antibodies were generated, one having an Fc region with Fc gamma R binding activity and the other having an Fc region without Fc gamma R binding activity (also described herein as silent Fc). Heavy chain constant regions G1m (amino acid sequence SEQ ID NO: 7, nucleotide sequence SEQ ID NO: 8) and SG1 (amino acid sequence SEQ ID NO: 64, nucleotide sequence SEQ ID NO: 66) described herein include an Fc region with Fc gamma R binding activity, and F760 (amino acid sequence SEQ ID NO: 68, nucleotide sequence SEQ ID NO: 69) include an Fc region without Fc gamma R binding activity. Binding affinity of G1m and SG1 against human Fc gamma Rs are comparable to that of natural human IgG1. On the other hand, binding affinity of F760 is abolished by amino acid modification in the Fc region.

Measurement of Total Myostatin Concentration in Plasma by Electrochemiluminescence (ECL)

Figure 2:
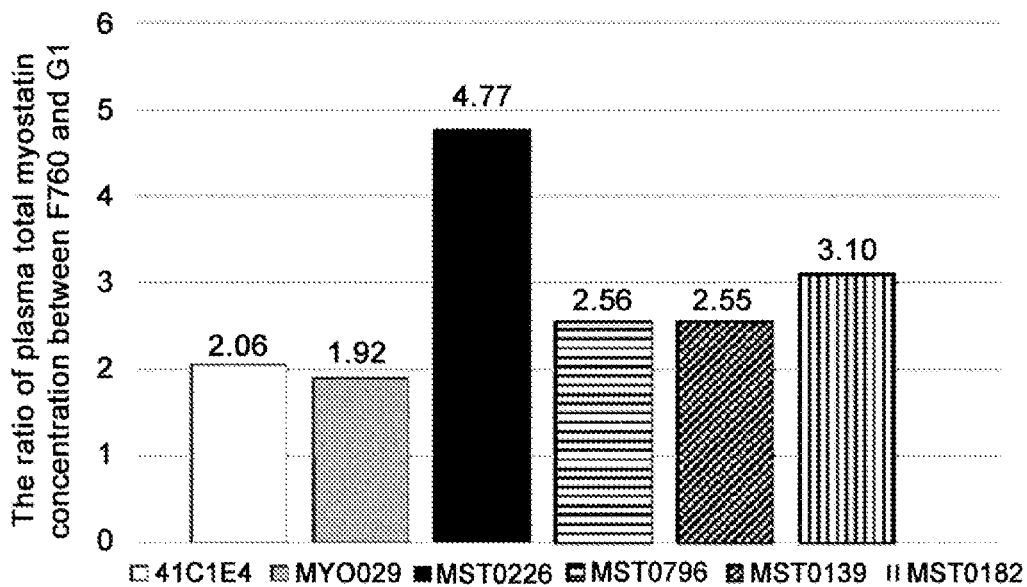
FIG. 2 illustrates comparison of antigen clearance from plasma among anti-mature myostatin antibodies in vivo, as described in Example 4. For each of anti-mature myostatin antibodies MST0226, MST0796, MST0139, MST0182, 41C1E4 and MYO029, two types of modified antibodies were generated, one of which has an Fc region with Fc gamma R binding activity (G1) and the other of which has an Fc region without Fc gamma R binding activity (F760). Each of the antibodies was administered in mice together with recombinant mature myostatin, and the resulting concentration of total myostatin in plasma was measured. The extent of the antigen clearance was evaluated by calculating the ratio of (plasma total myostatin concentration measured when the antibody having F760-type Fc region was administered)/(plasma total myostatin concentration measured when the antibody having G1-type Fc region was administered). In this assay, a higher value of the ratio means that the antibody has a higher ability to be taken up into cells with its antigen (mature myostatin) through the interaction of the Fc region of the antibody and Fc gamma R on the cells, which results in enhanced antigen clearance from plasma.

The concentration of total myostatin in mouse plasma was measured by ECL. Anti-mature myostatin antibody-immobilized plates were prepared by dispensing anti-mature myostatin antibody RK35 (as described in WO2009058346) onto a MULTI-ARRAY 96-well plate (Meso Scale Discovery) and incubated overnight at 4 degrees C. Mature myostatin calibration curve samples and mouse plasma samples diluted 40-fold or more were prepared. The samples were mixed in an acidic solution (0.2 M Glycine-HCl, pH 2.5) to dissociate mature myostatin from its binding protein (such as propeptide). Subsequently, the samples were added onto an anti-mature myostatin antibody-immobilized plate, and allowed to bind for 1 hour at room temperature before washing. Next, SULFO TAG labelled anti-mature myostatin antibody RK22 (as described in WO2009058346) was added and incubated for 1 hour at room temperature before washing. Read Buffer T (×4) (Meso Scale Discovery) was immediately added to the plate and signal was detected by SECTOR Imager 2400 (Meso Scale Discovery). The mature myostatin concentration was calculated based on the response of the calibration curve using the analytical software SOFTmax PRO (Molecular Devices). The ratio of total myostatin concentration in plasma at day 7 between F760 and G1 after intravenous administration measured by this method is shown in FIG. 2, as ratios of (plasma total myostatin concentration measured when the antibody having F760-type Fc region was administered)/(plasma total myostatin concentration measured when the antibody having G1-type Fc region was administered).

Effect of Fc Gamma R Binding on Myostatin Accumulation In Vivo

A 2.06 fold difference of plasma total myostatin concentration was observed between the 41C1E4-F760-administered group and the 41C1E4-G1-administered group, and a 1.92 fold difference of plasma total myostatin concentration was observed between the MYO029-F760-administered group and the MYO029-G1-administered group. In contrast, a 4.77, 2.56, 2.55, and 3.10 fold-difference of plasma total myostatin concentration was observed between MST0226-F760 and MST0226-G1, between MST0796-F760 and MST0796-G1, between MST0139-F760 and MST0139-G1, and between MST0182-F760 and MST0182-G1, respectively. Since mature myostatin is a dimeric protein, anti-mature myostatin antibodies are expected to form a multimeric, large immune complex which contains two or more Fc regions. Moreover, optimal size and form of immune complex can accelerate the uptake of immune complex into cell via Fc gamma R. Although 41C1E4 and MYO029 showed only 2 fold difference of plasma total myostatin concentration between their F760-type form and their G1-type form, MST0226, MST0796, MST0139 and MST0182 showed more than 2.5 fold difference of plasma total myostatin concentration between their F760-type form and their G1-type form. The result suggests that MST0226, MST0796, MST0139 and MST0182 have potential for faster uptake of immune complex compared to 41C1E4 and MYO029.

Example 5

In Vivo Efficacy of Anti-Mature Myostatin Antibody on Muscle Mass

The in vivo efficacy of anti-mature myostatin antibodies 41C1E4 (as described in U.S. Pat. No. 7,632,499), MST0226-G1m, and MST0796-G1m was evaluated in mice. 41C1E4 was used as positive control in this study. To avoid potential immunomodulation due to mouse anti-human antibody response, in vivo studies were performed in immune-deficient Severe Combined Immunodeficient (SCID) mice. Five-week-old SCID (C.B-17 SCID) mice (Charles River Laboratories Japan, Inc. (Kanagawa, JAPAN)) were given intravenous administration of a monoclonal antibody at 2 mg/kg or 10 mg/kg, or vehicle (PBS) once per week for two weeks. On day 0, 4, 7 and 14, full body lean mass was assessed by nuclear magnetic resonance (NMR) (the minispec LF-50, Bruker Bio Spin (Kanagawa, JAPAN)). The animals were euthanized on day 14, and the gastrocnemius, quadriceps, plantaris, masseter, and soleus muscles were dissected and weighed. Each isolated muscle weight in antibody treatment group was standardized by the isolated muscle weight in the PBS treatment group. Statistical significance was determined by ANOVA, a Student's t-test and a Dunnett's test with JMP 9 software (SAS, Inc.). A p value of less than 0.05 was considered significant. The results are shown in FIGS. 3 and 4. Both antibodies MST0226-G1m and MST0796-G1m increased lean body mass measured by NMR and isolated muscle weight, compared with the PBS treatment group. This indicates that MST0226-G1m and MST0796-G1m have an ability to increase muscle in mice.

Example 6

Generation of Humanized and pH-Dependent Anti-Mature Myostatin Antibody

Humanization was carried out on MST0226-G1m to generate a humanized antibody, MSLO00-SG1. The polynucleotides encoding the heavy and light chains were synthesized by GenScript Inc. and were cloned into expression vectors (See Table 3 for amino acid sequences and nucleotide sequences). MSLO00-SG1 was transiently expressed in FS293 cells and HEK Blue Assay was carried out as described above. As shown in FIG. 5, MSLO00-SG1 showed comparable inhibition activity to MST0226-G1m, hence, humanization was successfully completed.

To generate pH-dependent anti-mature myostatin antibodies, comprehensive mutagenesis was conducted on all CDRs of MSLO00-SG1. Each amino acid in the CDRs was individually substituted with any of 18 other amino acids except cysteine. Mutated variants were transiently expressed and evaluated by Biacore assay as described below.

pH dependent binding of MST0226 variants to human mature myostatin were determined at 37 degrees C. using Biacore T200 instrument (GE Healthcare). Biotinylated mature myostatin was immobilized onto streptavidin sensor chip (GE Healthcare). In order to assess pH dependent binding of MST0226 variants to mature myostatin, 100 nM of antibodies were injected over mature myostatin sensor surface at pH 7.4 (20 mM ACES, 150 mM NaCl, 1.2 mM $CaCl_2$), 0.05% Tween 20, 0.005% $NaN_3$), followed by dissociation at pH 7.4 and an additional dissociation phase at pH5.8. This is to assess the pH-dependent dissociation of antibody/antigen complexes formed at pH 7.4. The dissociation rate (kd) at both pH 7.4 and pH 5.8 buffer was determined by processing and fitting data using Scrubber 2.0 (BioLogic Software) curve fitting software. The ratio of (kd at pH5.8)/(kd at pH 7.4) gives indication of pH dependent binding, e.g. ratio >1 indicates pH dependent binding. The sensor surface was regenerated each cycle with 10 mM Glycine-HCl, pH 1.7.

After several cycles of mutagenesis and selections, four pH dependent variants: MSLO01-SG1, MSLO02-SG1, MSLO03-SG1, and MSLO04-SG1 were successfully generated. Amino acid and nucleotide sequences of the four variants are shown in Table 3. Amino acid sequences of their hypervariable regions (HVRs) are shown in Table 4. Results of Biacore assay and HEK Blue Assay are shown in Table 5 and FIG. 5. These pH dependent variants showed pH dependency under acidic condition with ratio of (kd at pH5.8)/(kd at pH 7.4)>17. As shown in FIG. 5, the pH dependent variants showed comparable or even stronger inhibition activity in HEK Blue Assay to MSLO00-SG1 (non-pH dependent antibody).

TABLE 3

MST0226 variants and their DNA and amino acid sequences (shown as SEQ ID NOs)

| | | Variable region | | | | Constant region | | | |
| | | Heavy | | Light | | Heavy | | Light | |
| Antibody name | Abbreviation | DNA | Protein | DNA | Protein | DNA | Protein | DNA | Protein |
|---|---|---|---|---|---|---|---|---|---|
| MS_M22601H-SG1/M22608L-SK1 | MSL000-SG1 | 56 | 48 | 60 | 52 | 66 | 64 | 67 | 65 |
| MS_M22601H1020-SG1/M22608L0744-SK1 | MSL001-SG1 | 57 | 49 | 61 | 53 | 66 | 64 | 67 | 65 |
| MS_M22601H1080-SG1/M22608L0837-SK1 | MSL002-SG1 | 58 | 50 | 62 | 54 | 66 | 64 | 67 | 65 |
| MS_M22601H1082-SG1/M22608L0837-SK1 | MSL003-SG1 | 59 | 51 | 62 | 54 | 66 | 64 | 67 | 65 |
| MS_M22601H1080-SG1/M22608L0846-SK1 | MSL004-SG1 | 58 | 50 | 63 | 55 | 66 | 64 | 67 | 65 |

TABLE 4

Hypervariable region (HVR) amino acid sequences MST0226 variants (shown as SEQ ID NOs)

| | | SEQ ID NO: | | | | | |
| Antibody name | Abbreviation | HVR-H1 | HVR-H2 | HVR-H3 | HVR-L1 | HVR-L2 | HVR-L3 |
|---|---|---|---|---|---|---|---|
| MS_M22601H-SG1/M22608L-SK1 | MSL000-SG1 | 70 | 72 | 75 | 77 | 81 | 82 |
| MS_M22601H1020-SG1/M22608L0744-SK1 | MSL001-SG1 | 71 | 72 | 76 | 78 | 81 | 83 |
| MS_M22601H1080-SG1/M22608L0837-SK1 | MSL002-SG1 | 71 | 73 | 76 | 79 | 81 | 83 |

TABLE 4-continued

Hypervariable region (HVR) amino acid sequences MST0226 variants (shown as SEQ ID NOs)

| Antibody name | Abbreviation | SEQ ID NO: | | | | | |
|---|---|---|---|---|---|---|---|
| | | HVR-H1 | HVR-H2 | HVR-H3 | HVR-L1 | HVR-L2 | HVR-L3 |
| MS_M22601H1082-SG1/M22608L0837-SK1 | MSL003-SG1 | 71 | 74 | 76 | 79 | 81 | 83 |
| MS_M22601H1080-SG1/M22608L0846-SK1 | MSL004-SG1 | 71 | 73 | 76 | 80 | 81 | 83 |

TABLE 5

Kinetics parameters of MST0226 variants

| | kd ($s^{-1}$) | | Ratio of (kd pH |
|---|---|---|---|
| Ab name | pH 5.8 | pH 7.4 | 5.8)/(kd pH 7.4) |
| LO00-SG1 | 6.04E−05 | 7.82E−05 | 0.8 |
| LO01-SG1 | 2.28E−03 | 1.31E−04 | 17.4 |
| LO02-SG1 | 2.54E−03 | 9.70E−05 | 26.2 |
| LO03-SG1 | 3.21E−03 | 1.20E−04 | 26.8 |
| LO04-SG1 | 1.09E−03 | 4.19E−05 | 25.9 |

Example 7

Effect of pH Dependent Mature Myostatin Binding Against Plasma Total Myostatin Concentration in Mice
In Vivo Test Using C.B-17 Scid Mice The kinetics of total exogenous and endogenous myostatin was assessed in vivo upon administration of an anti-mature myostatin antibody and recombinant mature myostatin in C.B-17 scid mice (In Vivos, Singapore) as described in Example 4. The anti-mature myostatin antibodies used are MSLO00-SG1, MSLO01-SG1, MSLO02-SG1, MSLO03-SG1, and MSLO04-SG1 which are described above. The four pH-dependent variants (MSLO01-SG1, MSLO02-SG1, MSLO03-SG1, and MSLO04-SG1) were compared with the non pH-dependent antibody MSLO00-SG1.
Measurement of Total Myostatin Concentration in Plasma by Electrochemiluminescence (ECL)

Figure 6A:
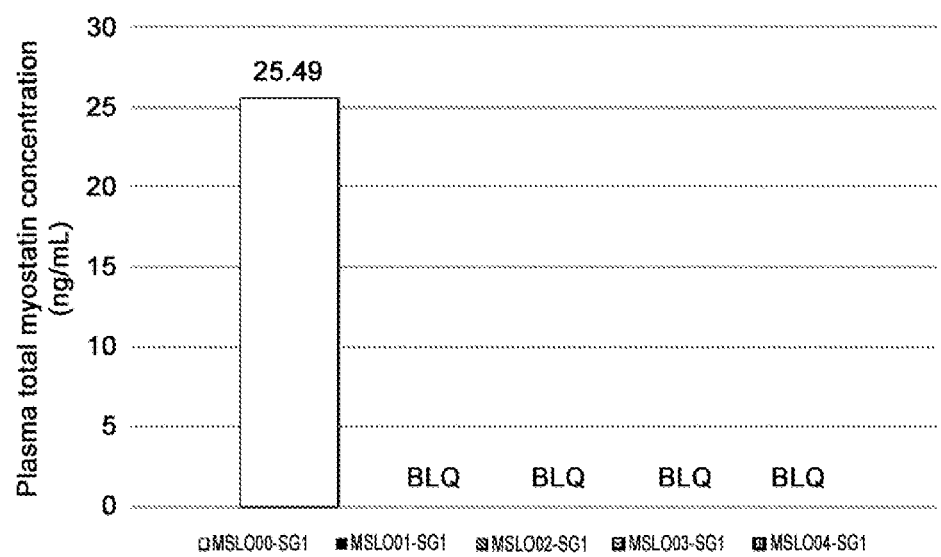
FIGS. 6A and 6B illustrate comparison of antigen clearance from plasma among anti-mature myostatin antibodies in vivo, as described in Example 7. For each of anti-mature myostatin antibodies MSLO00-SG1, MSLO01-SG1, MSLO02-SG1, MSLO03-SG1 and MSLO04-SG1, two types of modified antibodies were generated, one of which has an Fc region with Fc gamma R binding activity (G1) and the other of which has an Fc region without Fc gamma R binding activity (F760). Each of the antibodies was administered in mice together with recombinant mature myostatin, and the resulting concentration of total myostatin in plasma was measured.
Figure 6B:
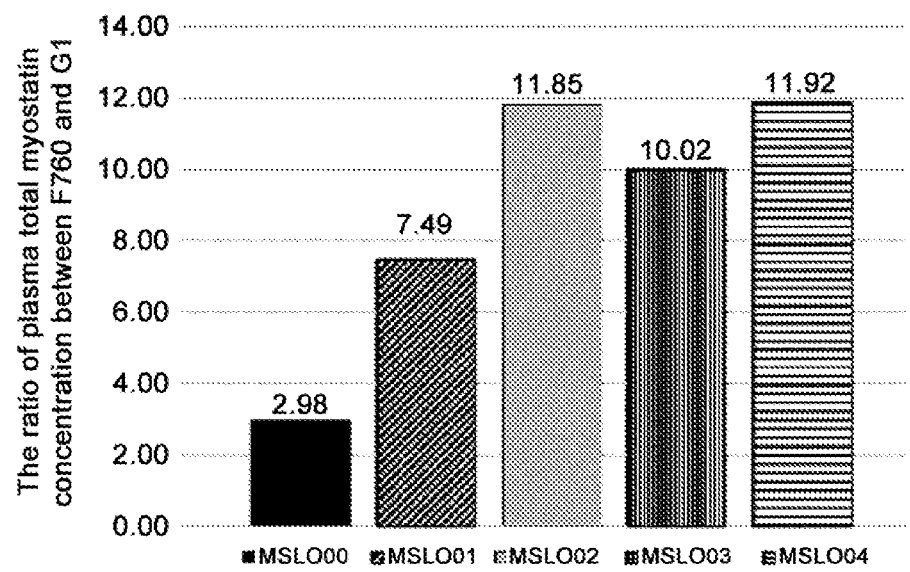

The concentration of total myostatin in mouse plasma was measured by ECL as described in Example 4. The lower limit of quantitation of assay was 2.44 ng/mL. When quantitative value was below the lower limit of quantitation, it was described as "BLQ" (below the limit of quantitation). The plasma total myostatin concentration at day 7 after intravenous administration of an antibody as measured by this method is shown in FIG. 6A. The ratio of total myostatin concentration in plasma at day 7 between F760 and G1 after intravenous administration measured by this method is shown in FIG. 6B. When quantitative value was below the lower limit of quantitation, 2.44 ng/ml was used to calculate the ratio of total myostatin concentration.
Effect of pH Dependent Binding to Myostatin Accumulation In Vivo After administration of MSLO00-SG1, plasma total myostatin concentration at day 7 showed 25.49 ng/mL. In contrast, after administration of MSLO01-SG1, MSLO02-SG1, MSLO03-SG1, or MSLO04-SG1, plasma total myostatin concentration at day 7 showed BLQ. Administration of the pH-dependent anti-mature myostatin antibodies reduced total myostatin concentration over 10 fold compared to the non pH-dependent anti-mature myostatin antibody (FIG. 6A). A 2.98 fold difference of plasma total myostatin concentration was observed between the MSLO00-F760-administered group and the MSLO00-SG1-administered group, while a 7.49, 11.85, 10.02, and 11.92 fold difference of plasma total myostatin concentration was observed between MSLO01-F760 and MSLO01-SG1, between MSLO02-F760 and MSLO02-SG1, between MSLO03-F760 and MSLO03-SG1, and between MSLO04-F760 and MSLO04-SG1, respectively. Administration of the pH-dependent anti-mature myostatin antibodies accelerated Fc gamma R-mediated elimination of mature myostatin from plasma, compared to the non pH-dependent anti-mature myostatin antibody (FIG. 6B).

Example 8

In Vivo Efficacy of pH-Dependent Anti-Mature Myostatin Antibody

The in vivo efficacy of MSLO00-SG1 (non-pH dependent antibody) and MSLO03-SG1 (pH dependent antibody) were evaluated in mice as described in Example 5. Grip strength was measured with a grip strength test meter (e.g., GPM-100B, MELQUEST Ltd., (Toyama, JAPAN)). In this study, both antibodies were administered at different dose from 0.5 mg/kg to 10 mg/kg. Lean body mass was measured as an index of muscle increment, and grip strength was measured as an index of muscle function. The results are shown in FIGS. 7 and 8. Both antibodies increased lean body mass and grip strength dose dependently. When the increment of lean body mass and the improvement of grip strength of MSLO00-SG1 and MSLO03-SG1 were compared at the same dose, MSLO03-SG1 showed the superior efficacy in muscle increment and muscle function to MSLO00-SG1. This indicates that the reduction of mature myostatin concentration by pH dependent antibody leads to the increase in muscle mass and the improvement in muscle function at lower dose.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of producing an antibody, the method comprising:
preparing a nucleic acid encoding an antibody that binds to mature myostatin homodimer having the amino acid sequence of SEQ ID NO:2; and
culturing an isolated host cell comprising the nucleic acid so that the antibody is produced,
wherein the antibody has been determined to have at least 2.5-fold higher cellular uptake compared with a reference antibody which is identical to the antibody except that the Fc region of the reference antibody has no Fc gamma receptor-binding activity, and
wherein the antibody comprises (a) HVR-H1 comprising the amino acid sequence $X_1YVX_2G$, wherein $X_1$ is N or H, $X_2$ is M or K (SEQ ID NO: 84), (b) HVR-H2 comprising the amino acid sequence IINIX$_1$GX$_2$TYYASWAX$_3$G, wherein $X_1$ is S or E, $X_2$ is S or E, $X_3$ is K or E (SEQ ID NO: 85), (c) HVR-H3 comprising the amino acid sequence GX$_1$DNFGYSYX$_2$DFNL, wherein $X_1$ is G or H, $X_2$ is I or H (SEQ ID NO: 86), (d) HVR-L1 comprising the amino acid sequence QASX$_1$SIX$_2$X$_3$X$_4$LS, wherein $X_1$ is Q or E, $X_2$ is S or H, $X_3$ is N or H, $X_4$ is E or D (SEQ ID NO: 87); (e) HVR-L2 comprising the amino acid sequence LASTLAS (SEQ ID NO: 81); and (f) HVR- L3 comprising the amino acid sequence QTYDGISX$_1$YGVA, wherein X$_1$ is S or H (SEQ ID NO: 88).

2. The method of claim 1, wherein the higher cellular uptake is caused by the interaction between the Fc region of the antibody and Fc gamma receptor on the cells.

3. The method of claim 1, wherein the antibody has been determined to have a kd ratio of (kd at pH 5.8)/(kd at pH 7.4) of 17 or greater.

4. The method of claim 1, wherein the antibody comprises a VH sequence of any one of SEQ ID NOs: 48-51 and a VL sequence of any one of SEQ ID NOs: 52-55.

5. The method of claim 1, wherein the antibody comprises (a) HVR-H1 comprising the amino acid sequence of SEQ ID NO: 71, (b) HVR-H2 comprising the amino acid sequence of SEQ ID NO: 74, (c) HVR-H3 comprising the amino acid sequence of SEQ ID NO: 76, (d) HVR-L1 comprising the amino acid sequence of SEQ ID NO: 79; (e) HVR-L2 comprising the amino acid sequence of SEQ ID NO: 81; and (f) HVR-L3 comprising the amino acid sequence of SEQ ID NO: 83.

6. The method of claim 1, wherein the antibody comprises a VH sequence of SEQ ID NO: 51 and a VL sequence of SEQ ID NO: 54.

* * * * *